United States Patent
Breslin et al.

(10) Patent No.: US 8,975,261 B2
(45) Date of Patent: Mar. 10, 2015

(54) ARYLOXMETHYL CYCLOPROPANE DERIVATIVES AS PDE10 INHIBITORS

(75) Inventors: Michael J. Breslin, Drexel Hill, PA (US); Christopher D. Cox, Harleysville, PA (US); Timothy J. Hartingh, Blue Bell, PA (US); Joseph Pero, Harleysville, PA (US); Izzat T. Raheem, Doylestown, PA (US); Michael Rossi, Limerick, PA (US); Laura Vassallo, Drexel Hill, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/117,313

(22) PCT Filed: May 21, 2012

(86) PCT No.: PCT/US2012/038759
§ 371 (c)(1),
(2), (4) Date: Nov. 12, 2013

(87) PCT Pub. No.: WO2012/162213
PCT Pub. Date: Nov. 29, 2012

(65) Prior Publication Data
US 2014/0336195 A1 Nov. 13, 2014

Related U.S. Application Data

(60) Provisional application No. 61/489,457, filed on May 24, 2011.

(51) Int. Cl.
| | | |
|---|---|---|
| C07D 401/14 | (2006.01) | |
| C07D 239/34 | (2006.01) | |
| A61K 31/444 | (2006.01) | |
| C07D 487/04 | (2006.01) | |
| C07D 413/14 | (2006.01) | |
| C07D 401/12 | (2006.01) | |
| C07D 403/14 | (2006.01) | |
| C07D 417/14 | (2006.01) | |
| C07D 471/04 | (2006.01) | |

(52) U.S. Cl.
CPC ............ C07D 487/04 (2013.01); C07D 401/14 (2013.01); C07D 413/14 (2013.01); C07D 401/12 (2013.01); C07D 403/14 (2013.01); C07D 417/14 (2013.01); C07D 471/04 (2013.01)
USPC ...... 514/255.05; 514/269; 514/300; 514/333; 514/334; 514/335; 544/319; 544/405; 546/122; 546/256; 546/272.1; 546/275.4

(58) Field of Classification Search
USPC ............... 544/319, 405; 546/122, 256, 272.1, 546/275.4; 514/255.05, 269, 300, 333, 334, 514/335
See application file for complete search history.

(56) References Cited

U.S. PATENT DOCUMENTS

| | | | |
|---|---|---|---|
| 8,785,467 B2 * | 7/2014 | Cox et al. ................ | 514/274 |
| 2007/0155779 A1 | 7/2007 | Verhoest et al. | |
| 2010/0160280 A1 | 6/2010 | Allen et al. | |
| 2010/0317698 A1 | 12/2010 | Goldstein et al. | |
| 2011/0028501 A1 | 2/2011 | Wood et al. | |

FOREIGN PATENT DOCUMENTS

WO   WO 2012/044561   *   4/2012

OTHER PUBLICATIONS

Layzer, Degenerative Diseases of the Nervous System, Cecil Textbook of Medicine, 20$^{th}$ Edition, vol. 2, pp. 2050-2057 (1996).*
Damasio, Alzheimer's Disease and Related Dementias, Cecil Textbook of Medicine, 20$^{th}$ Edition, vol. 2, pp. 1992-1996 (1996).*
Jordan, Nature Reviews: Drug Discovery, vol. 2, Issue 3, pp. 205-213 (2003).*
Becker et al., Phosphodiesterase Inhibitors—Are They Potential Neuroleptic Drugs?, Behavioural Brain research, 2008, pp. 155-160, 186.
Fakhfakh et al., Expeditious Preparation of 2-Substituted Quinolines, Tetrahedron Letters, 2001, pp. 3847-3850, 42.
Fujishige et al., Cloning and Characterization of a Novel Human Phosphodiesterase That Hydrolyzes Both cAMPand cGMP (PDE10A), J. of Biological Chemistry, Jun. 25, 1999, pp. 18438-18445, 274.
Huang et al., A Fluroescence Polarization Assay for Cyclic Nucleotide Phosphodiesterases, J. of Biomolecular Screening, 2002, pp. 215-222, 7.
Kehler, The Potential Therapeutic Use of Phosphodiesterase 10 Inhibitors, Expert Opinion, 2007, pp. 147-158, 17.
Lieberman et al., Effectiveness of Antipsychotic Drugs in Patients with Chronic Schizophrenia, New England J. of Medicine, Sep. 22, 2005, pp. 1209-1223, 353, US.
Loughney et al., Isolation and Characterization of PDE10A, a Novel Human 3', 5'-Cyclic Nucleotide Phosphodiesterase, Gene, 1999, pp. 109-117, 234.
Schmidt et al., Preclinical Characterization of Selective Phosphodiesterease 10A Inhibitors: A New Therapeutic Approach to the Treatment of Schizophrenia, J. of Pharmacology and Experimental Therapeutics, 2008, pp. 690-690, 325.
Siuciak et al., Inhibiton of the Striatum-Enriched Phosphodiesterease PDE10A: A novel Approach to the Treament of Psychosis, Neuropharmacology, 2006, pp. 386-396, 51.
Soderling et al., Isolation and Characterization of a Dual-Substrate Phosphodiesterase Gene Family: PDE10A, Proc. Natl. Acad. Sci. USA, Jun. 1999, pp. 7071-7076, 96.

(Continued)

*Primary Examiner* — Deepak Rao
(74) *Attorney, Agent, or Firm* — Sylvia A. Ayler; John C. Todaro

(57) ABSTRACT

The present invention is directed to aryloxymethyl cyclopropane derivatives which are useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

13 Claims, No Drawings

(56) References Cited

OTHER PUBLICATIONS

Threlfell et al., Inhibition of Phosphodiesterase 10A Increases the Responsiveness of Striatal Projection Neurons to the Cortical Stimulation, J. of Pharmacology and Experimental Therapeutics, 2009, pp. 785-795, 328.

Mosser et al., Automation of In Vitro Dose-Inhibition Assays Utilizing the Tecan Genesis and an Integrated Software Package to Support the Drug Discovery Process, JALA, 2003, pp. 54-63, 54.

* cited by examiner

ARYLOXMETHYL CYCLOPROPANE DERIVATIVES AS PDE10 INHIBITORS

CROSS REFERENCE TO RELATED APPLICATIONS

This application is a 371 of International Application No. PCT/US2012/038759 filed on May 21, 2012, which claims the benefit under 35 U.S.C. 119(e) of U.S. Provisional Application No. 61/489,457, filed May 24, 2011.

FIELD OF THE INVENTION

The invention relates generally to compounds which act as inhibitors of the phosphodiesterase (PDE) 10 enzyme, compositions and therapeutic uses thereof.

BACKGROUND OF THE INVENTION

Schizophrenia is debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncomplicance or discontinuation of medication. Dissatisfaction with therapy is attributed to lack of efficacy or intolerable and unacceptable side affects. The side effects have been associated with significant metabolic, extrapyramidal, prolactic and cardiac adverse events. See, Lieberman et al., *N. Engl. J. Med.* (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophasphate (cGMP) levels and the dopaminergic D2 receptor associated with cyclic adenosine monophosphate (cAMP). These ubiquitous second messengers are responsible for altering the function of many intracellular proteins. Cyclic AMP is thought to regulate the activity of cAMP-dependent protein kinase (PKA), which in turns phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these enzymes, known as 3',5'-cyclic nucleotide specific phosphodiesterases (PDEs). The PDE superfamily includes twenty one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45% suggests that it may be possible to develop selective inhibitors for each of these subtypes.

The identification of PDE 10 was reported by three groups independently and was distinguished from other PDEs on the basis of its amino acid sequence, functional properties, and tissue distribution (Fujishige et al., *J. Biol. Chem.* (1999) 274:18438-18445; Loughney et al., *Gene* (1999) 234: 109-117; Soderling et al., *PNAS, USA* (1999) 96: 7071-7076). The PDE10 subtype at present consists of a sole member, PDE 10A, having alternative splice variants at both the N-terminus (three variants) and C-terminus (two variants), but that does not affect the GAF domain in the N-terminus or the catalytic site in C-terminus. The N-terminus splice variants, PDE10A1 and PDE10A2, differ in that the A2 variant has a PKA phosphorylation site that upon activation, i.e. PKA phosphorylation in response to elevated cAMP levels, results in intracellular changes to the localization of the enzyme. PDE10A is unique relative to other PDE families also having the conserved GAF domain in that its ligand is cAMP, while for the other GAF-domain PDEs the ligand is cGMP (Kehler et al., *Expert Opin. Ther. Patents* (2007) 17(2): 147-158). PDE10A has limited but high expression in the brain and testes. The high expression in the brain and, in particular, the neurons of the striatum, unique to PDE10, suggests that inhibitors thereto may be well suited from treating neurological and psychiatric disorders and conditions.

Inhibition of PDE10 is believed to be useful in the treatment of schizophrenia and a wide variety of conditions or disorders that would benefit from increasing levels of cAMP and/or cGMP within neurons, including a variety neurological, psychotic, anxiety and/or movement disorders. Accordingly, agents that inhibit PDE10 and especially PDE10A would be desirable as therapeutics for neurological and psychiatric disorders.

SUMMARY OF THE INVENTION

The present invention is directed to aryloxymethyl cyclopropane derivatives, which are useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

DETAILED DESCRIPTION OF THE INVENTION

The present invention is directed to compounds of the formula I:

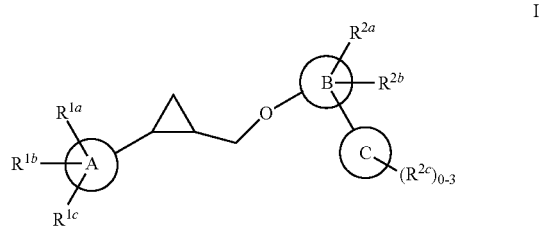

wherein:
A is $C_{5-10}$heterocyclyl;
B is a $C_{5-10}$heterocyclyl selected from the group consisting of pyrimidinyl, naphthridinyl, pyrazinyl and pyridyl;
C is selected from the group consisting of $(CH_2)_nC_{5-10}$heterocyclyl, $(CH_2)_nO$—$C_{5-10}$heterocyclyl, $C_{2-6}$alkenyl $C_{5-10}$heterocyclyl, $C_{3-10}$cycloalkyl, and $C_{3-10}$cycloalkenyl;
$R^{1a}$, $R^{1b}$ and $R^{1c}$ may be absent if the valency of A does not permit such substitution and are independently selected from the group consisting of:
(1) hydrogen,
(2) halogen, (3) hydroxyl,
(4) $C_{1-6}$alkyl, which alkyl is unsubstituted or substituted with halogen, hydroxyl, phenyl or napthyl,
(5) —O—$C_{1-6}$alkyl, which alkyl is unsubstituted or substituted with halogen, hydroxyl or phenyl,
(6) phenyl, which is unsubstituted or substituted with 1 to 3 groups of $R^a$,
(7) $C_{5-10}$ heterocyclyl, which is unsubstituted or substituted with 1 to 3 groups of $R^a$,
(8) $C_{2-6}$alkyl$C_{5-10}$ heterocyclyl, which heterocycle is unsubstituted or substituted with 1 to 3 groups of $R^a$,
(8) —O-phenyl, which is unsubstituted or substituted with 1 to 3 groups of $R^a$,
(9) $C_{3-10}$cycloalkyl which is unsubstituted or substituted with 1 to 3 groups of $R^a$,
(10) —NH—$C_{1-6}$alkyl, or —N($C_{1-6}$alkyl)($C_{1-6}$alkyl), which alkyl is unsubstituted or substituted with 1 to 3 groups of $R^a$,
(11) —$CO_2H$,
(12) —CN, and
(13) —$NO_2$;
$R^{2a}$, $R^{2b}$ and $R^{2c}$ may be absent if the valency of B does not permit such substitution and are independently selected from the group consisting of:
(1) hydrogen,
(2) halogen,
(3) hydroxyl,
(4) $C_{1-6}$alkyl, which alkyl is unsubstituted or substituted with halogen, OR, phenyl or napthyl,
(5) —O—$C_{1-6}$alkyl, which alkyl is unsubstituted or substituted with halogen, hydroxyl or phenyl,
(6) phenyl, which is unsubstituted or substituted with 1 to 3 groups of $R^a$,
(7) $(CH_2)_n$heterocyclyl, which is unsubstituted or substituted with 1 to 3 groups of $R^a$,
(8) $C_{2-6}$alkenyl$C_{5-10}$heterocyclyl, which is unsubstituted or substituted with 1 to 3 groups of $R^a$,
(9) $(CH_2)_nO$—$C_{5-10}$heterocyclyl, which is unsubstituted or substituted with 1 to 3 groups of $R^a$,
(10) $C_{3-10}$cycloalkyl which is unsubstituted or substituted with 1 to 3 groups of $R^a$,
(11) —O-phenyl, which is unsubstituted or substituted with halogen, hydroxyl, —O—$C_{1-6}$alkyl or $C_{1-6}$alkyl, which is unsubstituted or substituted with fluoro,
(12) —$N(R)_2$, wherein when R is alkyl it is unsubstituted or substituted 1 to 3 groups of $R^a$,
(13) —$CO_2R$,
(14) $B(OH)_2$;
(15) —CN,
(16) —$NO_2$,
(17) C(O)R, and
(18) $C_{2-6}$alkenyl;
R is $C_{1-6}$alkyl or hydrogen;
$R^a$ is selected from the group consisting of:
(1) hydroxyl,
(2) halogen,
(3) $C_{1-6}$alkyl,
(4) —$C_{3-6}$cycloalkyl,
(5) —O—$C_{1-6}$alkyl,
(6) —O(C=O)—$C_{1-6}$alkyl,
(7) $C_{1-6}$alkylOH,
(8) $(CH_2)_nOC_{1-6}$alkyl
(8) —$CO_2H$,
(9) —$CO_2$—$C_{1-6}$alkyl,
(10) —C(O)—$C_{1-6}$alkyl,
(12) phenyl, which is unsubstituted or substituted with halogen, hydroxyl, —O—$C_{1-6}$alkyl or $C_{1-6}$alkyl, which is unsubstituted or substituted with fluoro,
(14) $(CH_2)_n$heterocyclyl, which is unsubstituted or substituted with halogen, hydroxyl, —O—$C_{1-6}$alkyl or $C_{1-6}$alkyl, which is unsubstituted or substituted with fluoro,
(15) —CN, and
(16) $N(R)_2$
n is 0-4;
or a pharmaceutically acceptable salt thereof.

An embodiment of the present invention includes compounds wherein A is selected from the group consisting of pyridyl, cyclopentapyridinyl, dihydropyrrolopyrazolyl, pyrazolopyridinyl, thiazolyl, oxazolyl, pyrazolyl, quinolinyl, tetrahydronaphthyridinyl, or naphthyridine and all other variables are as originally described. A further subembodiment of this aspect of the invention is realized when A is pyridyl. Still another subembodiment of this aspect of the invention is realized with A is naphthryridine. Yet another subembodiment of this aspect of the invention is realized with A is tetrahydronaphthryridinyl. Still another subembodiment of this aspect of the invention is realized with A is quinolinyl.

Still another embodiment of the present invention includes compounds wherein $R^{1a}$, $R^{1b}$ and $R^{1c}$ are independently selected from hydrogen, halo, $C_{1-6}$ alkyl, and —O—$C_{1-6}$alkyl. A subembodiment of this aspect of the invention is realized when one of $R^{1a}$, $R^{1b}$ and $R^{1c}$ is methyl, methoxy or halo and the other two are hydrogen. Another subembodiment of this aspect of the invention is realized when one of $R^{1a}$, $R^{1b}$ and $R^{1c}$ is methoxy and the other two are hydrogen.

Another embodiment of the present invention includes compounds wherein B is naphthyridinyl and all other variables are as originally described.

Another embodiment of this aspect of the invention includes compounds wherein B is pyrimidinyl and all other variables are as originally described.

Still another embodiment of this aspect of the invention includes compounds wherein B is pyrazinyl and all other variables are as originally described.

Yet another embodiment of this aspect of the invention includes compounds wherein B is pyridyl and all other variables are as originally described.

Another embodiment of the present invention includes compounds wherein C is an optionally substituted $C_{5-10}$heterocyclyl and all other variables are as originally described. A subembodiment of this aspect of the invention is realized when C is an optionally substituted heterocyclyl selected from the group consisting of thiazolyl, pyridyl, thiadiazolyl, imidazopyrimidinyl, pyrazolyl, isoxazolyl, ethenylpyridinyl, pyrrolyl, dihydropyrrolopyrazolyl, imidazopyridinyl, pyrazolopyridazinyl, triazolyl, triazolopyridinyl, pyrrolidinyl, dihydronaphthyridinyl, tetrahydronaphthyridinyl, dihydropyridinyl, methoxypyridinyl, $CH_2O$-pyridyl, pyrrolopyridinyl, $C_{2-6}$alkenylpyridyl, and pyrrolopyrazolyl. A further subembodiment of this aspect of the invention is realized when C is an optionally substituted heterocyclyl selected from the group consisting of pyrazolyl, pyridyl, thiazolyl, ethenylpyridinyl, dihydropridinyl, pyrrolindinyl, and pyrrolopyrazolyl. A still further subembodiment of this aspect of the invention is realized when C is an optionally substituted heterocycle selected from the group consisting of pyrazolyl, pyridyl, and thiazolyl. Yet another subembodiment of this aspect of the invention is realized when C is an optionally substituted pyrazolyl. Another subembodiment of this aspect of the invention is realized when C is an optionally substituted pyridyl. Another subembodiment of this aspect of the invention is realized when C is an optionally substituted thiazolyl.

Another embodiment of the present invention includes compounds wherein C is an optionally substituted $C_{3-10}$cycloalkyl or $C_{3-10}$cycloalkenyl selected from the group consisting of cyclohexenyl, cyclopentenyl, and cyclohexyl and all other variables are as originally described.

Another embodiment of the present invention includes compounds wherein $R^{2a}$, $R^{2b}$ and $R^{2c}$ are independently selected from the group consisting of hydrogen, halogen, hydroxyl, C(O)R, CN, $N(R)_2$, pyrazolyl, $C_{1-6}$ alkyl, $OC_{1-6}$ alkyl, $C_{2-6}$ alkenyl, dimethylamino, dihydropyrrolopyrazolyl, thiazolyl, piperidinyl, pyrrolidinyl, ethenylpyridinyl, naphthyridinyl, $C_{1-6}$ alkylOH, $(CH_2)_n$pyridyl, imidazopyrimidinyl, methoxypyridinyl, thiadiazolyl, cyclohexenyl, cyclopropyl, cyclohexyl, isoxaolyl, pyridinylethenyl, cyclopentenyl, pyrrolopyridinyl, imidazolyl, pyrazolopyridazine, triazolyl, triazolopyridinyl, all of which where appropriate may be optionally substituted with 1 to 3 groups of $R^a$. A subembodiment of this aspect of the invention is realized when $R^{2a}$ and $R^{2b}$ are selected from the group consisting of hydrogen, halogen, and $C_{1-6}$ alkyl. Another subembodiment of this aspect of the invention is realized when $R^{2a}$ and $R^{2b}$ are independently selected from the group consisting of hydrogen, and $C_{1-6}$ alkyl. Still another subembodiment of this aspect of the invention is realized when $R^{2a}$ and $R^{2b}$ are both hydrogen. Another embodiment of this aspect of the invention is realized when $R^{2c}$ is selected from the group consisting of hydrogen, halogen, hydroxyl, $C_{1-6}$ alkylOH, cyclopropyl, pyridyl, $C_{1-6}$ alkyl, and $OC_{1-6}$ alkyl. Still another embodiment of this aspect of the invention is realized when $R^{2c}$ is selected from the group consisting of hydrogen, halogen, hydroxyl, $C_{1-6}$ alkylOH, $C_{1-6}$ alkyl, and $OC_{1-6}$ alkyl.

In yet another embodiment of the present invention $R^a$ is selected from the group consisting of $C_{1-6}$ alkylOH, OR, $C_{1-6}$ alkyl, halogen, $C(O)C_{1-6}$ alkyl, cyclopropyl, $N(R)_2$, and $(CH_2)_n$pyridyl.

Another embodiment of the present invention includes compounds of formula Ia

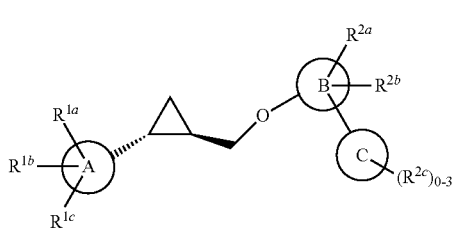

Ia wherein A, B, C, $R^{1a}$, $R^{1b}$, $R^{1c}$, $R^{2a}$, $R^{2b}$, and $R^{2c}$ are defined herein; or a pharmaceutically acceptable salt thereof. A subembodiment of the invention of formula Ia is realized when A is pyridyl.

Another embodiment of the present invention includes compounds of the formula Ib:

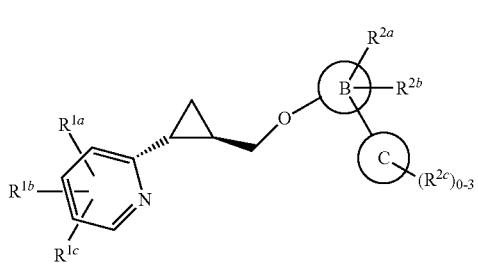

Ib wherein B, C, $R^{1a}$, $R^{1b}$, $R^{1c}$, $R^{2a}$, $R^{2b}$, and $R^{2c}$ are as originally defined herein; or a pharmaceutically acceptable salt thereof. A subembodiment of formula Ib is realized when one of $R^{1a}$, $R^{1b}$, and $R^{1c}$ is independently selected from the group consisting of hydrogen, methoxy, halo and methyl.

Another subembodiment of the invention of formula Ib is realized when $R^{2a}$, $R^{2b}$ and $R^{2c}$ are independently selected from the group consisting of hydrogen, halogen, hydroxyl, C(O)R, CN, $N(R)_2$, pyrazolyl, $C_{1-6}$ alkyl, $OC_{1-6}$ alkyl, $C_{2-6}$ alkenyl, dihydropyrrolopyrazolyl, thiazolyl, piperidinyl, pyrrolidinyl, ethenylpyridinyl, naphthyridinyl, $C_{1-6}$ alkylOH, $(CH_2)_n$pyridyl, imidazopyrimidinyl, methoxypyridinyl, thiadiazolyl, cyclohexenyl, cyclopropyl, cyclohexyl, isoxaolyl, pyridinylethenyl, cyclopentenyl, pyrrolopyridinyl, imidazolyl, pyrazolopyridazine, triazolyl, triazolopyridinyl, all of which where appropriate may be optionally substituted with 1 to 3 groups of $R^a$. Another subembodiment of the invention of formula Ib is realized when $R^{2a}$ and $R^{2b}$ are selected from the group consisting of hydrogen, halogen, and $C_{1-6}$ alkyl. Another subembodiment of the invention of formula Ib is realized when $R^{2a}$ and $R^{2b}$ are independently selected from the group consisting of hydrogen, and $C_{1-6}$ alkyl. Still another subembodiment of the invention of formula Ib is realized when $R^{2a}$ and $R^{2b}$ are both hydrogen. Another subembodiment of the invention of formula Ib is realized when $R^{2c}$ is selected from the group consisting of hydrogen, halogen, hydroxyl, $C_{1-6}$ alkylOH, cyclopropyl, pyridyl, $C_{1-6}$ alkyl, and $OC_{1-6}$ alkyl.

Another subembodiment of the invention of formula Ib is realized when C is selected from an optionally substituted group consisting of thiazolyl, pyridyl, thiadiazolyl, imidazopyrimidinyl, pyrazolyl, isoxazolyl, ethenylpyridinyl, pyrrolyl, dihydropyrrolopyrazolyl, imidazopyridinyl, pyrazolopyridazinyl, triazolyl, triazolopyridinyl, pyrrolidinyl, dihydronaphthyridinyl, tetrahydronaphthyridinyl, dihydropyridinyl, methoxypyridinyl, $CH_2O$-pyridyl, pyrrolopyridinyl, $C_{2-6}$alkenylpyridyl, and pyrrolopyrazolyl. A further subembodiment of the invention of formula Ib is realized when C is an optionally substituted pyrazolyl, pyridyl, thiazolyl, ethenylpyridinyl, dihydropridinyl, pyrrolindinyl, or pyrrolopyrazolyl. A still further subembodiment of the invention of formula Ib is realized when C is an optionally substituted heterocycle selected from the group consisting of pyrazolyl, pyridyl, and thiazolyl. Yet another subembodiment of the invention of formula Ib is realized when C is an optionally substituted pyrazolyl. Another subembodiment of the invention of formula Ib is realized when C is an optionally substituted pyridyl. Another subembodiment of the invention of formula Ib is realized when C is an optionally substituted thiazolyl.

An embodiment of the present invention includes compounds of the formula Ic:

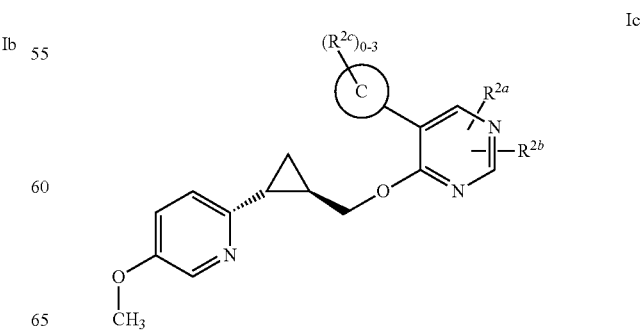

Ic wherein C, $R^{2a}$, $R^{2b}$, and $R^{2c}$ are as originally defined herein; or a pharmaceutically acceptable salt thereof. A subembodiment of the invention of formula Ic is realized when $R^{2a}$, $R^{2b}$ and $R^{2c}$ are independently selected from the group consisting of hydrogen, halogen, hydroxyl, C(O)R, CN, $N(R)_2$, pyrazolyl, $C_{1-6}$ alkyl, $OC_{1-6}$ alkyl, $C_{2-6}$ alkenyl, dihydropyrrolopyrazolyl, thiazolyl, piperidinyl, pyrrolidinyl, ethenylpyridinyl, naphthyridinyl, $C_{1-6}$ alkylOH, $(CH_2)_n$pyridyl, imidazopyrimidinyl, methoxypyridinyl, thiadiazolyl, cyclohexenyl, cyclopropyl, cyclohexyl, isoxaolyl, pyridinylethenyl, cyclopentenyl, pyrrolopyridinyl, imidazolyl, pyrazolopyridazine, triazolyl, triazolopyridinyl, all of which where appropriate may be optionally substituted with 1 to 3 groups of $R^a$. Another subembodiment of the invention of formula Ic is realized when $R^{2a}$ and $R^{2b}$ are selected from the group consisting of hydrogen, halogen, and $C_{1-6}$ alkyl. Another subembodiment of the invention of formula Ic is realized when $R^{2a}$ and $R^{2b}$ are independently selected from the group consisting of hydrogen, and $C_{1-6}$ alkyl. Still another subembodiment of the invention of formula Ic is realized when $R^{2a}$ and $R^{2b}$ are both hydrogen. Another subembodiment of the invention of formula Ic is realized when $R^{2c}$ is selected from the group consisting of hydrogen, halogen, hydroxyl, $C_{1-6}$ alkylOH, cyclopropyl, pyridyl, $C_{1-6}$ alkyl, and $OC_{1-6}$ alkyl.

Another subembodiment of the invention of formula Ic is realized when C is selected from an optionally substituted group consisting of thiazolyl, pyridyl, thiadiazolyl, imidazopyrimidinyl, pyrazolyl, isoxazolyl, ethenylpyridinyl, pyrrolyl, dihydropyrrolopyrazolyl, imidazopyridinyl, pyrazolopyridazinyl, triazolyl, triazolopyridinyl, pyrrolidinyl, dihydronaphthyridinyl, tetrahydronaphthyridinyl, dihydropyridinyl, methoxypyridinyl, $CH_2O$-pyridyl, pyrrolopyridinyl, $C_{2-6}$alkenylpyridyl, and pyrrolopyrazolyl. A further subembodiment of the invention of formula Ic is realized when C is an optionally substituted pyrazolyl, pyridyl, thiazolyl, ethenylpyridinyl, dihydropridinyl, pyrrolindinyl, or pyrrolopyrazolyl. A still further subembodiment of the invention of formula Ic is realized when C is an optionally substituted heterocycle selected from the group consisting of pyrazolyl, pyridyl, and thiazolyl. Yet another subembodiment of the invention of formula Ic is realized when C is an optionally substituted pyrazolyl. Another subembodiment of the invention of formula Ic is realized when C is an optionally substituted pyridyl. Another subembodiment of the invention of formula Ic is realized when C is an optionally substituted thiazolyl.

An embodiment of the present invention includes compounds of the formula Id:

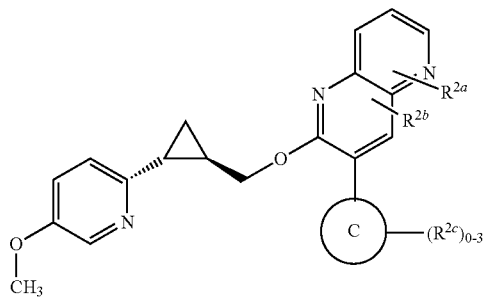

Id wherein C, $R^{2a}$, $R^{2b}$, and $R^{2c}$ are as originally defined herein; or a pharmaceutically acceptable salt thereof. A subembodiment of the invention of formula Id is realized when $R^{2a}$, $R^{2b}$ and $R^{2c}$ are independently selected from the group consisting of hydrogen, halogen, hydroxyl, C(O)R, CN, $N(R)_2$, pyrazolyl, $C_{1-6}$ alkyl, $OC_{1-6}$ alkyl, $C_{2-6}$ alkenyl, dihydropyrrolopyrazolyl, thiazolyl, piperidinyl, pyrrolidinyl, ethenylpyridinyl, naphthyridinyl, $C_{1-6}$ alkylOH, $(CH_2)_n$pyridyl, imidazopyrimidinyl, methoxypyridinyl, thiadiazolyl, cyclohexenyl, cyclopropyl, cyclohexyl, isoxaolyl, pyridinylethenyl, cyclopentenyl, pyrrolopyridinyl, imidazolyl, pyrazolopyridazine, triazolyl, triazolopyridinyl, all of which where appropriate may be optionally substituted with 1 to 3 groups of $R^a$. Another subembodiment of the invention of formula Id is realized when $R^{2a}$ and $R^{2b}$ are selected from the group consisting of hydrogen, halogen, and $C_{1-6}$ alkyl. Another subembodiment of the invention of formula Id is realized when $R^{2a}$ and $R^{2b}$ are independently selected from the group consisting of hydrogen, and $C_{1-6}$ alkyl. Still another subembodiment of the invention of formula Id is realized when $R^{2a}$ and $R^{2b}$ are both hydrogen. Another subembodiment of the invention of formula Id is realized when $R^{2c}$ is selected from the group consisting of hydrogen, halogen, hydroxyl, $C_{1-6}$ alkylOH, cyclopropyl, pyridyl, $C_{1-6}$ alkyl, and $OC_{1-6}$ alkyl.

Another subembodiment of the invention of formula Id is realized when C is selected from an optionally substituted group consisting of thiazolyl, pyridyl, thiadiazolyl, imidazopyrimidinyl, pyrazolyl, isoxazolyl, ethenylpyridinyl, pyrrolyl, dihydropyrrolopyrazolyl, imidazopyridinyl, pyrazolopyridazinyl, triazolyl, triazolopyridinyl, pyrrolidinyl, dihydronaphthyridinyl, tetrahydronaphthyridinyl, dihydropyridinyl, methoxypyridinyl, $CH_2O$-pyridyl, pyrrolopyridinyl, $C_{2-6}$alkenylpyridyl, and pyrrolopyrazolyl. A further subembodiment of the invention of formula Id is realized when C is an optionally substituted pyrazolyl, pyridyl, thiazolyl, ethenylpyridinyl, dihydropridinyl, pyrrolindinyl, or pyrrolopyrazolyl. A still further subembodiment of the invention of formula Id is realized when C is an optionally substituted heterocycle selected from the group consisting of pyrazolyl, pyridyl, and thiazolyl. Yet another subembodiment of the invention of formula Id is realized when C is an optionally substituted pyrazolyl. Another subembodiment of the invention of formula Id is realized when C is an optionally substituted pyridyl. Another subembodiment of the invention of formula Id is realized when C is an optionally substituted thiazolyl.

An embodiment of the present invention includes compounds of the formula Ie:

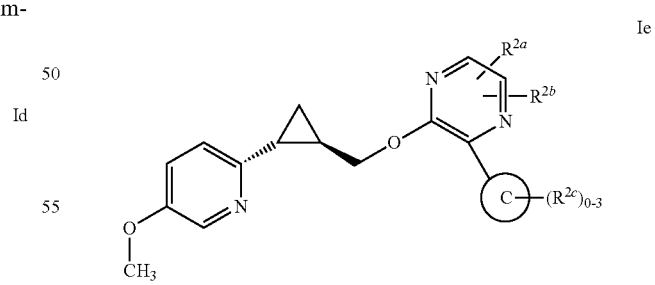

Ie wherein C, $R^{2a}$, $R^{2b}$, and $R^{2c}$ are as originally defined herein; or a pharmaceutically acceptable salt thereof. A subembodiment of the invention of formula Ie is realized when $R^{2a}$, $R^{2b}$ and $R^{2c}$ are independently selected from the group consisting of hydrogen, halogen, hydroxyl, C(O)R, CN, $N(R)_2$, pyrazolyl, $C_{1-6}$ alkyl, $OC_{1-6}$ alkyl, $C_{2-6}$ alkenyl, dihydropyrrolopyrazolyl, thiazolyl, piperidinyl, pyrrolidinyl, ethenylpyridinyl, naphthyridinyl, $C_{1-6}$ alkylOH, $(CH_2)_n$pyridyl, imidazopyrimidinyl, methoxypyridinyl, thiadiazolyl, cyclohexenyl, cyclopropyl, cyclohexyl, isoxaolyl, pyridinylethenyl, cyclopentenyl, pyrrolopyridinyl, imidazolyl, pyrazolopyridazine, triazolyl, triazolopyridinyl, all of which where appropriate may be optionally substituted with 1 to 3 groups of $R^a$. Still another subembodiment of the invention of formula Ie is realized when two of $R^{2a}$, $R^{2b}$ and $R^{2c}$ are methyl. Another subembodiment of the invention of formula Ie is realized when $R^{2a}$ and $R^{2b}$ are selected from the group consisting of hydrogen, halogen, and $C_{1-6}$ alkyl. Another subembodiment of the invention of formula Ie is realized when $R^{2a}$ and $R^{2b}$ are independently selected from the group consisting of hydrogen, and $C_{1-6}$ alkyl. Still another subembodiment of the invention of formula Ie is realized when $R^{2a}$ and $R^{2b}$ are both hydrogen. Another subembodiment of the invention of formula Ie is realized when $R^{2c}$ is selected from the group consisting of hydrogen, halogen, hydroxyl, $C_{1-6}$ alkylOH, cyclopropyl, pyridyl, $C_{1-6}$ alkyl, and $OC_{1-6}$ alkyl.

Another subembodiment of the invention of formula Ie is realized when C is selected from an optionally substituted group consisting of thiazolyl, pyridyl, thiadiazolyl, imidazopyrimidinyl, pyrazolyl, isoxazolyl, ethenylpyridinyl, pyrrolyl, dihydropyrrolopyrazolyl, imidazopyridinyl, pyrazolopyridazinyl, triazolyl, triazolopyridinyl, pyrrolidinyl, dihydronaphthyridinyl, tetrahydronaphthyridinyl, dihydropyridinyl, methoxypyridinyl, $CH_2O$-pyridyl, pyrrolopyridinyl, $C_{2-6}$alkenylpyridyl, and pyrrolopyrazolyl. A further subembodiment of the invention of formula Ie is realized when C is an optionally substituted pyrazolyl, pyridyl, thiazolyl, ethenylpyridinyl, dihydropridinyl, pyrrolindinyl, or pyrrolopyrazolyl. A still further subembodiment of the invention of formula Ie is realized when C is an optionally substituted heterocycle selected from the group consisting of pyrazolyl, pyridyl, and thiazolyl. Yet another subembodiment of the invention of formula Ie is realized when C is an optionally substituted pyrazolyl. Another subembodiment of the invention of formula Ie is realized when C is an optionally substituted pyridyl. Another subembodiment of the invention of formula Ie is realized when C is an optionally substituted thiazolyl.

An embodiment of the present invention includes compounds of the formula If:

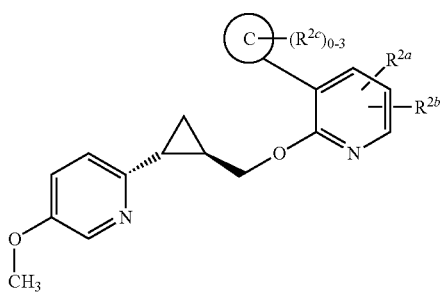

wherein C, $R^{2a}$, $R^{2b}$, and $R^{2c}$ are as originally defined herein; or a pharmaceutically acceptable salt thereof. A subembodiment of the invention of formula If is realized when $R^{2a}$, $R^{2b}$ and $R^{2c}$ are independently selected from the group consisting of hydrogen, halogen, hydroxyl, C(O)R, CN, N(R)$_2$, pyrazolyl, $C_{1-6}$ alkyl, $OC_{1-6}$ alkyl, $C_{2-6}$ alkenyl, dihydropyrrolopyrazolyl, thiazolyl, piperidinyl, pyrrolidinyl, ethenylpyridinyl, naphthyridinyl, $C_{1-6}$ alkylOH, $(CH_2)_n$pyridyl, imidazopyrimidinyl, methoxypyridinyl, thiadiazolyl, cyclohexenyl, cyclopropyl, cyclohexyl, isoxaolyl, pyridinylethenyl, cyclopentenyl, pyrrolopyridinyl, imidazolyl, pyrazolopyridazine, triazolyl, triazolopyridinyl, all of which where appropriate may be optionally substituted with 1 to 3 groups of $R^a$. Another subembodiment of the invention of formula If is realized when $R^{2a}$ and $R^{2b}$ are selected from the group consisting of hydrogen, halogen, and $C_{1-6}$ alkyl. Another subembodiment of the invention of formula If is realized when $R^{2a}$ and $R^{2b}$ are independently selected from the group consisting of hydrogen, and $C_{1-6}$ alkyl. Still another subembodiment of the invention of formula If is realized when $R^{2a}$ and $R^{2b}$ are both hydrogen. Another subembodiment of the invention of formula If is realized when $R^{2c}$ is selected from the group consisting of hydrogen, halogen, hydroxyl, $C_{1-6}$ alkylOH, cyclopropyl, pyridyl, $C_{1-6}$ alkyl, and $OC_{1-6}$ alkyl.

Another subembodiment of the invention of formula If is realized when C is selected from an optionally substituted group consisting of thiazolyl, pyridyl, thiadiazolyl, imidazopyrimidinyl, pyrazolyl, isoxazolyl, ethenylpyridinyl, pyrrolyl, dihydropyrrolopyrazolyl, imidazopyridinyl, pyrazolopyridazinyl, triazolyl, triazolopyridinyl, pyrrolidinyl, dihydronaphthyridinyl, tetrahydronaphthyridinyl, dihydropyridinyl, methoxypyridinyl, $CH_2O$-pyridyl, pyrrolopyridinyl, $C_{2-6}$alkenylpyridyl, and pyrrolopyrazolyl. A further subembodiment of the invention of formula If is realized when C is an optionally substituted pyrazolyl, pyridyl, thiazolyl, ethenylpyridinyl, dihydropridinyl, pyrrolindinyl, or pyrrolopyrazolyl. A still further subembodiment of the invention of formula If is realized when C is an optionally substituted heterocycle selected from the group consisting of pyrazolyl, pyridyl, and thiazolyl. Yet another subembodiment of the invention of formula If is realized when C is an optionally substituted pyrazolyl. Another subembodiment of the invention of formula If is realized when C is an optionally substituted pyridyl. Another subembodiment of the invention of formula If is realized when C is an optionally substituted thiazolyl.

Specific embodiments of the present invention include a compound which is selected from the group consisting of the subject compounds of the Examples herein and pharmaceutically acceptable salts thereof and individual enantiomers and diastereomers thereof.

When any variable (e.g. aryl, heterocycle, $R^1$, $R^5$ etc.) occurs more than one time in any constituent, its definition on each occurrence is independent at every other occurrence. Also, combinations of substituents/or variables are permissible only if such combinations result in stable compounds.

As used herein, "alkyl" encompasses groups having the prefix "alk" such as, for example, alkoxy, alkanoyl, alkenyl, and alkynyl and means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl. Preferably, alkenyl is $C_2$-$C_6$ alkenyl. Preferred alkynyls are $C_2$-$C_6$ alkynyl.

"Alkenyl," "alkynyl" and other like terms include carbon chains containing at least one unsaturated C—C bond.

As used herein, "haloalkyl" refers to an alkyl substituent as described herein containing at least one halo substituent such as fluoroalkyl.

The term "cycloalkyl" refers to a saturated hydrocarbon containing one ring having a specified number of carbon atoms. Examples of cycloalkyl include cyclopropyl, cyclobutyl, cyclopentyl, and cyclohexyl. For purposes of this invention "cycloalkyl" also includes unsaturated hydrocarbon containing one ring having a specified number of carbon atoms. Examples of unsaturated cycloalkyls are cyclohexenyl, cyclopentenyl, and the like.

The term "$C_{1-6}$" includes alkyls containing 6, 5, 4, 3, 2, or 1 carbon atoms The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

In certain embodiments, the heterocyclic group is a heteroaryl group.

In certain other embodiments, the heterocyclic group is fused to an aryl or heteroaryl group. Examples of such fused heterocycles include, without limitation, tetrahydroquinolinyl and dihydrobenzofuranyl.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "heteroatom" means O, S or N, selected on an independent basis.

A moiety that is substituted is one in which one or more hydrogens have been independently replaced with another chemical substituent. As a non-limiting example, substituted phenyls include 2-fluorophenyl, 3,4-dichlorophenyl, 3-chloro-4-fluoro-phenyl, 2,4-fluor-3-propylphenyl. As another non-limiting example, substituted n-octyls include 2,4 dimethyl-5-ethyl-octyl and 3-cyclopentyloctyl. Included within this definition are methylenes (—$CH_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$alkylsulfinyl, arylalkylsulfnyl, arylsulfnyl, $C_1$-$C_8$ alkylsulfonyl, arylalkylsulfonyl, arylsulfonyl, $C_0$-$C_6$ N-alkylcarbamoyl, $C_2$-$C_{15}$ N,N dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

"Halogen" and "halo" refer to fluorine, chlorine, bromine and iodine.

The term "mammal" "mammalian" or "mammals" includes humans, as well as animals, such as dogs, cats, horses, pigs and cattle.

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention may contain one or more asymmetric centers and may thus occur as racemates, racemic mixtures, single enantiomers, diastereomeric mixtures, and individual diastereomers.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

Exemplifying the invention are the specific compounds disclosed in the Examples and herein. The subject compounds are useful in a method of treating a neurological or psychiatric disorder associated with PDE10 dysfunction in a patient such as a mammal in need of such inhibition comprising the administration of an effective amount of the compound. In addition to primates, especially humans, a variety of other mammals can be treated according to the method of the present invention. The subject compounds are useful in a method of inhibiting PDE10 activity in a patient such as a mammal in need of such inhibition comprising the administration of an effective amount of the compound. The subject compounds are also useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE10 dysfunction in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy to retard the progression or reduce the risk of the noted conditions, particularly in a patient who is predisposed to such disease or disorder.

Applicants propose that inhibitors of PDE10 and, in particular inhibitors of PDE10A, will provide therapeutic benefit to those individuals suffering from psychiatric and cognitive disorders. The unique and exclusive distribution of PDE10A in the medium spiny projection neurons of the striatum, which form the principle site for cortical and dopaminergic input within basal ganglia, suggests that it may be possible and desirable to identify inhibitors of PDE10 to ameliorate or eliminate unwanted cellular signaling within this site. Without wishing to be bound by any theory, Applicants believe that inhibition of PDE10A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

As used herein, the term "selective PDE10 inhibitor" refers to an organic molecule that effectively inhibits an enzyme from the PDE10 family to a greater extent than enzymes from the PDE 1-9 or PDE11 families. In one embodiment, a selective PDE10 inhibitor is an organic molecule having a Ki for inhibition of PDE10 that is less than or about one-tenth that for a substance that is an inhibitor for another PDE enzyme. In other words, the organic molecule inhibits PDE10 activity to the same degree at a concentration of about one-tenth or less than the concentration required for any other PDE enzyme. A more selective PDE10 inhibitor is an organic molecule, having a Ki for inhibition of PDE10 that is less than or about one-hundredth that for a substance that is an inhibitor for another PDE enzyme. In other words, the organic molecule inhibits PDE10 activity to the same degree at a concentration of about one-hundredth or less than the concentration required for any other PDE enzyme. A "selective PDE10 inhibitor" can be identified, for example, by comparing the ability of an organic molecule to inhibit PDE10 activity to its ability to inhibit PDE enzymes from the other PDE families. For example, an organic molecule may be assayed for its ability to inhibit PDE10 activity, as well as PDE1A, PDE1B, PDE1C, PDE2A, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, and/or PDE11A.

Phosphodiesterase enzymes including PDE10 have been implicated in a wide range of biological functions. This has suggested a potential role for these enzymes in a variety of disease processes in humans or other species. The compounds of the present invention have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention may provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temperal dementia, delirium, amnestic disorders or age related cognitive decline.

In another specific embodiment, compounds of the present invention may provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention may provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention may provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention may provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with post-partum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders. In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain. In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Assay:

The activity of the compounds in accordance with the present invention as PDE10 inhibitors may be readily determined without undue experimentation using a fluorescence polarization (FP) methodology that is well known in the art (Huang, W., et al., *J. Biomol Screen*, 2002, 7: 215). In particular, the compounds of the following examples had activity in reference assays by exhibiting the ability to inhibit the hydrolysis of the phosphate ester bond of a cyclic nucleotide. Any compound exhibiting a Ki (inhibitory constant) below 1 µM would be considered a PDE10 inhibitor as defined herein.

In a typical experiment the PDE10 inhibitory activity of the compounds of the present invention was determined in accordance with the following experimental method. PDE10A2 was amplified from human fetal brain cDNA (Clontech, Mountain View, Calif.) using a forward primer corresponding to nucleotides 56-77 of human PDE10A2 (Accession No. AF127480, Genbank Identifier 4894716), containing a Kozak consensus sequence, and a reverse primer corresponding to nucleotides 2406-2413 of human PDE10A2 (Accession No. AF127480, Genbank Identifier 4894716). Amplification with Easy-A polymerase (Stratagene, La Jolla, Calif.) was 95° C. for 2 minutes followed by thirty three cycles of 95° C. for 40 seconds, 55° C. for 30 seconds, and 72° C. for 2 minutes 48 seconds. Final extension was 72° C. for 7 minutes. The PCR product was TA cloned into pcDNA3.2-TOPO (Invitrogen, Carlsbad, Calif.) according to standard protocol. AD293 cells with 70-80% confluency were transiently transfected with human PDE10A2/pcDNA3.2-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES, 1 mM EDTA and protease inhibitor cocktail (Roche). Lysate was collected by centrifugation at 75,000×g for 20 minutes. Supernatant containing the cytoplasmic fraction was used for evaluation of PDE10A2 activity. The fluorescence polarization assay for cyclic nucleotide phosphodiesterases was performed using an IMAP® FP kit supplied by Molecular Devices, Sunnyvale, Calif. (product #R8139). IMAP® technology has been applied previously to phosphodiesterase assays (Huang, W., et al., *J. Biomol Screen*, 2002, 7: 215). Assays were performed at room temperature in 384-well microtiter plates with an incubation volume of 20.2 µL. Solutions of test compounds were prepared in DMSO and serially diluted with DMSO to yield 8 µL of each of 10 solutions differing by 3-fold in concentration, at 32 serial dilutions per plate. 100% inhibition is determined using a known PDE10 inhibitor, which can be any compound that is present at 5,000 times its Ki value in the assay described as follows, such as papaverine (see Siuciak, et al. *Neuropharmacology* (2006) 51:386-396; Becker, et al. *Behav Brain Res* (2008) 186(2):155-60; Threlfell, et al., *J Pharmacol Exp Ther* (2009) 328(3):785-795), 2-[4-[pyridin-4-yl-1-(2,2,2-trifluoroethyl)-1H-pyrazol-3-yl]phenoxymethyl]quinoline succinic acid or 2-[4-(1-methyl-4-pyridin-4-yl-1H-pyrazol-3-yl)-phenoxymethyl]quinoline succinic acid (see Schmidt, et al. *J Pharmacol Exp Ther* (2008) 325:681-690; Threlfell, et al., *J Pharmacol Exp Ther* (2009) 328(3): 785-795). 0% of inhibition is determined by using DMSO (1% final concentrations). A Labcyte Echo 555 (Labcyte, Sunnyvale, Calif.) is used to dispense 200 nL from each well of the titration plate to the 384 well assay plate. A solution of enzyme (1/7000 dilution from aliquots; sufficient to produce 20% substrate conversion) and a separate solution of FAM-labeled cAMP PDE from Molecular Devices (product #R7506), at a final concentration of 50 nM are made in the assay buffer (10 mM Tris HCl, pH 7.2, 10 mM MgCl$_2$, 0.05% NaN$_3$ 0.01% Tween-20, and 1 mM DTT). The enzyme is added to the assay plates by the addition of 10 µL of enzyme solution to each well, shaken to mix and incubated at room temperature for 60 minutes. The substrate is then added to the assay plates by the addition of 10 uL of substrate solution to each well, shaken to mix, and incubated at room temperature for 60 minutes. A binding solution is then made from the kit components, comprised of 80% Solution A, 20% Solution B and binding reagent at a volume of 1/600 the total binding solution. The enzymatic reaction is stopped by addition of 60 µL of the binding solution to each well of the assay plates and the plates are sealed and shaken for 10 seconds. The plate was incubated at room temperature for at least one hour prior to determining the fluorescence polarization (FP). The parallel and perpendicular fluorescence of each well of the plate was measured using a Perkin Elmer EnVision™ plate reader (Waltham, Mass.). Fluorescence polarization (mP) was calculated from the parallel (S) and perpendicular (P) fluorescence of each sample well and the analogous values for the median control well, containing only substrate (So and Po), using the following equation:

Polarization $(mP)=1000*(S/So-P/Po)/(S/So+P/Po)$.

Dose-inhibition profiles for each compound were characterized by fitting the mP data to a four-parameter equation given below. The apparent inhibition constant ($K_I$), the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., *JALA*, 2003, 8: 54-63, using the following equation:

$$mP = \frac{(0\%\ mP - 100\%\ mP)(I\max - I\min)}{1 + \left[\frac{[\text{Drug}]}{\left(10^{-pK_I}\left(1 + \frac{[\text{Substrate}]}{K_M}\right)\right)}\right]^{nH}} +$$

$$100\%\ mP + (0\%\ mP - 100\%\ mP)(1 - I\max)$$

The median signal of the "0% inhibition controls" (0% mP) and the median signal of the "100% inhibition controls" (100% mP) are constants determined from the controls located in columns 1-2 and 23-24 of each assay plate. An apparent ($K_m$) for FAM-labeled cAMP of 150 nM was determined in separate experiments through simultaneous variation of substrate and selected drug concentrations.

Selectivity for PDE10, as compared to other PDE families, was assessed using the IMAP® technology. Rhesus PDE2A3 and Human PDE10A2 enzyme was prepared from cytosolic fractions of transiently transfected HEK cells. Bovine PDE6 was isolated from bovine retinas by the procedure of Cook and Beavo (2000). All other PDE's were GST Tag human enzyme expressed in insect cells and were obtained from BPS Bioscience (San Diego, Calif.): PDE1A (Cat#60010), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product #R7506 or cGMP#R7508), at a final concentration of 50 nM were made in the assay buffer (10 mM Tris HCl, pH 7.2, 10 mM MgCl$_2$, 0.05% NaN$_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 μL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 μL of the binding solution to each well of the assay plate. The plates were sealed and shaken for 10 seconds. The plates were incubated at room temperature for one hour. The parallel and perpendicular fluorescence of each well of the plate was measured using a Perkin Elmer EnVision™ plate reader (Waltham, Mass.). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, rhesus PD2A3 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE10 inhibitory activity of a compound which may be used in accordance with the present invention may be determined by these assays.

The compounds of the following examples had activity in inhibiting the human PDE10 enzyme in the aforementioned assays, generally with a Ki of less than about 1 μM. Many of compounds within the present invention had activity in inhibiting the human PDE10 enzyme in the aforementioned assays, generally with a Ki of less than about 0.1 μM. Additional data are provided in the following Examples. Such a result is indicative of the intrinsic activity of the compounds in use as inhibitors of the PDE10 enzyme. In general, one of ordinary skill in the art would appreciate that a substance is considered to effectively inhibit PDE10 activity if it has a Ki of less than or about 1 μM, where more potent inhibitors have a Ki of less than or about 0.1 μM. The present invention also includes compounds within the generic scope of the invention which possess activity as inhibitors of other phosphodiesterase enzymes.

The subject compounds are further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, $5\text{-HT}_{1A}$ agonists or antagonists, especially $5\text{-HT}_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg. of body weight daily are administered to the patient, e.g., humans and elderly humans. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein.

The following abbreviations are used herein: Me: methyl; Et: ethyl; t-Bu: tert-butyl; Ar: aryl; Ph: phenyl; Bn: benzyl; Ac: acetyl; THF: tetrahydrofuran; Boc: tert-butyloxycarbonyl; DIAD: Diisopropyl azodicarboxylate; DIPEA: N,N-diisopropylethylamine; DPPA: diphenylphosphorylazide; EDC: N-(3-Dimethylaminopropyl)-N'-ethylcarbodiimide; EtOAc: ethyl acetate; HOBt: hydroxybenzotriazole hydrate; TEA: triethylamine; DMF: N,N-dimethylformamide; rt: room temperature; HPLC: high performance liquid chromatography; NMR: nuclear magnetic resonance; TLC: thin-layer chromatography.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

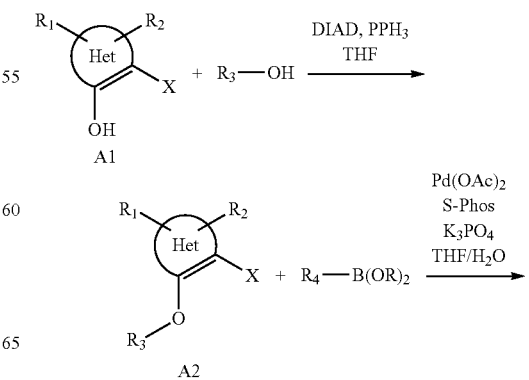

REACTION SCHEME A

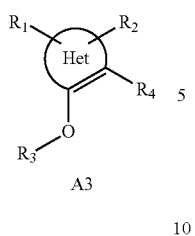

A3

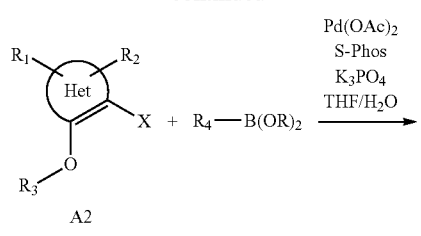

A2

REACTION SCHEME A-1

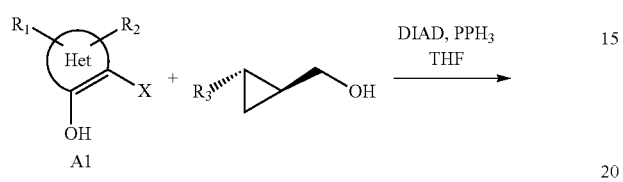

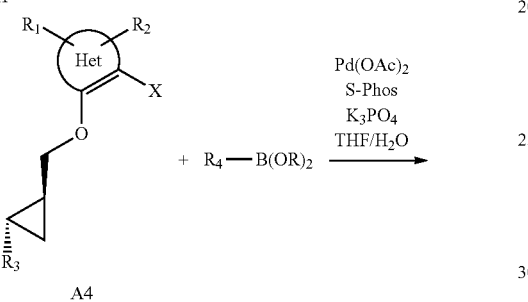

A4

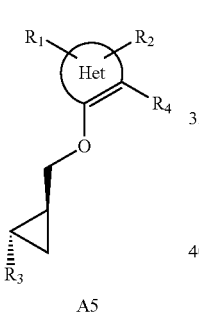

A5

REACTION SCHEME B-1

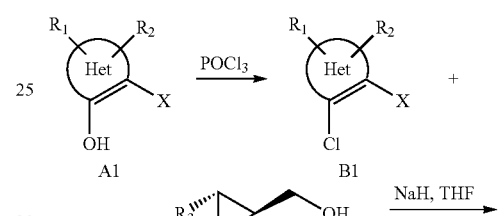

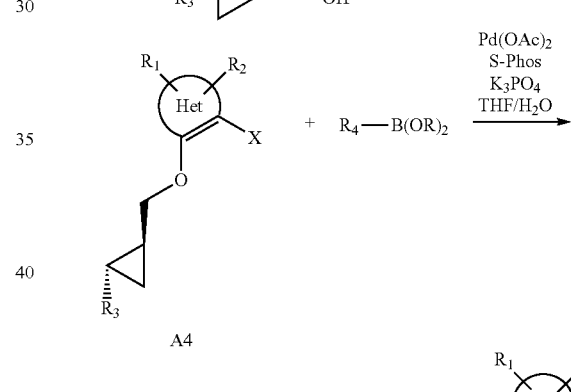

A4

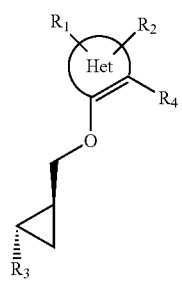

A5

A number of routes can be employed toward the synthesis of ortho-disubstituted aromatics. In the most straightforward case, ortho-disubstituted hydroxy-halo arenes of the form A1 readily undergo a Mitsunobu reaction with a variety of primary alcohols to furnish a separable mixture of O- and N-substituted compounds. With A2 or A4 in hand, a general and high-yielding Suzuki cross coupling reaction employing Pd(OAc)$_2$ and S-Phos furnishes the desired compounds, A3 and A5.

REACTION SCHEME B

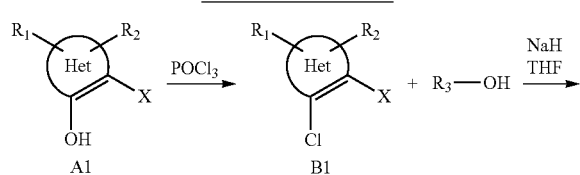

In a related synthetic sequence, ortho-disubstituted hydroxy-halo arenes of the form A1 can be chlorinated in near quantitative yields to afford dihaloarene B1, which can be used subsequently without further purification. A facile SNAr facilitates the installation of both primary and secondary alcohols, and avoids the issues of regioisomer separation, as in Reaction Schemes A and A-1. Typically, the products of this SNAr, A2 and A4, are sufficiently pure to be carried on to the subsequent step without further purification. Finally, a Pd-catalyzed Suzuki cross coupling furnishes the desired compounds, A3 and A5.

REACTION SCHEME C

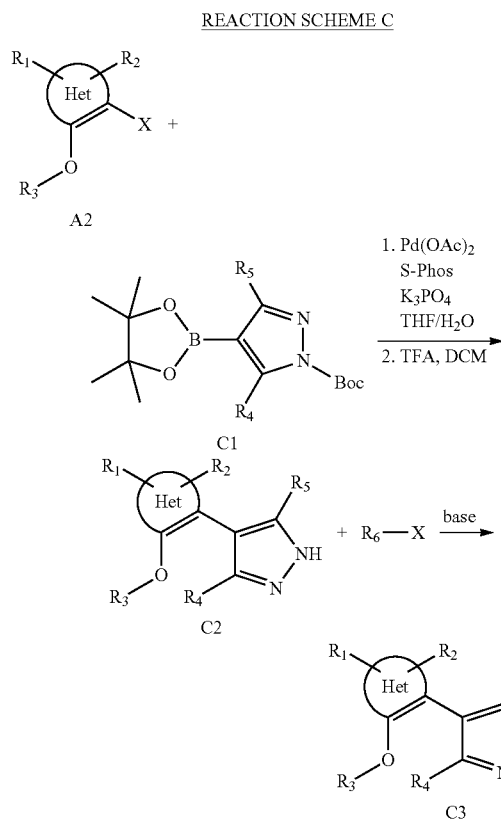

Variably functionlized pyrazole compounds of the form C3 can be accessed efficiently from A2. The synthetic sequence involves Suzuki cross coupling with commercially available boronate ester C1 followed by acid-mediated Boc deprotection to provide C2. Alkylation of C2 proceeds smoothly by the appropriate choice of either a kinetic (NaH) or thermodynamic ($K_2CO_3$) base, to afford the desired products.

REACTION SCHEME D

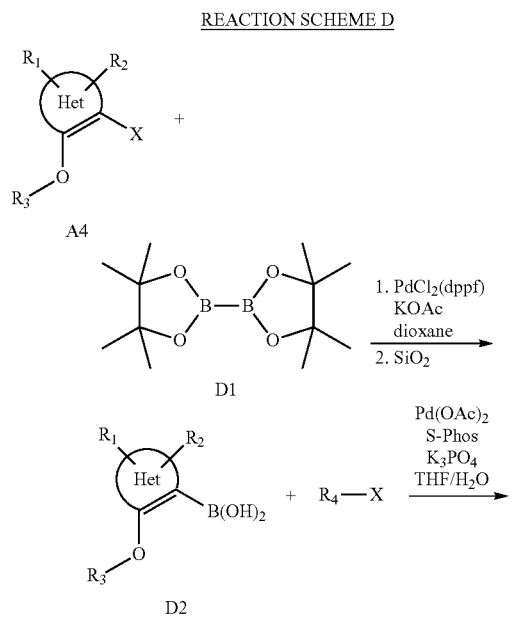

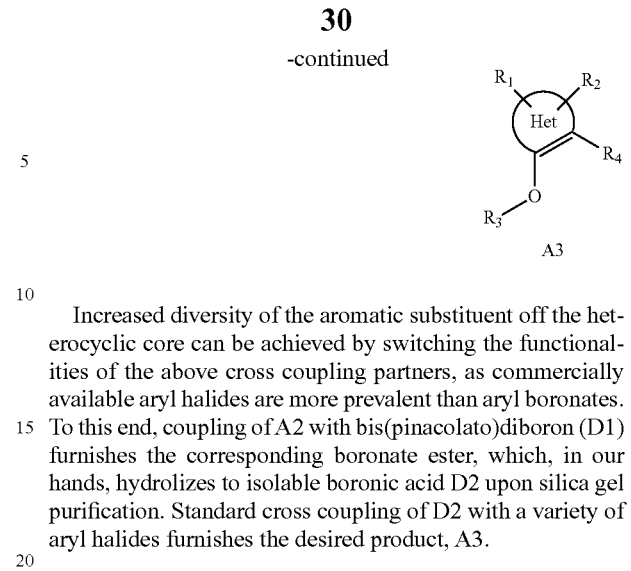

Increased diversity of the aromatic substituent off the heterocyclic core can be achieved by switching the functionalities of the above cross coupling partners, as commercially available aryl halides are more prevalent than aryl boronates. To this end, coupling of A2 with bis(pinacolato)diboron (D1) furnishes the corresponding boronate ester, which, in our hands, hydrolizes to isolable boronic acid D2 upon silica gel purification. Standard cross coupling of D2 with a variety of aryl halides furnishes the desired product, A3.

REACTION SCHEME E

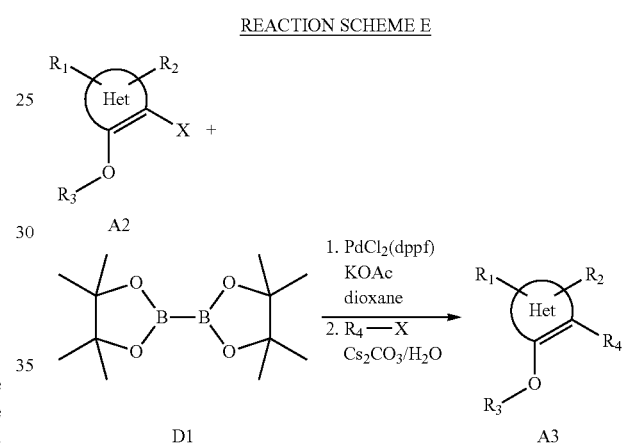

The above sequence was subsequently optimized to provide a 2-step/1-pot protocol for coupling of aryl halide A2 with other aryl halides. Treatment of A2 with bis(pinacolato)diboron in the presence of $PdC_2$(dppf), followed by addition of an aryl halide and aqueous $Cs_2CO_3$ to the in situ-generated boronate ester in the reaction pot provides A3 directly in moderate to good yields.

REACTION SCHEME F

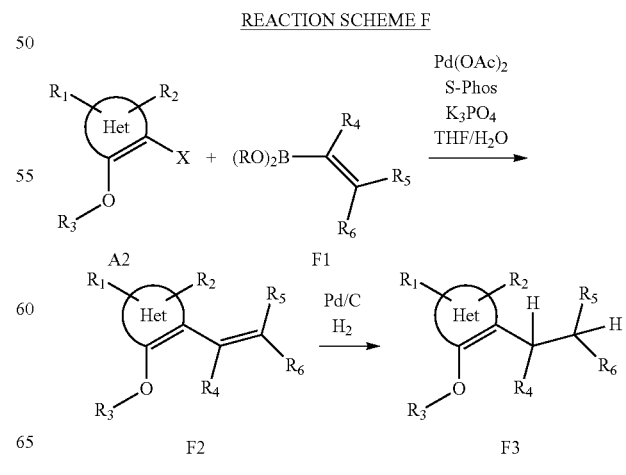

Cyclic and acyclic saturated and unsaturated substitution can be installed ortho to the alkoxy linkage in one of several ways. As shown above, cyclic and acyclic alkenyl boronates undergo facile Suzuki cross coupling with haloarenes A2 to provide unsaturated compounds F2. Subsequent Pd-catalyzed hydrogenation furnishes the fully reduced compounds F3.

REACTION SCHEME G

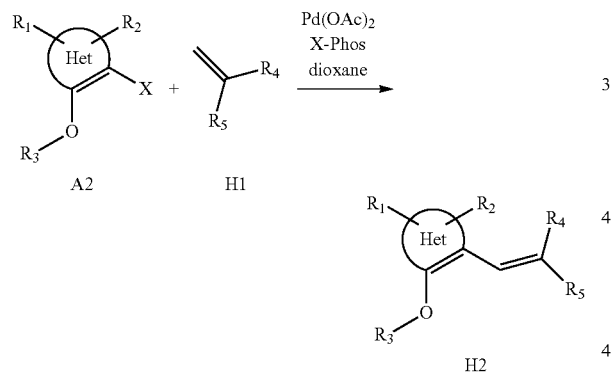

In an alternate route, alkyltrifluoroborates undergo Pd-catalyzed Suzuki cross coupling with haloarenes A2 in the presence of the cataCXium A ligand.

REACTION SCHEME H

In an alternate route, vinyl arenes undergo Pd-catalyzed Heck cross coupling with haloarenes A2 in the presence of the X-Phos ligand to afford exclusively the trans diastereomer of desired product H2.

REACTION SCHEME I

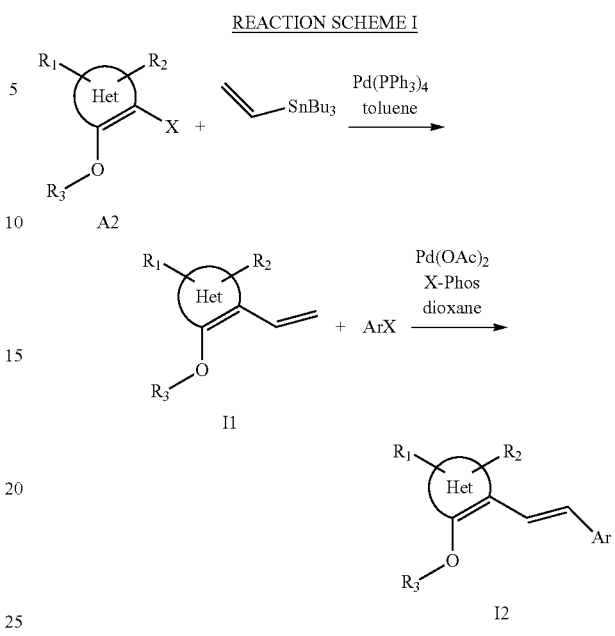

In an alternate route, vinyltributyl tin undergoes Pd-catalyzed Stille cross coupling with haloarenes A2 to afford vinyl compound H. This compound then undergoes a Pd-catalyzed trans-selective Heck cross coupling with haloarenes to provide I2.

REACTION SCHEME J

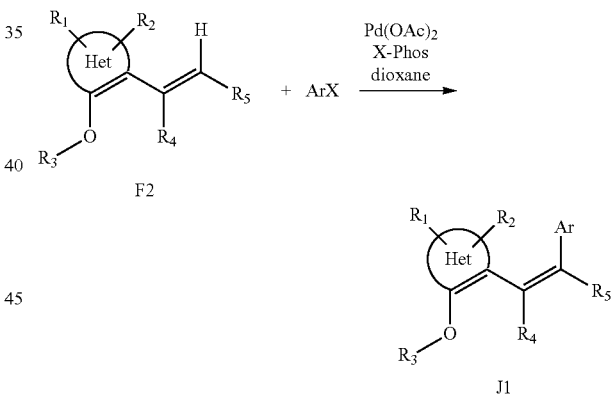

In a final alternate route, F2 undergoes a Pd-catalyzed Heck cross coupling with haloarenes to provide J1.

REACTION SCHEME K

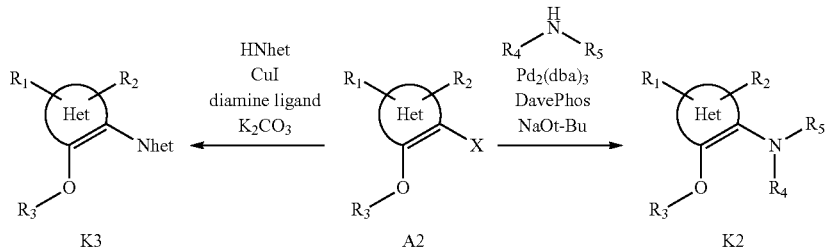

Amine substitution ortho to the alkoxy linkage can be installed through standard C—N cross coupling. C—N cross coupling between haloarene A2 and aliphatic amines proceeds in the presence of Pd$_2$(dba)$_3$ and DavePhos to provide amino compounds of the form K2. Similarly, C—N cross coupling between haloarene A2 and N—H heterocycles proceeds in the presence of CuI and a diamine ligand to provide amino compounds of the form K3.

Variation of the functionality at the 2-position of a pyrimidine backbone is achieved in a three-step sequence beginning with commercially available trihaloarene L1. A facile SNAr reaction with variably functionalized alcohols furnishes intermediate L2, which undergoes a Pd-catalyzed Suzuki cross coupling under standard conditions to provide key intermediate L3.

REACTION SCHEME M

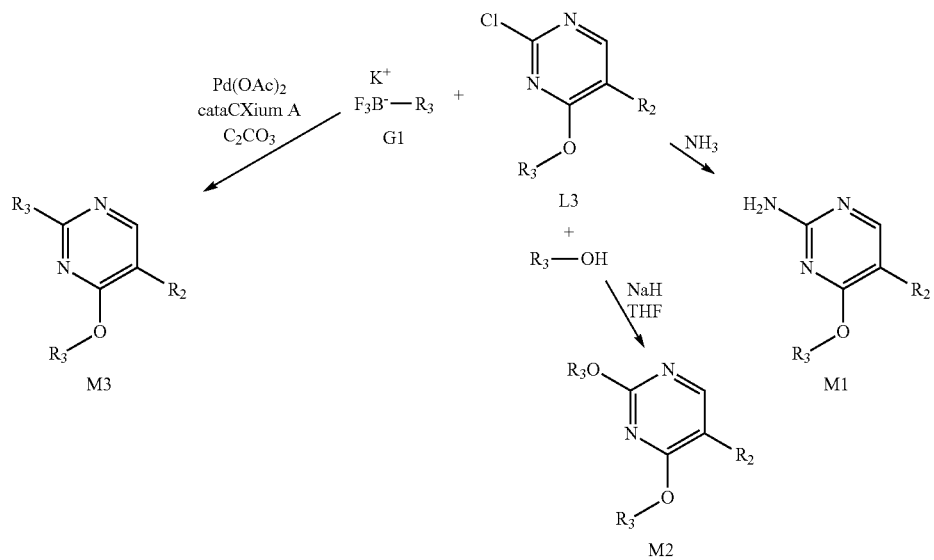

L3 can subsequently undergo a second SNAr reaction to afford either amino compound M3 or alkoxy compound M2. L3 can also undergo a Pd-catalyzed Suzuki cross coupling with either alkyl or aryl trifluoroborates to afford carbon-substituted compounds of the form M3.

REACTION SCHEME L

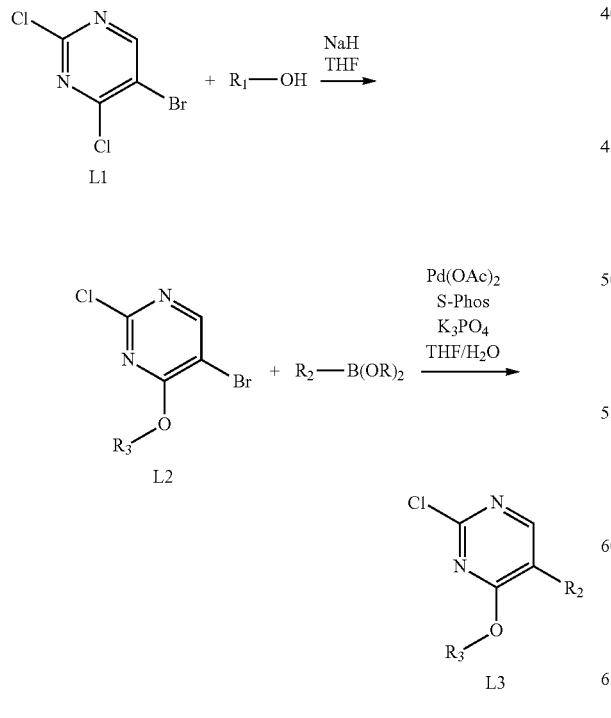

REACTION SCHEME N

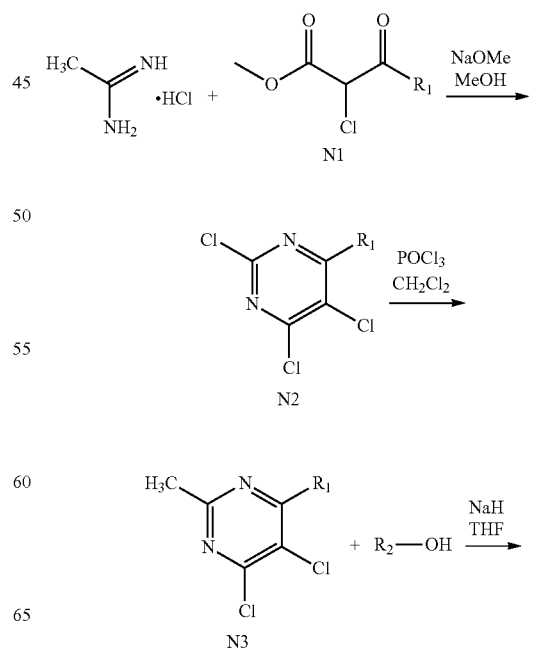

-continued

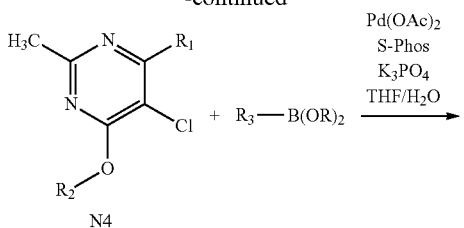

N4

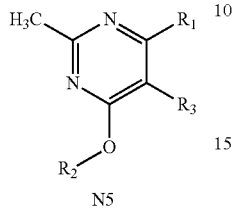

N5

Variation of the functionality at the 4-position of a pyrimidine backbone is achieved in a four-step sequence. Condensation of acetamidine hydrochloride with chloro ketoester N1 under basic conditions furnishes hydroxy dichloropyrimidine N2. The synthesis is completed using the previously described sequence involving chlorination to N3, SNAr to N4, and Pd-catalyzed cross coupling to final compounds N5.

REACTION SCHEME O

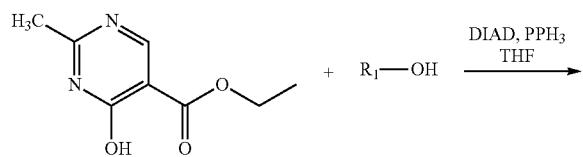

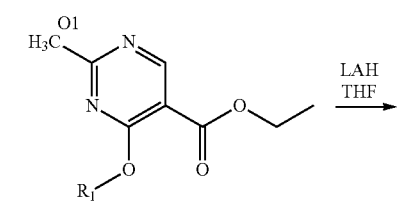

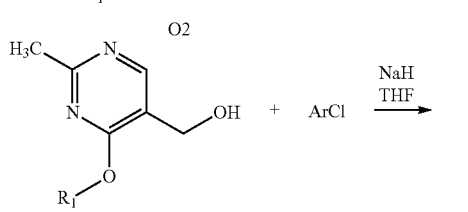

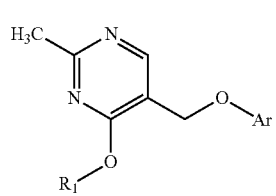

Alkylether functionality ortho to the alkoxy linkage can be accessed beginning with commercially available (Astatech, Inc., CAS#53135-24-3) hydroxy ester pyrimidine O1. A standard Mitsonobu reaction furnishes alkoxy compound O2. Complete reduction of the ester group provides alcohol O3, which can undergo a standard SNAr with chloroarenes to provide compounds of the form O4.

REACTION SCHEME P

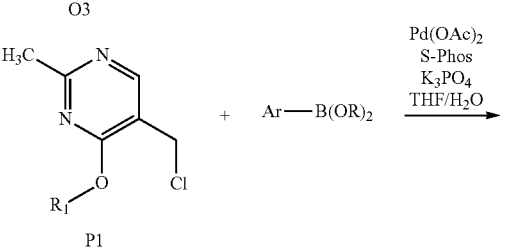

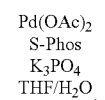

Alcohol O3 also serves as an intermediate toward all-carbon substituted compounds of the form P2. Chlorination of O3 under standard conditions furnishes benzylic chloride P1, which undergoes facile Pd-catalyzed sp$^2$-sp$^3$ cross coupling with boronates to provide P2.

REACTION SCHEME Q

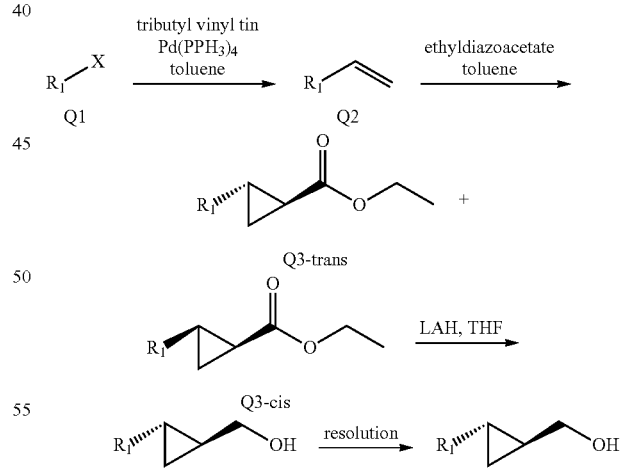

A number of routes can be employed toward the synthesis of hydroxymethyl cyclopropanes of the form Q5. In the most versatile route, a haloarene (Q1) can undergo a facile Stille cross coupling with tributyl vinyl tin under standard conditions to afford vinylarenes Q2. The terminal vinyl group is subsequently cyclopropanated with ethyl diazoacetate to afford a readily separable mixture of trans and cis cyclopropanes Q3, with the trans diastereomer typically predominating. At this point, the enantiomers of the trans cyclopropane can be resolved by preparative chiral chromatography. Alternatively, the ester functionality can be reduced under standard conditions to afford alcohol Q4, which can subsequently be resolved by preparative chiral chromatography.

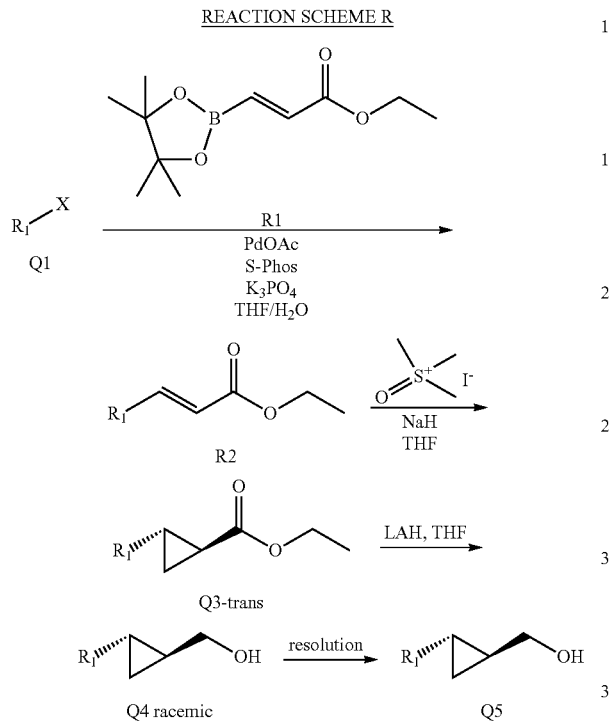

In an alternative route to alcohols Q5, haloarenes (Q1) can undergo Suzuki cross coupling with commercially available vinyl boronate ester R1 (Frontier Scientific, CAS#1009307-13-4) to afford E-acrylate R2. Treatment of R2 with trimethyl sulfoxonium iodide and NaH affords the desired trans cyclopropane Q3 in moderate to good yields. Following the protocol outlined in Reaction Scheme Q, the racemic ester can be converted to enantiopure alcohol Q5.

In yet another route to alcohols Q5, aryl aldehydes (S1) can undergo a Horner-Wadsworth-Emmons olefination with triethyl phosphonoacetate under standard conditions to afford E-acrylate R2. Following the protocols outlined in Reaction Schemes Q and R, the acrylate can be converted to enantiopure alcohol Q5.

PREPARATIVE EXAMPLE 1 trans ethyl 2-(pyridin-2-yl)cyclopropanecarboxylate (AA1-trans)

A solution of 2-vinylpyridine (2 g, 19.02 mmol) in toluene (40 mL) was treated with ethyl diazoacetate (1.973 ml, 19.02 mmol) and stirred at reflux overnight. The mixture was concentrated in vacuo and the residue was purified by gradient elution on silica gel (0 to 50% EtOAc in hexanes) to elute peak 1; the solvent gradient was then ramped to 100% EtOAc to elute peak 2. This yielded the title compound (1.6 g, 44%) as the first eluting diastereomer, and the corresponding cis diastereomer (914 mg, 25%) as the second eluting diastereomer, both as yellow oils. Data for trans stereoisomer: $^1$H NMR δ (500 MHz, CDCl$_3$): 8.44 (m, 1H), 7.56 (td, J=7.6, 1.7

Hz, 1H), 7.22 (dd, J=7.8, 1.0 Hz, 1H), 7.08 (ddd, J=7.6, 4.9, 1.2 Hz, 1H), 4.17 (q, J=7.3 Hz, 2H), 2.58 (ddd, J=10.0, 6.1, 3.9 Hz, 1H), 2.25 (ddd, J=9.5, 5.6, 3.9 Hz, 1H), 1.61, (m, 2H), 1.28 (t, J=7.1 Hz, 3H). LRMS (ES) calculated M+H for C11H13NO2S: 192.2. Found: 192.1. Enantiomers can be resolved by chiral preparative SFC (3.0 cm i.d.×25 cm ChiralTech IC, 7% EtOH/CO$_2$, 70 mL/min) and analyzed by chiral analytical SFC (4.6 mm i.d.×25 cm ChiralTech IC, 7% EtOH/CO$_2$, 2.4 mL/min) ent$_1$=3.6 min, ent$_2$=4.1 min.

trans 2-(pyridin-2-yl)cyclopropyl]methanol (AA2)

A solution of AA1-trans (751 mg, 3.93 mmol) in THF (20 mL) was cooled to 0° C. and treated slowly with lithium aluminum hydride (3.93 mL, 3.93 mmol, 1 M solution in THF). The solution was warmed to room temperature and stirred for 20 min. The reaction mixture was then re-cooled to 0° C. and treated sequentially dropwise with 0.15 mL of water, 0.15 ml of 15% NaOH, and 0.45 mL of water. Sodium sulfate was added to the mixture. After stirring at room temperature for 10 min, the mixture was filtered through a pad of Celite and the filtrate was concentrated in vacuo to afford the title compound as a pale yellow oil. The material was sufficiently pure to use in the subsequent step without further purification. $^1$H NMR (500 MHz, CDCl$_3$): δ 8.41 (d, J=4.2 Hz, 1H), 7.52 (td, J=7.6, 1.7 Hz, 1H), 7.10 (d, J=7.8 Hz, 1H), 7.03 (ddd, J=7.3, 4.9, 0.7 Hz, 1H), 3.72 (dd, J=11.2, 6.4 Hz, 1H), 3.57 (dd, J=11.2, 7.1 Hz, 1H), 2.26 (bs, 1H), 1.98 (m, 1H), 1.74 (m, 1H), 1.25 (m, 1H), 0.96 (m, 1H) ppm; LRMS (ES) calculated M+H for C$_9$H$_{11}$NO: 150.2. Found: 150.1. As an alternate means to resolving enantiomers of this building block, enantiomers of AA2 could be resolved by chiral preparative SFC (3.0 cm i.d.×25 cm ChiralPak AD-H, 3:7:90 MeCN/MeOH/CO$_2$, 70 mL/min) and analyzed by chiral analytical SFC (4.6 mm i.d.×25 cm ChiralPak AD-H, 3:7:90 MeCN/MeOH/CO$_2$, 2.4 mL/min) ent$_1$=7.5 min, ent$_2$=8.4 min.

PREPARATIVE EXAMPLE 2

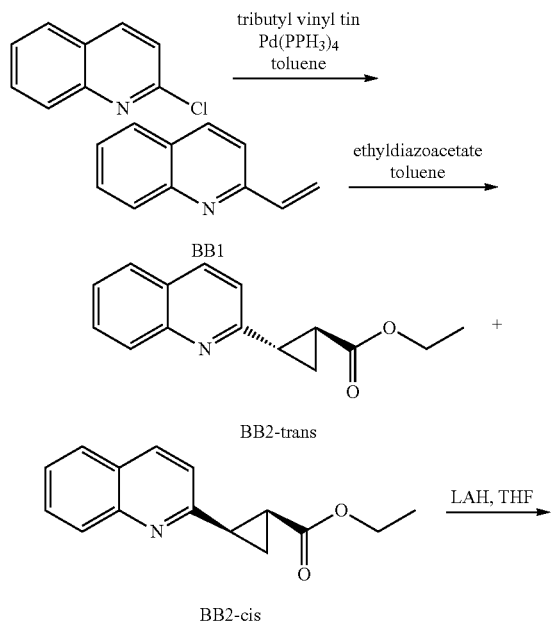

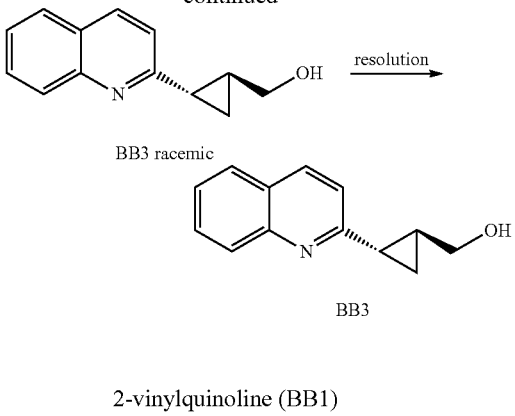

2-vinylquinoline (BB1)

A solution of 2-chloroquinoline (1 g, 6.11 mmol) and vinyl tributyl tin (2.69 mL, 9.17 mmol) in toluene (30 mL) was treated with Pd(PPh$_3$)$_4$ (0.706 g, 0.611 mmol) and heated to reflux for 1.5 h. The reaction mixture was concentrated and the resulting material was purified directly by gradient elution on silica gel (0 to 25% EtOAc in hexanes) to afford the title compound as a colorless oil (941 mg, 99%). All spectral data matched literature values.[1] LRMS m/z (M+H) 156.1 found, 156.2 required.

([1] Fakhfakh, M. A.; Franck, X.; Fournet, A.; Hocquemiller, R.; Figadère, B. Tetrahedron Lett. 2001, 42, 3847.)

ethyl 2-(quinolin-2-yl)cyclopropanecarboxylate (BB2-trans)

A solution of BB1 (941 mg, 6.06 mmol) in toluene (20 ml) was treated with ethyl diazoacetate (0.629 mL, 6.06 mmol) and stirred at reflux overnight. The mixture was concentrated and the residue was purified by gradient elution on silica gel (0 to 30% EtOAc in hexanes) to elute peak 1 (trans diastereomer). The eluent was then ramped up (50% EtOAc in hexanes) to elute peak 2 (cis diastereomer). This afforded the title compound as a pale yellow oil (706 mg, 40%, ca. 70% pure), which could be used in the subsequent step without further purification. LRMS m/z (M+H) 242.2 found, 242.3 required.

2-(quinolin-2-yl)cyclopropyl]methanol (BB3)

A solution of the BB2-trans (200 mg, 0.829 mmol) in THF (20 mL) was cooled to 0° C. and treated slowly with a 1M THF solution of LiAlH$_4$ (0.829 mL, 0.829 mmol). The solution was warmed to room temperature and stirred for 20 min. The mixture was re-cooled to 0° C. and treated dropwise with 0.03 mL of water, 0.03 ml of 15% NaOH, and 0.09 mL of water successively. Sodium sulfate was added to the mixture, and after stirring at room temperature for 10 min, the mixture was filtered through Celite, eluting exhaustively with CH$_2$Cl$_2$ and MeOH. The filtrate was concentrated in vacuo, and the resulting residue was purified by gradient elution on silica gel (0 to 100% EtOAc in hexanes) to afford the title compound as a colorless oil (130 mg, 79%). $^1$H NMR (500 MHz, CDCl$_3$): δ 7.93 (d, J=3.5 Hz, 1 H), 7.90 (d, J=3.5 Hz, 1 H), 7.67 (d, J=8.1 Hz, 1H), 7.59 (td, J=7.6, 1.4 Hz, 1 H), 7.38 (td, J=7.6, 1.0 Hz, 1 H), 7.09 (d, J=8.5 Hz, 1 H), 3.76 (dd, J=11.4, 6.0 Hz, 1H), 3.56 (dd, J=11.4, 7.2 Hz, 1H), 2.15 (dt, J=8.5, 4.4 Hz, 1H), 1.84 (m, 1H), 1.33 (dt, J=8.6, 4.4 Hz, 1H), 1.01 (ddd, J=10.4, 5.9, 1.1 Hz, 1H) ppm; LRMS m/z (M+H) 200.1 found, 200.2 required. Enantiomers were resolved by chiral preparative SFC (3.0 cm i.d.×25 cm ChiralPak AD-H, 30% MeOH/CO$_2$+0.1% DEA, 70 mL/min) and analyzed by chiral analytical SFC (4.6 mm i.d.×25 cm ChiralPak AD-H, 30% MeOH/CO$_2$+0.1% DEA, 2.4 mL/min) ent$_1$=2.8 min, ent$_2$=3.5 min.

PREPARATIVE EXAMPLE 3

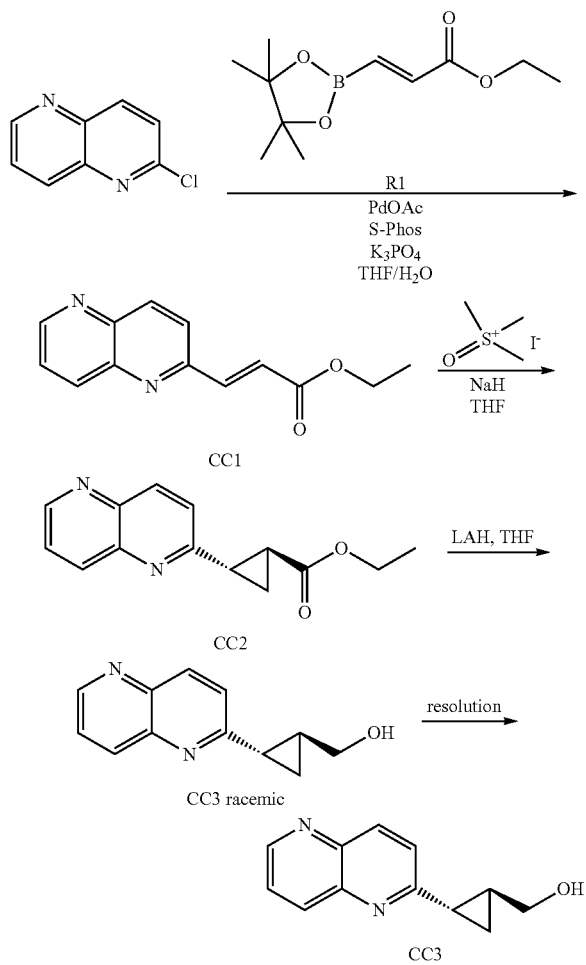

ethyl 3-(1,5-naphthyridin-2-yl)prop-2-enoate (CC1)

2-chloro-1,5-naphthyridine (101 mg, 0.614 mmol), boronate ester R1 (195 mg, 0.920 mmol), S-Phos (25.2 mg, 0.061 mmol), K$_3$PO$_4$ (391 mg, 1.841 mmol) and PdOAc$_2$ (6.89 mg, 0.031 mmol) were combined in a 5-mL microwave vial in THF (2.5 mL) and water (500 µl). The reaction mixture was heated at 100° C. for 15 min. The reaction mixture was diluted with EtOAc (20 mL), washed with sat. aq. NaHCO$_3$ (25 mL) and brine (25 mL), dried over MgSO$_4$, filtered, and concentrated in vacuo. The resulting residue was purified by gradient elution on silica gel (10 to 100% EtOAc in hexanes) to afford the title compound as a pale orange solid (118 mg, 90%). $^1$H NMR (500 MHz, DMSO): δ 9.02 (dd, J=4.1, 1.6 Hz, 1 H), 8.48 (d, J=8.8 Hz, 1 H), 8.48-8.42 (m, 1 H), 8.25 (d, J=8.7 Hz, 1 H), 7.84-7.79 (m, 2 H), 7.13 (d, J=16.0 Hz, 1 H), 4.25 (q, J=7.1 Hz, 2 H), 1.30 (t, J=7.1 Hz, 3 H) ppm; LRMS m/z (M+H) 229.2 found, 229.1 required.

ethyl 2-(1,5-naphthyridin-2-yl)cyclopropanecarboxylate (CC2)

To a 5-mL sealed vial was added trimethyl sulfoxonium iodide (170 mg, 0.770 mmol), DMSO (2567 µl), and NaH (26.7 mg, 0.668 mmol). This mixture was stirred for 40 min at 50° C. The reaction mixture was then cooled to room temperature and to it was added a solution of CC1 (110 mg, 0.513 mmol) in DMSO (1.5 mL). The reaction mixture was stirred at room temperature for 5 min, and then diluted with EtOAc (75 mL) and washed with sat. aq. NaHCO$_3$ (4×20 mL). The organics were dried over MgSO$_4$, filtered, and concentrated in vacuo. The resulting residue was purified by gradient elution on silica gel (20 to 100% EtOAc in hexanes) to afford the title compound (67 mg, 57%). $^1$H NMR (500 MHz, CDCl$_3$): δ 8.89 (dd, J=4.2, 1.6 Hz, 1H), 8.28 (d, J=8.6 Hz, 1H), 8.23 (d, J=8.6 Hz, 1H), 7.60-7.57 (m, 2H), 4.20 (q, J=7.1 Hz, 2H), 2.82-2.77 (m, 1H), 2.47-2.42 (m, 1H), 1.79 (ddd, J=8.6, 6.0, 3.8 Hz, 1H), 1.71 (ddd, J=8.9, 5.6, 3.8 Hz, 1H), 1.29 (t, J=7.2 Hz, 3H) ppm; LRMS m/z (M+H) 243.3 found, 243.3 required.

[2-(1,5-naphthyridin-2-yl)cyclopropyl]methanol (CC3)

The title compound was prepared on a 1.1-gram (3.86 mmol) scale from CC2 according to the protocol outlined in Example 1, to afford the title compound as a brown gum (750 mg, 97%). $^1$H NMR (500 MHz, CDCl$_3$): δ 8.86 (dd, J=4.2, 1.6 Hz, 1H), 8.21-8.26 (m, 2H), 7.57 (dd, J=8.5, 4.2 Hz, 1H), 7.44 (d, J=8.7 Hz, 1H), 3.77 (dd, J=11.3, 6.3 Hz, 1H), 3.68 (dd, J=11.3, 6.9 Hz, 1H), 2.21 (dt, J=8.6, 4.5 Hz, 1H), 1.99-1.92 (m, 1H), 1.48-1.42 (m, 1H), 1.16-1.10 (m, 1H); LRMS m/z (M+H) 201.3 found, 201.2 required. Enantiomers were resolved by chiral preparative SFC (3.0 cm i.d.×25 cm ChiralPak AD-H, 30% MeOH/CO$_2$+0.1% DEA, 70 mL/min) and analyzed by chiral analytical SFC (4.6 mm i.d.×25 cm ChiralPak AD-H, 30% MeOH/CO$_2$+0.1% DEA, 2.4 mL/min) ent$_1$=3.4 min, ent$_2$=4.7 min.

PREPARATIVE EXAMPLE 4

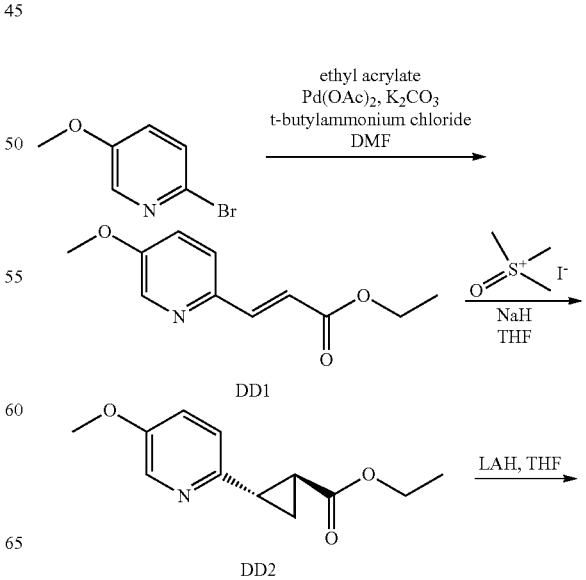

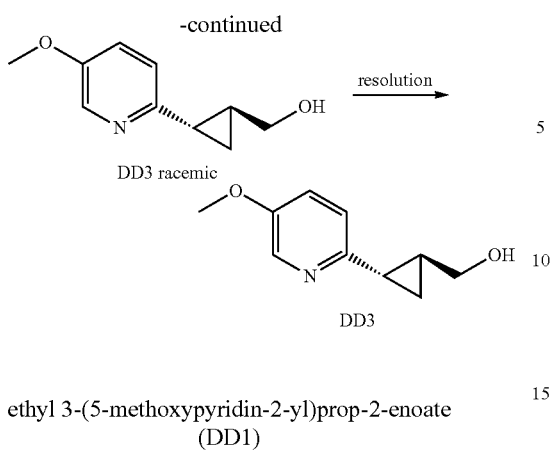

ent₁=3.7 min, ent₂=4.4 min. Enantiomer 2 was determined to correspond to the active enantiomer, and was employed in subsequent chemistry.

PREPARATIVE EXAMPLE 5

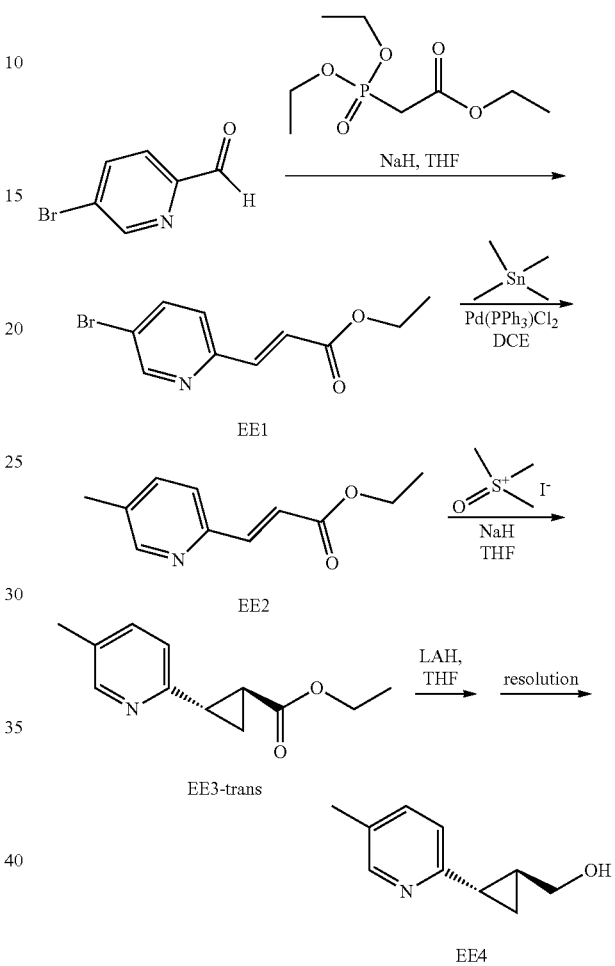

ethyl 3-(5-methoxypyridin-2-yl)prop-2-enoate (DD1)

To a 25-mL microwave vial was added 2-bromo-5-methoxy pyridine (1.88 g, 10 mmol), ethyl acrylate (5.44 ml, 50.0 mmol), Pd(OAc)₂ (0.225 g, 1.000 mmol), K₂CO₃ (4.15 g, 30.0 mmol), and t-butylammonium chloride hydrate (2.96 g, 10.00 mmol). The slurry was heated in the microwave at 160° C. for 1 h. Upon cooling to room temperature, the mixture was diluted with EtOAc (100 mL) and washed with sat. aq. NaHCO3 (100 mL). The aqueous layer was extracted with additional EtOAc (2×50 mL). The combined organic layers were then washed with water and brine, dried over Na₂SO₄, filtered, and concentrated in vacuo. The resulting residue was purified by gradient elution on silica gel (0 to 50% EtOAc in hexanes) to afford the title compound (1.5 g, 72%). ¹H NMR (500 MHz, CDCl₃): δ 8.35 (d, J=3.0 Hz, 1H), 7.65 (d, J=15.7 Hz, 1H), 7.38 (d, J=8.6 Hz, 1H), 7.18 (dd, J=8.6, 3.0 Hz, 1H), 6.76 (d, J=15.7 Hz, 1H), 4.26 (q, J=7.1 Hz, 2H), 3.89 (s, 3H), 1.33 (t, J=7.1 Hz, 3H) ppm; LRMS m/z (M+H) 208.0 found, 208.2 required.

ethyl 2-(5-methoxypyridin-2-yl)cyclopropanecarboxylate (DD2)

The title compound was prepared on a 1-gram (4.83 mmol) scale according to the protocol outlined in Example 2 for compound CC2. The product was obtained as a light yellow solid (500 mg, 47%). ¹H NMR (500 MHz, CDCl₃): δ 8.15 (d, J=2.9 Hz, 1H), 7.14 (d, J=8.0 Hz, 1H), 7.10 (dd, J=8.0, 2.9 Hz, 1H), 4.16 (q, J=7.1 Hz, 2H), 3.82 (s, 3H), 2.58-2.52 (m, 1H), 2.18-2.12 (m, 1H), 1.56 (m, 1H), 1.54 (m, 1H), 1.27 (t, J=7.1 Hz, 3H) ppm; LRMS m/z (M+H) 222.3 found, 222.3 required.

[2-(5-methoxypyridin-2-yl)cyclopropyl]methanol (DD3)

The title compound was prepared on a 0.36-gram (1.63 mmol) scale from DD2 according to the protocol outlined in Example 1, to afford the title compound as a light yellow oil (290 mg, 99%). ¹H NMR (500 MHz, CDCl₃): δ 8.14 (d, J=2.9 Hz, 1H), 7.09 (dd, J=8.6, 2.9 Hz, 1H), 7.04 (d, J=8.6 Hz, 1H), 3.82 (s, 3H), 3.72-3.66 (m, 1H), 3.61-3.55 (m, 1H), 1.97-1.91 (m, 1H), 1.69-1.62 (m, 1H), 1.20-1.14 (m, 1H), 0.91 (1H, dt, J=8.71, 5.06 Hz) ppm; LRMS m/z (M+H) 180.1 found, 180.1 required. Enantiomers were resolved by chiral preparative SFC (3.0 cm i.d.×25 cm ChiralPak AD-H, 6.7/13.3/80 MeCN/MeOH/CO₂, +0.1% DEA, 70 mL/min) and analyzed by chiral analytical SFC (4.6 cm i.d.×25 cm ChiralPak AD-H, 6.7/13.3/80 MeCN/MeOH/CO₂, +0.1% DEA, mL/m)

(E)-ethyl 3-(5-bromopyridin-2-yl)acrylate (EE1)

To a stirred solution of triethyl phosphonoacetate (10.9 mL, 55.0 mmol) in THF (65 mL) was added sodium hydride (2.20 g, 55.0 mmol) dissolved in THF (10 mL) dropwise at room temperature. The resulting mixture was stirred for 30 minutes at room temperature. To this mixture was added a solution of 5-bromopicolinaldehyde (9.30 g, 50.0 mmol) dissolved in THF (10 mL) with vigorous stirring. The reaction was stirred for 1 hour, partitioned between ethyl acetate and saturated ammonium chloride solution. The organic phase was washed with brine, dried over sodium sulfate, and concentrated. The crude material was flash column separated using a 0-20% ethyl acetate/hexane gradient to give title compound (10.3 g, 80%). LRMS (ES) (M+H)⁺: observed=256.1/258.1, calculated=256.1/258.1.

(E)-ethyl 3-(5-methylpyridin-2-yl)acrylate (EE2)

To a stirred solution of EE1 (1.64 g, 6.40 mmol) and trimethyltin (1.06 mL, 7.68 mmol) in dichloroethane (32 mL)

under nitrogen was added Pd(PPh$_3$)$_2$Cl$_2$ (0.45 g, 0.64 mmol) and the resulting mixture was heated to 150° C. overnight. The reaction was partitioned between water and dichloromethane. The organic phase washed with brine, dried over sodium sulfate, and concentrated. The crude material was flash column separated using a 0-25% ethyl acetate/hexane gradient to give title compound (0.73 g, 60%). LRMS (ES) (M+H)$^+$: observed=192.1, calculated=192.2.

ethyl 2-(5-methylpyridin-2-yl)cyclopropanecarboxylate (EE3-trans)

The title compound was prepared from EE2 according to the protocol outlined in Example 4 to afford EE3-trans. LRMS (ES) (M+H)$^+$: observed=206.2, calculated=206.2.

2-(5-methylpyridin-2-yl)cyclopropyl)methanol (EE4)

The title compound was prepared from EE3-trans according to the protocol outlined in Example 1 to afford EE4 as a solid. LRMS (ES) (M+H)$^+$: observed=164.1, calculated=164.2.

PREPARATIVE EXAMPLE 6

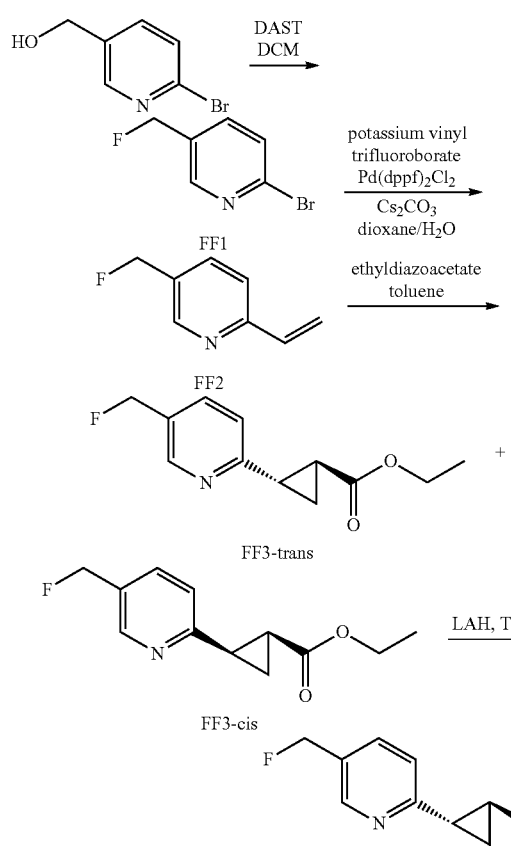

2-bromo-5-(fluoromethyl)pyridine (FF1)

To a stirred solution of (6-bromopyridin-3-yl)methanol (1.00 g, 5.32 mmol) in dichloromethane (25 mL) at 0° C. was added DAST (0.70 mL, 5.32 mmol) and the resulting solution was stirred at 0° C. for one hour. The mixture was washed with a saturated sodium bicarbonate solution and concentrated. Flash column separation using a 0-10% ethyl acetate/hexane gradient gave FF1 (0.37 g, 37%). LRMS (ES) (M+H)$^+$: observed=190.0/192.0, calculated=190.0/192.0.

5-(fluoromethyl)-2-vinylpyridine (FF2)

To a stirred solution of FF1 (1.09 g, 5.74 mmol) and potassium vinyl trifluoroborate (1.54 g, 11.47 mmol) in dioxane (9.75 mL) under nitrogen was added Pd(dppf)$_2$Cl$_2$ (0.47 g, 0.57 mmol), cesium carbonate (5.61 g, 17.21 mmol), and water (1.72 mL). The resulting mixture heated to 100° C. for 90 minutes. The reaction was partitioned between ethyl acetate and saturated sodium bicarbonate solution. The organic phase was concentrated and flash column separation using a 0-15% ethyl acetate/hexane gradient gave FF2 as an oil (0.53 g, 67%). LRMS (ES) (M+H)$^+$: observed=138.0, calculated=138.1.

ethyl 2-(5-(fluoromethyl)pyridin-2-yl)cyclopropanecarboxylate (FF3-trans)

The title compound was prepared from FF2 according to the protocol outlined in Example 1, carried through as the trans racemate without chiral resolution, to afford FF3-trans as a brown oil. LRMS (ES) (M+H)$^+$: observed=224.2, calculated=224.2.

2-(5-(fluoromethyl)pyridin-2-yl)cyclopropyl)methanol (FF4)

The title compound was prepared from F-3-trans according to the protocol outlined in Example 1 to afford FF4 as a yellow oil. LRMS (ES) (M+H)$^+$: observed=182.2, calculated=182.2.

PREPARATIVE EXAMPLE 7

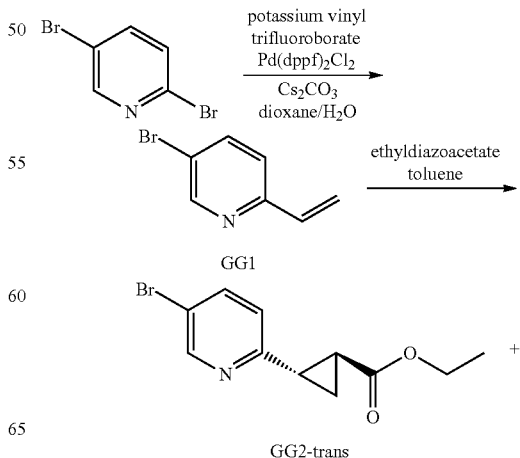

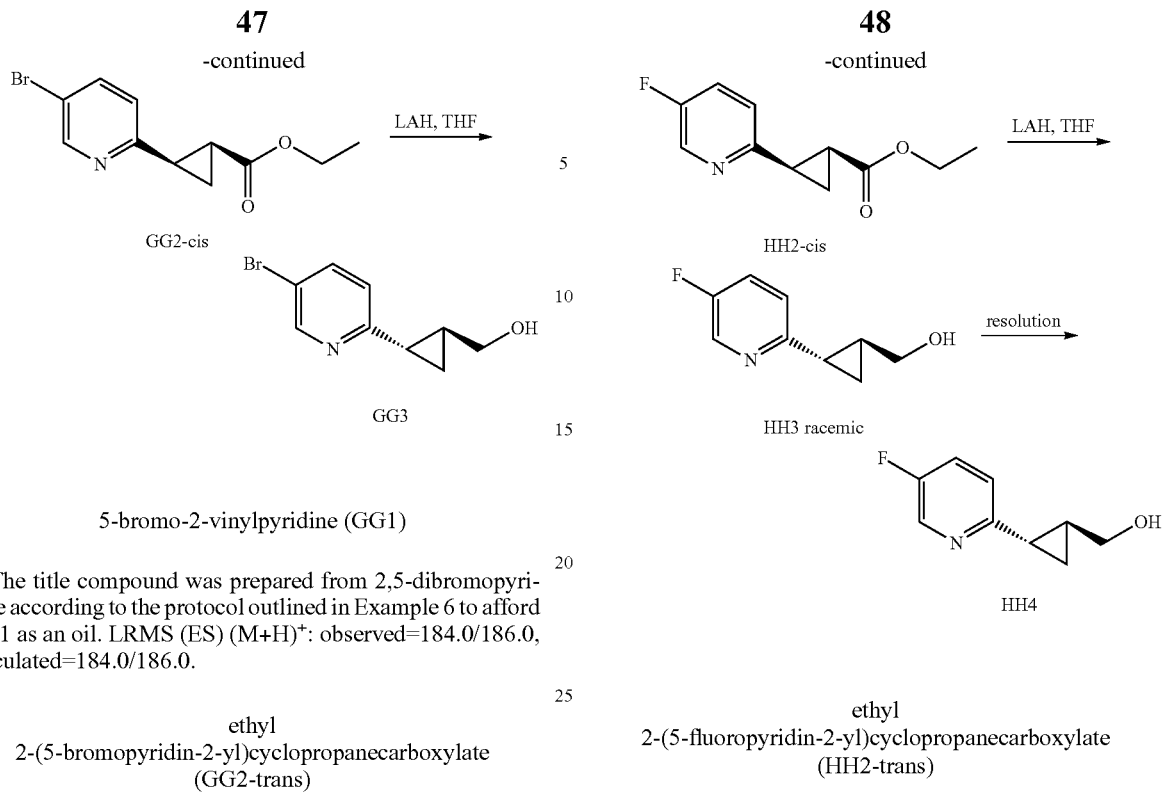

5-bromo-2-vinylpyridine (GG1)

The title compound was prepared from 2,5-dibromopyridine according to the protocol outlined in Example 6 to afford GG1 as an oil. LRMS (ES) (M+H)$^+$: observed=184.0/186.0, calculated=184.0/186.0.

ethyl 2-(5-bromopyridin-2-yl)cyclopropanecarboxylate (GG2-trans)

The title compound was prepared from GG1 according to the protocol outlined in Example 1, carried through as the trans racemate without chiral resolution, to afford GG2-trans as an oil. LRMS (ES) (M+H)$^+$: observed=270.1/272.1, calculated=270.1/272.1.

2-(5-bromopyridin-2-yl)cyclopropyl)methanol (GG3)

The title compound was prepared from GG2-trans according to the protocol outlined in Example 1 to afford GG3 as an oil. LRMS (ES) (M+H)$^+$: observed=228.1/230.1, calculated=228.1/230.1.

PREPARATIVE EXAMPLE 8

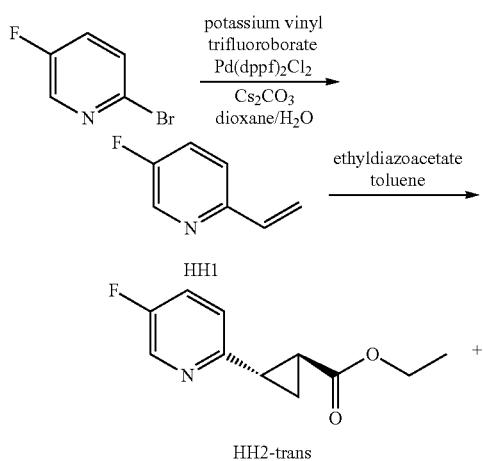

ethyl 2-(5-fluoropyridin-2-yl)cyclopropanecarboxylate (HH2-trans)

2-bromo-5-fluoropyridine was used to prepare HH1 according to the protocol outlined in Example 6. HH1 was used directly to prepare the title compound according to the protocol outlined in Example 1 to afford HH2-trans as an oil. LRMS (ES) (M+H)$^+$: observed=210.2, calculated=210.2.

2-(5-fluoropyridin-2-yl)cyclopropyl)methanol (HH4)

The title compound was prepared from HH2-trans according to the two-step protocol outlined in Example 1 to afford HH4 as an oil. LRMS (ES) (M+H)$^+$: observed=168.0, calculated=168.2.

PREPARATIVE EXAMPLE 9

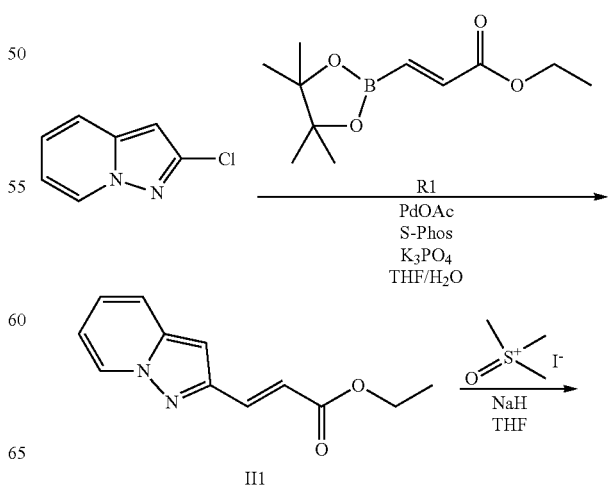

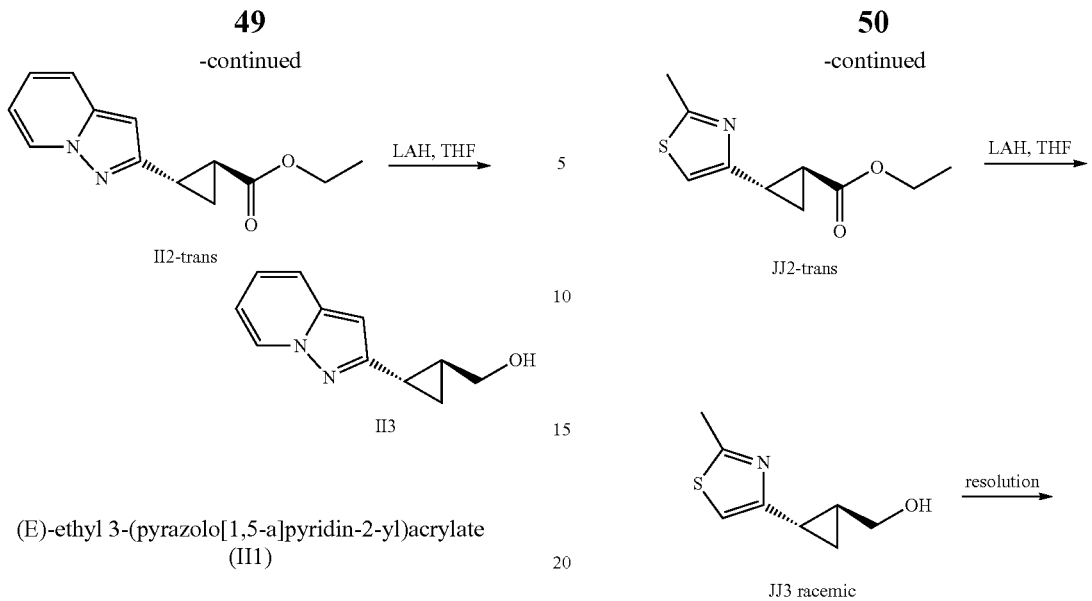

(E)-ethyl 3-(pyrazolo[1,5-a]pyridin-2-yl)acrylate (II1)

The title compound was prepared from 2-chloropyrazolo [1,5-a]pyridine according to the protocol outlined in Example 3 to afford II1 as a solid. LRMS (ES) (M+H)$^+$: observed=203.2, calculated=203.2.

ethyl 2-(pyrazolo[1,5-a]pyridin-2-yl)cyclopropanecarboxylate (II2-trans)

The title compound was prepared from II1 according to the protocol outlined in Example 3, carried through as the trans racemate without chiral resolution to afford II2-trans as a solid. LRMS (ES) (M+H)$^+$: observed=217.1, calculated=217.2.

2-(pyrazolo[1,5-a]pyridin-2-yl)cyclopropy)methanol (II3)

The title compound was prepared from II2-trans according to the protocol outlined in Example 1, to afford II3 as an oil. LRMS (ES) (M+H)$^+$: observed=189.2, calculated=189.2.

PREPARATIVE EXAMPLE 10

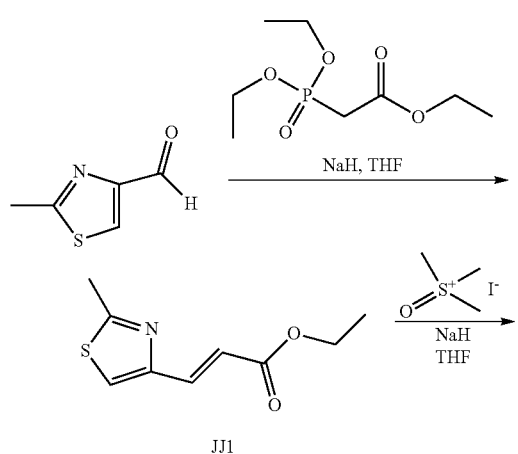

ethyl 3-(2-methylthiazol-4-yl)acrylate (JJ-1)

To a stirred solution of sodium hydride (1.04 g, 26.0 mmol) in THF (47.2 mL) was added triethyl phosphonoacetate (5.19 mL, 26.0 mmol) portionwise at room temperature. The resulting mixture was stirred for 30 minutes at room temperature. To this mixture was added a solution of 2-methylthiazole-4-carbaldehyde (3.0 g, 23.6 mmol) dissolved in THF (30 mL) with vigorous stirring. The reaction was stirred for 1 hour, partitioned between ethyl acetate and saturated sodium bicarbonate solution. The organic phase was washed with brine, dried over sodium sulfate, and concentrated to give the title compound as a yellow oil (4.3 g, 92%). LRMS (ES) (M+H)$^+$: observed=198.1, calculated=198.2.

ethyl 2-(2-methylthiazol-4-yl)cyclopropanecarboxylate (JJ2-trans)

The title compound was prepared from JJ1 according to the protocol outlined in Example 3 to afford JJ2-trans. LRMS (ES) (M+H)$^+$: observed=212.2, calculated=212.2.

2-(2-methylthiazol-4-yl)cyclopropyl)methanol (JJ4)

The title compound was prepared from JJ2-trans according to the protocol outlined in Example 1 to afford JJ4 as a solid. LRMS (ES) (M+H)$^+$: observed=170.1, calculated=170.2.

PREPARATIVE EXAMPLE 11

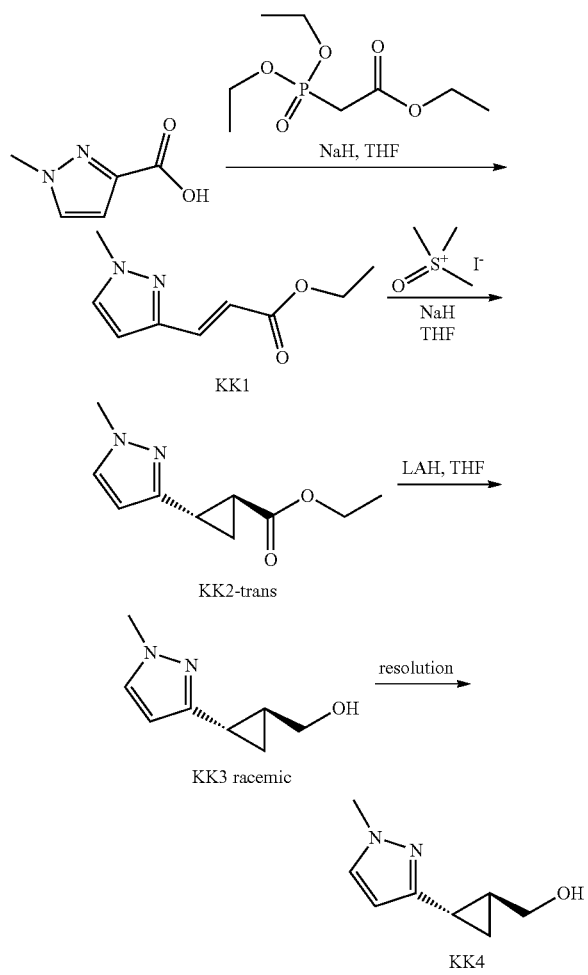

EXAMPLE 1-1

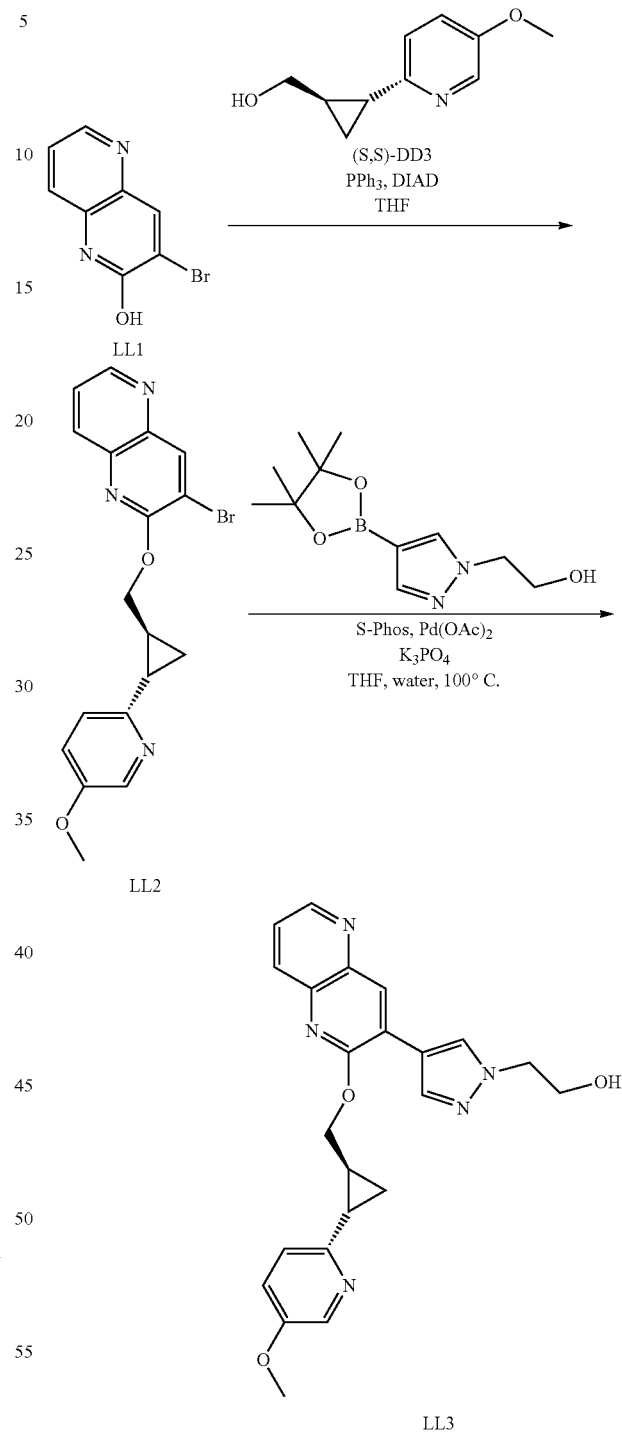

ethyl 2-(1-methyl-1H-pyrazol-3-yl)cyclopropanecarboxylate (KK2-trans)

The title compound was prepared from 1-methyl-1H-pyrazole-3-carbaldehyde according to the protocol outlined in Example 10 to afford KK1. This was carried on without purification KK2-trans, as outlined in Example 3. KK2-trans was isolated as an oil. LRMS (ES) (M+H)$^+$: observed=195.3, calculated=195.2.

2-(1-methyl-1H-pyrazol-3-yl)cyclopropyl)methanol (KK4)

The title compound was prepared from KK2-trans according to the protocol outlined in Example 1 to afford KK3 as a solid. LRMS (ES) (M+H)$^+$: observed=153.2, calculated=153.2.

3-bromo-2-{[(1S,2S)-2-(5-methoxypyridin-2-yl)cyclopropyl]methoxy}-1,5-naphthyridine (LL2)

To a solution of 3-bromo-1,5-naphthyridin-2-ol (LL1) (1.5 g, 6.7 mmol) in THF (33.5 mL) at 0° C. was added triphenylphosphine (2.1 g, 8.0 mmol) and (1S,2S)-2-(5-methoxypyridin-2-yl)cyclopropyl]methanol (S,S-DD3, ent$_2$) (1.2 g, 6.7 mmol), followed by dropwise addition of DIAD (1.6 mL, 8 mmol). The reaction mixture was warmed to ambient temperature. After 10 minutes, the reaction mixture was concentrated and the resulting residue was purified by flash chromatography (20% to 100% EtOAc in hexanes) to afford the title compound as a yellow solid. $^1$H NMR (500 MHz, DMSO): δ 8.82 (d, J=4.2 Hz, 1 H), 8.67 (s, 1 H), 8.21 (d, J=8.5 Hz, 1 H), 8.13 (d, J=2.5 Hz, 1 H), 7.73 (dd, J=8.5, 4.2 Hz, 1 H), 7.26 (d, J=3.5 Hz, 2 H), 4.53 (d, J=7.0 Hz, 2 H), 3.78 (s, 3 H), 2.25 (dt, J=8.5, 4.6 Hz, 1 H), 1.87-1.81 (m, 1 H), 1.18 (dt, J=8.7, 4.5 Hz, 1 H), 1.13-1.07 (m, 1 H); LRMS m/z (M+H) 386.3 found, 386.2 required.

2-[4-(2-{[(1S,2S)-2-(5-methoxypyridin-2-yl)cyclopropyl]methoxy}-1,5-naphthyridin-3-yl)-1H-pyrazol-1-yl]ethanol (LL3)

A mixture of 3-bromo-2-{[(1S,2S)-2-(5-methoxypyridin-2-yl)cyclopropyl]-methoxy}-1,5-naphthyridine (LL2) (130 mg, 0.3 mmol), 2-[4-(4,4,5,5-tetramethyl-1,3,2-dioxaborolan-2-yl)-1H-pyrazol-1-yl]ethanol (97 mg, 0.4 mmol), tripotassium phosphate (133 mg, 0.6 mmol), S-Phos (12.8 mg, 0.03 mmol), and Pd(OAc)$_2$ (3.5 mg, 0.02 mmol) in THF (1.3 mL) and water (0.3 mL) was heated at 100° C. for 14 hours. The reaction mixture was allowed to cool to room temperature. The mixture was then diluted with EtOAc (10 mL), washed with sodium bicarbonate (2 mL) and brine (2 mL), dried over MgSO$_4$, filtered and concentrated in vacuo. The resulting residue was purified by reverse phase chromatography (Waters Sunfire Prep C18 OBD, 5-60% acetonitrile in water with 0.1% TFA modifier) to afford the title compound as a white solid. $^1$H NMR (500 MHz, DMSO): δ 8.78 (d, J=4.1 Hz, 1 H), 8.55 (s, 1 H), 8.35 (s, 1 H), 8.22 (s, 1 H), 8.15-8.10 (m, 2 H), 7.61 (dd, J=8.4, 4.3 Hz, 1 H), 7.29 (s, 2 H), 4.94-4.91 (m, 1 H), 4.69-4.65 (m, 1 H), 4.47 (d, J=9.5 Hz, 1 H), 4.14-4.09 (m, 2 H), 3.79 (s, 3 H), 3.73 (d, J=6.5 Hz, 2 H), 2.31-2.27 (m, 1 H), 1.90 (s, 1 H), 1.26-1.22 (m, 1 H), 1.14 (s, 1H); HRMS m/z (M+H) 418.1871 found, 418.1874 required.

EXAMPLE 1-2

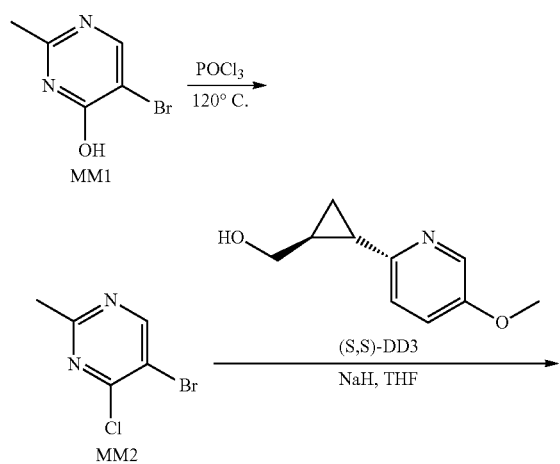

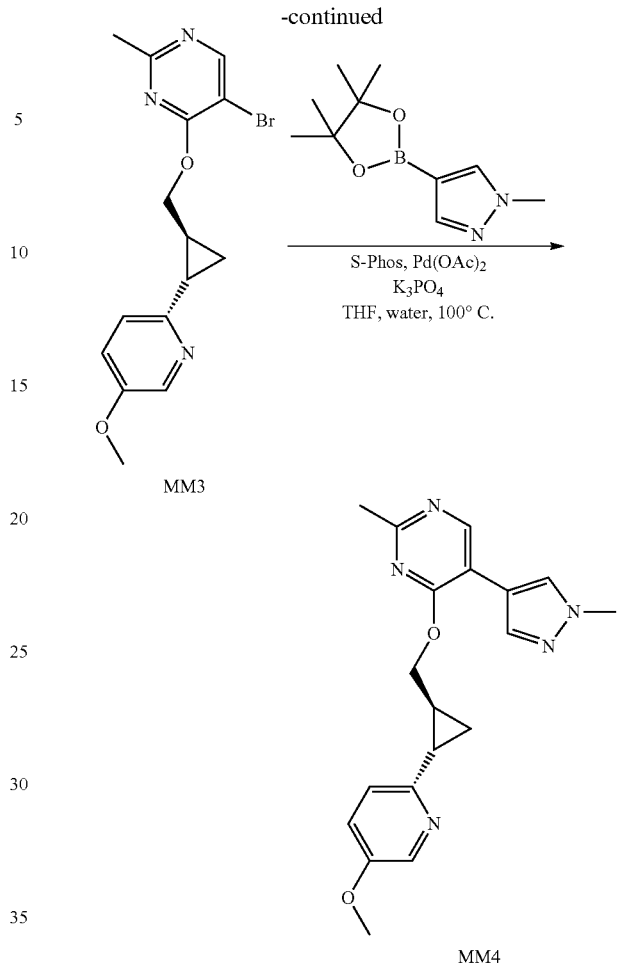

5-Bromo-4-chloro-2-methylpyrimidine (MM2)

5-Bromo-2-methylpyrimidin-4-ol (MM1) (30 g, 159 mmol) was suspended in phosphorous oxychloride (150 mL). The reaction mixture was heated at 120° C. for 30 minutes. The reaction mixture was cooled to ambient temperature, concentrated in vacuo and azeotroped twice with toluene. The crude residue was diluted with EtOAc (600 mL) and cooled to 0° C. Aqueous sodium bicarbonate (150 mL) was slowly added with stirring. The organic layer was washed once more with sodium bicarbonate (150 mL), dried over MgSO$_4$, filtered and concentrated in vacuo to afford the title compound as a dark oil, which was sufficiently pure to use in the subsequent step without further purification. LRMS m/z (M+H) 207.0 found, 207.4 required.

5-bromo-4-{[(1S,2S)-2-(5-methoxypyridin-2-yl)cyclopropyl]methoxy}-2-methylpyrimidine (MM3)

To a solution of [(1S,2S)-2-(5-methoxypyridin-2-yl)cyclopropyl]methanol (S,S-DD3, ent$_2$) (1.1 g, 6.1 mmol) in THF (25 mL) was added sodium hydride (300 mg, 7.4 mmol). The reaction mixture stirred at ambient temperature for 30 minutes. Next, a solution of 5-bromo-4-chloro-2-methylpyrimidine (MM2) (1.5 g, 7.4 mmol) in THF (5 mL) was added and the reaction mixture was stirred at ambient temperature for two hours. Aqueous sodium bicarbonate (20 mL) was carefully added and the mixture was extracted with EtOAc (2×50 mL). The combined organics were dried over MgSO$_4$, filtered and concentrated to afford the title compound as a yellow oil, which was sufficiently pure to use in the subsequent step without further purification. $^1$H NMR (500 MHz, DMSO): δ 8.60 (s, 1 H), 8.12 (d, J=3.0 Hz, 1 H), 7.30-7.22 (m, 2 H), 4.42 (d, J=7.1 Hz, 2 H), 3.78 (s, 3 H), 2.50 (s, 3 H), 2.19 (dt, J=8.6, 4.6 Hz, 1 H), 1.75 (s, 1 H), 1.14 (dt, J=8.8, 4.7 Hz, 1 H), 1.04 (dt, J=8.9, 4.7 Hz, 1 H); LRMS m/z (M+H) 350.3 found, 350.2 required.

4-{[(1S,2S)-2-(5-methoxypyridin-2-yl)cyclopropyl]methoxy}-2-methyl-5-(1-methyl-1H-pyrazol-4-yl)pyrimidine (MM4)

A mixture of 5-bromo-4-{[(1S,2S)-2-(5-methoxypyridin-2-yl)cyclopropyl]-methoxy}-2-methylpyrimidine (MM3) (400 mg, 1.1 mmol), 1-methyl-4-(4,4,5,5-tetramethyl-1,3,2-dioxaborolan-2-yl)-1H-pyrazole (420 mg, 2.0 mmol), tripotassium phosphate (600 mg, 2.8 mmol), S-Phos (46 mg, 0.1 mmol), and Pd(OAc)$_2$ (12.6 mg, 0.6 mmol) in THF (4.8 mL) and water (0.8 mL) was heated at 100° C. for 1 hour. The reaction mixture was allowed to cool to room temperature, and then diluted with EtOAc (10 mL), washed with sodium bicarbonate (2 mL) and brine (2 mL), dried over MgSO$_4$, filtered and concentrated. The resulting residue was purified by reverse phase chromatography (Waters Sunfire Prep C18 OBD, 5-45% acetonitrile in water with 0.1% TFA modifier) to afford the title compound as a colorless gum. $^1$H NMR (500 MHz, DMSO): δ 8.73 (s, 1 H), 8.14 (s, 1 H), 8.11 (s, 1 H), 7.97 (s, 1 H), 7.31-7.24 (m, 2 H), 4.54 (dd, J=11.2, 6.8 Hz, 1 H), 4.33 (dd, J=11.3, 7.7 Hz, 1 H), 3.82 (s, 3 H), 3.78 (s, 3 H), 2.50 (s, 3 H), 2.22 (dd, J=8.6, 4.7 Hz, 1 H), 1.79 (s, 1 H), 1.22-1.17 (m, 1 H), 1.10-1.05 (m, 1 H); HRMS m/z (M+H) 352.1761 found, 352.1768 required.

EXAMPLE 1-3

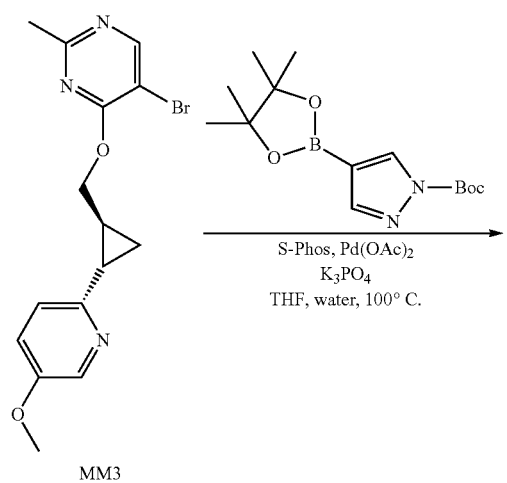

MM3

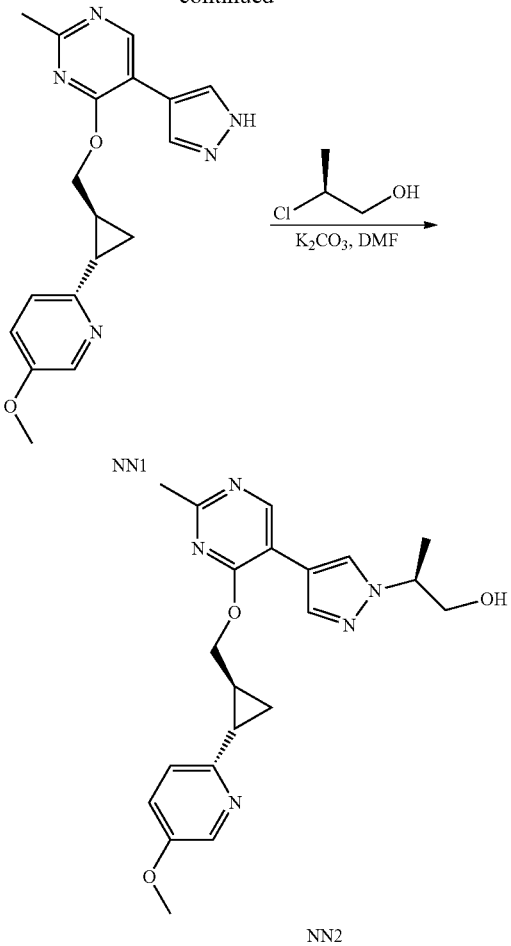

NN2

4-{[(1S,2S)-2-(5-methoxypyridin-2-yl)cyclopropyl]methoxy}-2-methyl-5-(1H-pyrazol-4-yl)pyrimidine (NN1)

A mixture of 5-bromo-4-{[(1S,2S)-2-(5-methoxypyridin-2-yl)cyclopropyl]-methoxy}-2-methylpyrimidine (MM3) (235 mg, 0.7 mmol), tert-butyl 4-(4,4,5,5-tetramethyl-1,3,2-dioxaborolan-2-yl)-1H-pyrazole-1-carboxylate (296 mg, 1.0 mmol), tripotassium phosphate (285 mg, 1.3 mmol), S-Phos (27.6 mg, 0.07 mmol), and Pd(OAc)$_2$ (7.5 mg, 0.03 mmol) in THF (3.0 mL) and water (0.5 mL) was heated at 100° C. for 14 hours. The reaction mixture was allowed to cool to room temperature. The mixture was then diluted with EtOAc (10 mL), washed with sodium bicarbonate (2 mL) and brine (2 mL), dried over MgSO$_4$, filtered and concentrated in vacuo. The resulting residue was purified by reverse phase chromatography (Waters Sunfire Prep C18 OBD, 5-45% acetonitrile in water with 0.1% TFA modifier) to afford the title compound as a white solid. $^1$H NMR (500 MHz, DMSO): δ 8.77 (s, 1 H), 8.15-8.13 (m, 2 H), 7.30-7.22 (m, 3 H), 4.50 (dd, J=11.2, 6.9 Hz, 1 H), 4.37 (dd, J=11.3, 7.5 Hz, 1 H), 3.78 (s, 3 H), 3.17 (d, J=5.3 Hz, 1 H), 2.50 (s, 3 H), 2.22 (dt, J=8.5, 4.6 Hz, 1 H), 1.79 (s, 1 H), 1.21-1.16 (m, 1 H), 1.07 (m, 1 H); LRMS m/z (M+H) 338.4 found, 338.2 required.

(2 S)-2-[4-(4-{[(1S,2S)-2-(5-methoxypyridin-2-yl)cyclopropyl]methoxy}-2-methylpyrimidin-5-yl)-1H-pyrazol-1-yl]propan-1-ol (NN2)

To a solution of 4-{[(1S,2S)-2-(5-methoxypyridin-2-yl)cyclopropyl]methoxy}-2-methyl-5-(1H-pyrazol-4-yl)pyrimidine (NN1) (15 mg, 0.04 mmol) in DMF (0.4 mL) was added and (2S)-2-chloropropan-1-ol (9.0 mg, 0.09 mmol) and potassium carbonate (18.4 mg, 0.13 mmol). The reaction mixture was stirred at ambient temperature for 14 hours. The mixture was filtered and purified by reverse phase chromatography (Waters Sunfire Prep C18 OBD, 5-45% acetonitrile in water with 0.1% TFA modifier) to afford the title compound as a white solid. $^1$H NMR (500 MHz, DMSO): δ 8.74 (s, 1 H), 8.13 (d, J=11.7 Hz, 2 H), 8.00 (s, 1 H), 7.27 (d, J=7.1 Hz, 2 H), 4.55-4.50 (m, 1 H), 4.37-4.30 (m, 1 H), 3.96 (s, 3 H), 3.78 (s, 3 H), 2.50 (s, 3 H), 2.22 (d, J=7.1 Hz, 1 H), 1.80 (s, 1 H), 1.25-1.16 (m, 2 H), 1.07 (m, 1 H), 1.01 (d, J=5.3 Hz, 3 H); HRMS m/z (M+H) 396.2019 found, 396.2030 required.

EXAMPLE 1-4

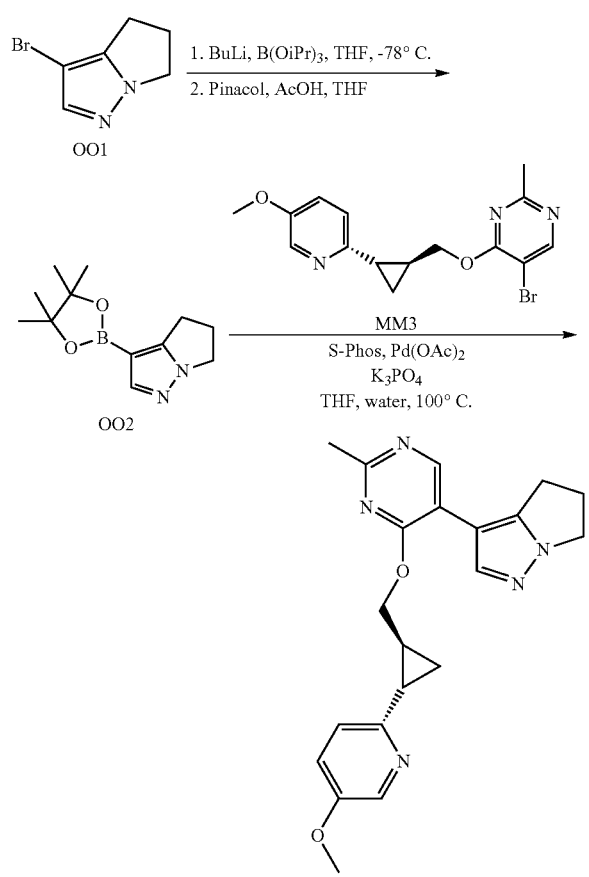

3-(4,4,5,5-tetramethyl-1,3,2-dioxaborolan-2-yl)-5,6-dihydro-4H-pyrrolo[1,2-b]pyrazole (OO2)

To a solution on 3-bromo-5,6-dihydro-4H-pyrrolo[1,2-b]pyrazole (OO1) (73.5 g, 390 mmol) in THF (600 mL) was slowly added a solution on n-BuLi (300 mL, 1.6 M in THF) at −78° C. The resulting mixture was allowed to stir at the same temperature for 45 minutes. A solution of triisopropylborate (111 mL, 480 mmol) was then added and the mixture was allowed to warm up to ambient temperature and stirred for an additional hour. A solution of pinacol (63.8 g, 540 mmol) in THF (300 mL) was then added. After five minutes, a solution of acetic acid (24 mL, 420 mmol) was added and the reaction mixture was stirred for 30 minutes. The reaction mixture was filtered through Celite and washed with sodium bicarbonate, extracted with EtOAc (2×500 mL), dried over MgSO$_4$, filtered and concentrated. The crude residue was purified by column chromatography to afford the title compound as a white solid. $^1$H NMR (500 MHz, DMSO): δ 7.55 (s, 1 H), 4.04 (t, J=7.2 Hz, 2 H), 2.83 (t, J=7.3 Hz, 2 H), 2.56-2.48 (m, 2 H), 1.23 (s, 9 H); LRMS m/z (M+H) 235.4 found, 235.2 required.

3-(4-{[(1S,2S)-2-(5-methoxypyridin-2-yl)cyclopropyl]methoxy}-2-methylpyrimidin-5-yl)-5,6-dihydro-4H-pyrrolo[1,2-b]pyrazole (OO3)

A mixture of 5-bromo-4-{[(1S,2S)-2-(5-methoxypyridin-2-yl)cyclopropyl]-methoxy}-2-methylpyrimidine (2-3) (120 mg, 0.3 mmol), 3-(4,4,5,5-tetramethyl-1,3,2-dioxaborolan-2-yl)-5,6-dihydro-4H-pyrrolo[1,2-b]pyrazole (OO2) (104 mg, 0.4 mmol), tripotassium phosphate (145 mg, 0.7 mmol), S-Phos (14 mg, 0.03 mmol), and Pd(OAc)$_2$ (3.9 mg, 0.02 mmol) in THF (1.5 mL) and water (0.3 mL) was heated at 100° C. for 14 hours. The reaction mixture was allowed to cool to room temperature. The mixture was then diluted with EtOAc (10 mL), washed with sodium bicarbonate (2 mL) and brine (2 mL), dried over MgSO$_4$, filtered and concentrated. The crude residue was purified by reverse phase chromatography (Waters Sunfire Prep C18 OBD, 5-45% acetonitrile in water with 0.1% TFA modifier) to afford the title compound as a colorless gum. $^1$H NMR (500 MHz, DMSO): δ 8.51 (s, 1 H), 8.14 (d, J=2.9 Hz, 1 H), 7.84 (s, 1 H), 7.31-7.22 (m, 2 H), 4.53 (dd, J=11.3, 6.4 Hz, 1 H), 4.25 (dd, J=11.3, 8.2 Hz, 1 H), 4.04 (t, J=7.3 Hz, 2 H), 3.78 (s, 3 H), 2.97 (t, J=7.3 Hz, 2 H), 2.50 (s, 3 H), 2.39-2.32 (m, 2 H), 2.19 (dd, J=8.4, 4.7 Hz, 1 H), 1.79 (m, 1 H), 1.17 (dt, J=8.6, 4.5 Hz, 1 H), 1.06 (dd, J=8.6, 4.9 Hz, 1 H); HRMS m/z (M+H) 378.1921 found, 378.1925 required.

EXAMPLE 1-5

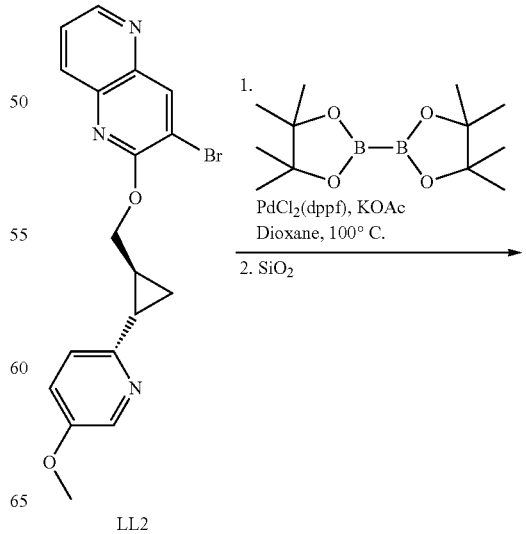

-continued

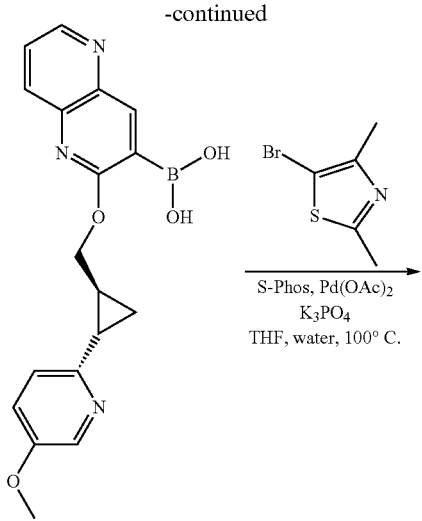

PP1

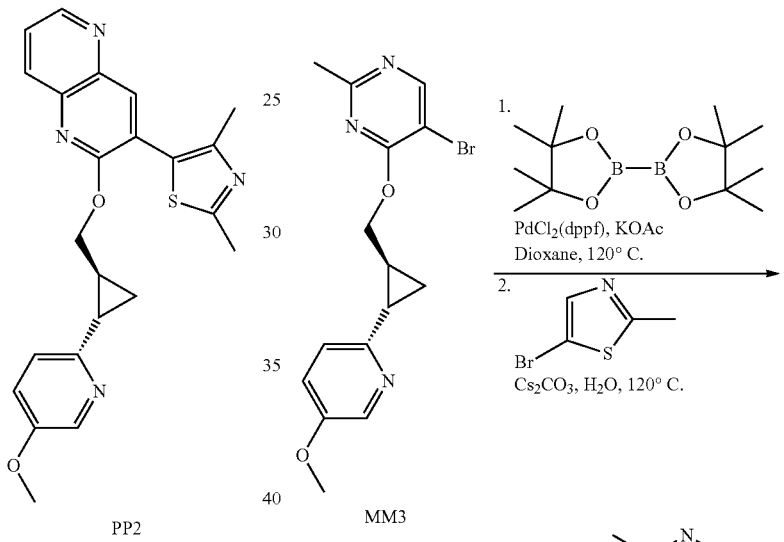

PP2

MM3

(2-{[(1S,2S)-2-(5-methoxypyridin-2-yl)cyclopropyl]methoxy}-1,5-naphthyridin-3-yl)boronic acid (PP1)

A mixture of 3-bromo-2-{[(1S,2S)-2-(5-methoxypyridin-2-yl)cyclopropyl]-methoxy}-1,5-naphthyridine (LL2) (800 mg, 2.1 mmol), bis(pinacolato)diboron (789 mg, 3.1 mmol), potassium acetate (813 mg, 8.3 mmol) and PdCl$_2$(dppf) (303 mg, 0.41 mmol) in dioxane (10.4 mL) under N$_2$ was heated at 100° C. for 14 hours. The reaction mixture was cooled to ambient temperature, partitioned between EtOAc (125 mL) and sat. sodium bicarbonate (25 mL), washed with water (25 mL), dried over MgSO$_4$, filtered and concentrated. The resulting residue was purified by flash chromatography (20% to 100% EtOAc in hexanes; hydrolysis on silica gel to boronic acid led to elution with 9:1 chloroform/methanol) to afford the title compound as a brown foam. LRMS m/z (M+H) 352.1 found, 352.1 required.

3-(2,4-dimethyl-1,3-thiazol-5-yl)-2-{[(1S,2S)-2-(5-methoxypyridin-2-yl)cyclopropyl]methoxy}-1,5-naphthyridine (PP2)

A mixture of (2-{[(1S,2S)-2-(5-methoxypyridin-2-yl)cyclopropyl]methoxy}-1,5-naphthyridin-3-yl)boronic acid (PP1) (25 mg, 0.050 mmol), 5-bromo-2,4-dimethyl-1,3-thiazole (9.6 mg, 0.050 mmol), K$_3$PO$_4$ (21.2 mg, 0.10 mmol), S-Phos (2.0 mg, 0.005 mmol), and Pd(OAc)$_2$ (0.6 mg, 0.002 mmol) in THF (0.3 mL) and water (0.05 mL) was heated at 100° C. for 14 hours. The reaction mixture was allowed to cool to room temperature. The mixture was then diluted with EtOAc (5 mL), washed with sodium bicarbonate (1 mL) and brine (1 mL), dried over MgSO$_4$, filtered and concentrated. The resulting residue was purified by reverse phase chromatography (Waters Sunfire Prep C18 OBD, 5-45% acetonitrile in water with 0.1% TFA modifier) to afford the title compound. $^1$H NMR (500 MHz, DMSO): δ 8.83 (dd, J=4.2, 1.6 Hz, 1 H), 8.29 (s, 1 H), 8.20 (d, J=8.5 Hz, 1 H), 8.12 (d, J=2.9 Hz, 1 H), 7.71 (dd, J=8.4, 4.2 Hz, 1 H), 7.30-7.23 (m, 2 H), 4.61 (dd, J=11.3, 6.7 Hz, 1 H), 4.39 (dd, J=11.3, 7.8 Hz, 1 H), 3.78 (s, 3 H), 2.61 (s, 3 H), 2.36 (s, 3 H), 2.20 (dt, J=8.5, 4.6 Hz, 1 H), 1.79 (s, 1 H), 1.24 (s, 1 H), 1.09-1.04 (m, 1 H); HRMS m/z (M+H) 418.1534 found, 418.1536 required.

EXAMPLE 1-6

QQ1

4-{[(1S,2S)-2-(5-methoxypyridin-2-yl)cyclopropyl]methoxy}-2-methyl-5-(2-methyl-1,3-thiazol-5-yl)pyrimidine (QQ1)

A mixture of 5-bromo-4-{[(1S,2S)-2-(5-methoxypyridin-2-yl)cyclopropyl]-methoxy}-2-methylpyrimidine (MM3)

(35 mg, 0.10 mmol), bis(pinacolato)diboron (27.9 mg, 0.11 mmol), potassium acetate (39 mg, 0.40 mmol) and PdCl$_2$ (dppf) (14.6 mg, 0.020 mmol) in dioxane (0.6 mL) under N$_2$ was heated at 120° C. for 2 hours. A solution of 5-bromo-2-methyl-1,3-thiazole (26.7 mg, 0.15 mmol) in dioxane (0.2 mL) was added followed by aqueous cesium carbonate (2 M, 0.15 mL, 0.30 mmol). The resulting mixture was heated at 120° C. for 14 hours. The mixture was cooled to ambient temperature, diluted with EtOAc (5 mL), washed with sodium bicarbonate (1 mL) and brine (1 mL), dried over MgSO$_4$, filtered and concentrated. The resulting residue was purified by reverse phase chromatography (Waters Sunfire Prep C18 OBD, 5-45% acetonitrile in water with 0.1% TFA modifier) to afford the title compound as a white, gummy solid. $^1$H NMR (500 MHz, DMSO): δ 8.83 (s, 1 H), 8.20 (s, 1 H), 8.14 (d, J=2.9 Hz, 1 H), 7.31-7.25 (m, 2 H), 4.56 (dd, J=11.2, 6.9 Hz, 1 H), 4.37 (dd, J=11.2, 7.6 Hz, 1 H), 3.78 (s, 3 H), 2.62 (s, 3 H), 2.54 (s, 3 H), 2.22 (dt, J=8.6, 4.6 Hz, 1 H), 1.78 (s, 1 H), 1.24-1.18 (m, 1 H), 1.11-1.05 (m, 1 H); HRMS m/z (M+H) 369.1386 found, 369.1380 required.

EXAMPLE 1-7

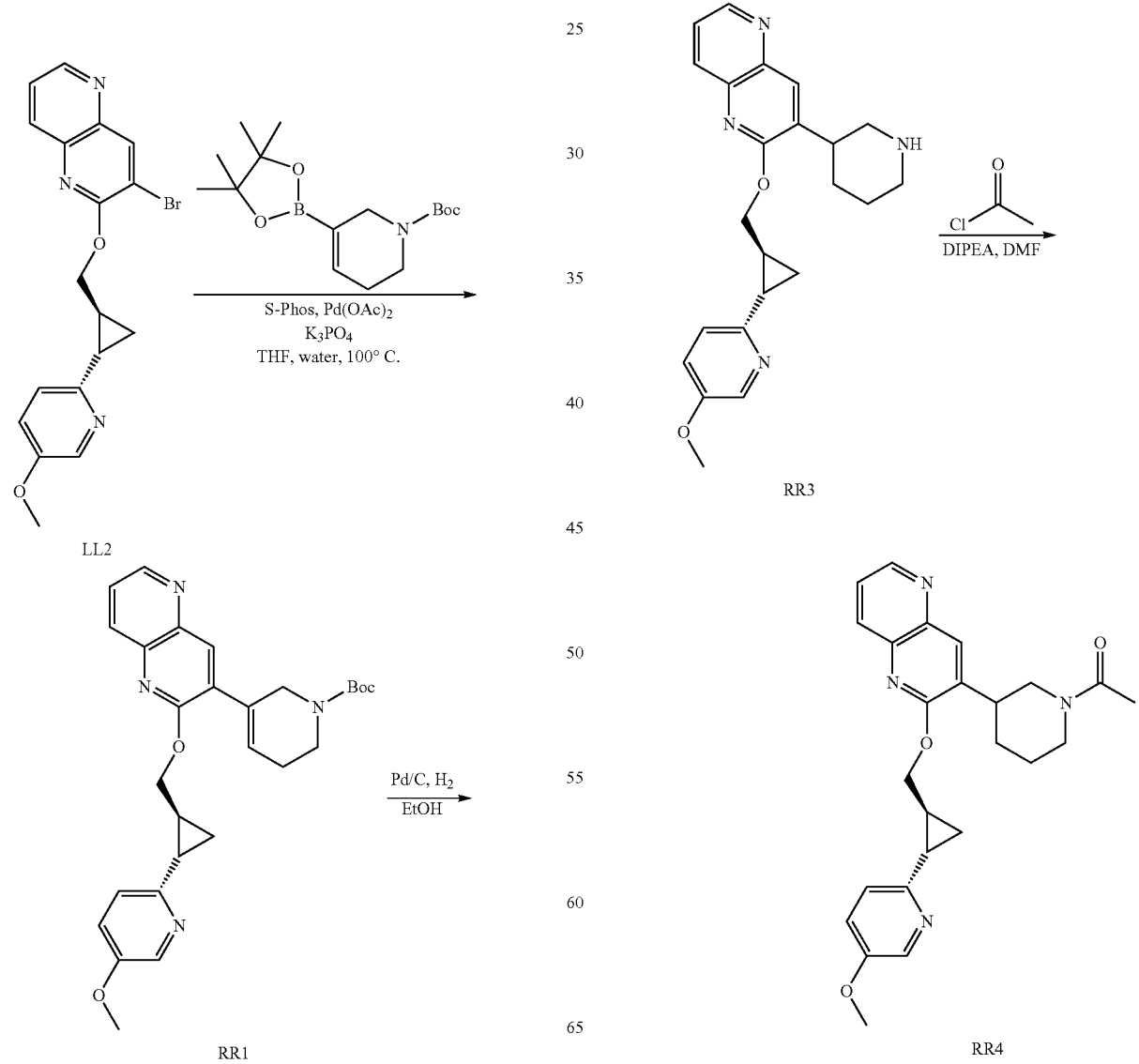

Tert-butyl 5-(2-{[(1S,2S)-2-(5-methoxypyridin-2-yl)cyclopropyl]methoxy}-1,5-naphthyridin-3-yl)-3,6-dihydropyridine-1 (2H)-carboxylate (RR1)

A mixture of 3-bromo-2-{[(1S,2S)-2-(5-methoxypyridin-2-yl)cyclopropyl]-methoxy}-1,5-naphthyridine (LL2) (50 mg, 0.13 mmol), tert-butyl 5-(4,4,5,5-tetramethyl-1,3,2-dioxaborolan-2-yl)-3,6-dihydropyridine-1(2H)-carboxylate (52 mg, 0.17 mmol), tripotassium phosphate (55 mg, 0.26 mmol), S-Phos (5.3 mg, 0.01 mmol), and Pd(OAc)$_2$ (1.5 mg, 0.006 mmol) in THF (0.6 mL) and water (0.1 mL) was heated at 100° C. for 14 hours. The reaction mixture was allowed to cool to room temperature. The mixture was then diluted with EtOAc (5 mL), washed with sodium bicarbonate (1 mL) and brine (1 mL), dried over MgSO$_4$, filtered and concentrated. The resulting residue was purified by reverse phase chromatography (Waters Sunfire Prep C18 OBD, 5-60% acetonitrile in water with 0.1% TFA modifier) to afford the title compound. $^1$H NMR (500 MHz, DMSO): δ 8.79 (dd, J=4.3, 1.6 Hz, 1 H), 8.18-8.06 (m, 3 H), 7.66 (dd, J=8.4, 4.2 Hz, 1 H), 7.24 (s, 2 H), 6.26 (s, 1 H), 4.54 (m, 1 H), 4.44 (m, 1 H), 4.26 (brs, 2 H), 3.77 (s, 3 H), 3.49-3.40 (m, 2 H), 2.27 (s, 2 H), 2.24-2.19 (m, 1 H), 1.80 (s, 1 H), 1.41 (s, 9 H), 1.23-1.15 (m, 2 H), 1.08 (dt, J=8.7, 4.6 Hz, 1 H); HRMS m/z (M+H) 489.2486 found, 489.2496 required.

Tert-butyl 3-(2-{[(1S,2S)-2-(5-methoxypyridin-2-yl)cyclopropyl]methoxy}-1,5-naphthyridin-3-yl)piperidine-1-carboxylate (RR2)

To tert-butyl 5-(2-{[(1S,2S)-2-(5-methoxypyridin-2-yl)cyclopropyl]methoxy}-1,5-naphthyridin-3-yl)-3,6-dihydropyridine-1(2H)-carboxylate (RR1) (50 mg, 0.10 mmol) in ethanol (2 mL) was carefully added 10% palladium on carbon (10.6 mg, 0.01 mmol) under N$_2$. The reaction mixture was evacuated and backfilled three times with hydrogen via balloon and then stirred overnight at room temperature. Upon completion, the mixture was filtered through celite washing with methanol and concentrated in vacuo to afford the title compound. $^1$H NMR (500 MHz, DMSO): δ 8.77 (1 H, d, J=4.5 Hz), 8.12 (3 H, d, J=9.4 Hz), 7.64 (1 H, m), 7.24 (2 H, s), 4.53 (m, 2 H), 4.26 (m, 2 H), 3.77 (s, 3 H), 3.49-3.40 (m, 3 H), 2.27 (s, 2 H), 2.24-2.19 (m, 1 H), 1.99 (m, 1 H), 1.80 (s, 1 H), 1.41 (s, 9 H), 1.23-1.15 (m, 2 H), 1.08 (dt, J=8.7, 4.6 Hz, 1 H); HRMS m/z (M+H) 491.2654 found, 491.2653 required.

2-{[(1S,2S)-2-(5-methoxypyridin-2-yl)cyclopropyl]methoxy}-3-(piperidin-3-yl)-1,5-naphthyridine (RR3)

To a solution of tert-butyl 3-(2-{[(1S,2S)-2-(5-methoxypyridin-2-yl)cyclopropyl]methoxy}-1,5-naphthyridin-3-yl)piperidine-1-carboxylate (RR2) (38 mg, 0.08 mmol) in DCM (3 mL) was added concentrated TFA (0.5 mL, 6.5 mmol). After five minutes, saturated sodium bicarbonate (3 mL) was added and the mixture was extracted with EtOAc (3×15 mL). The combined organics were dried over MgSO$_4$, filtered and concentrated in vacuo to afford the title compound, which was sufficiently pure to use in the subsequent step without further purification. HRMS m/z (M+H) 391.2133 found, 391.2129 required.

1-[3-(2-{[(1S,2S)-2-(5-methoxypyridin-2-yl)cyclopropyl]methoxy}-1,5-naphthyridin-3-yl)piperidin-1-yl]ethanone (RR4)

To a solution of 2-{[(1S,2S)-2-(5-methoxypyridin-2-yl)cyclopropyl]methoxy}-3-(piperidin-3-yl)-1,5-naphthyridine (RR3) (12 mg, 0.03 mmol) in DMF (0.3 mL) was added acetyl chloride (0.006 mL, 0.09 mmol) and Hunig's Base (0.015 mL, 0.09 mmol). After five minutes, the mixture was purified directly by reverse phase chromatography (Waters Sunfire Prep C18 OBD, 5-60% acetonitrile in water with 0.1% TFA modifier) to afford the title compound. $^1$H NMR (500 MHz, DMSO): δ 8.78 (s, 1 H), 8.13 (s, 3 H), 7.64 (s, 1 H), 7.26 (m, 2 H), 4.50 (m, 2 H), 4.26 (brs, 2 H), 3.77 (s, 3 H), 3.49-3.40 (m, 2 H), 3.08 (m, 2 H), 2.27 (m, 2 H), 2.24-2.19 (m, 1 H), 2.05 (s, 3 H), 1.80 (s, 1 H), 1.23-1.15 (m, 2 H), 1.08 (dt, J=8.7, 4.6 Hz, 1 H); HRMS m/z (M+H) 433.2228 found, 433.2234 required.

EXAMPLE 1-8

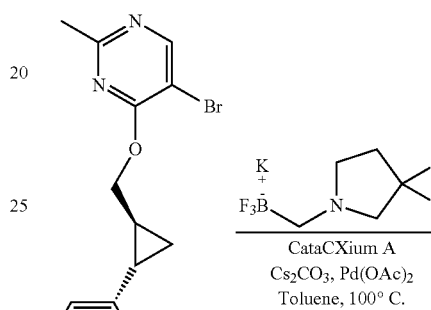

MM3

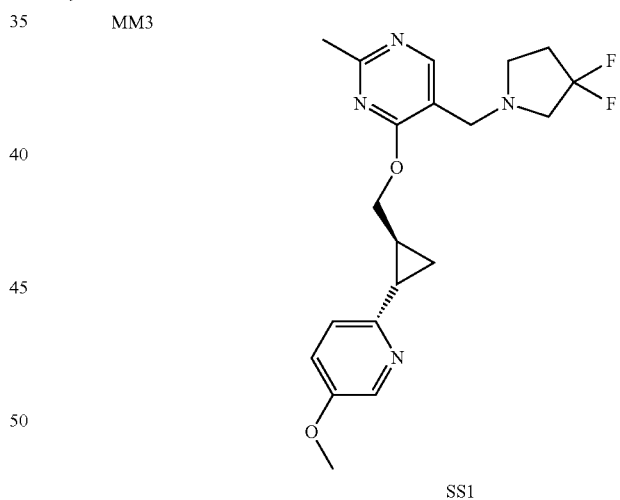

SS1

5-[(3,3-difluoropyrrolidin-1-yl)methyl]-4-{[(1S,2S)-2-(5-methoxypyridin-2-yl)cyclopropyl]methoxy}-2-methylpyrimidine (SS1)

A mixture of 5-bromo-4-{[(1S,2S)-2-(5-methoxypyridin-2-yl)cyclopropyl]-methoxy}-2-methylpyrimidine (MM3) (20 mg, 0.05 mmol, 1.0 eq), potassium [(3,3-difluoropyrrolidin-1-yl)methyl](trifluoro)borate (23.3 mg, 0.1 mmol, 2.0 eq), CataCXiumA (1.8 mg, 0.005 mmol, 0.10 eq), cesium carbonate (50.2 mg, 0.15 mmol, 3.0 eq) and Pd(OAc)$_2$ (0.6 mg, 0.003 mmol, 0.05 eq) in toluene (0.2 mL) and water (0.06 mL) was heated at 100° C. for 14 hours. The reaction mixture was allowed to cool to room temperature. The mixture was then diluted with EtOAc (5 mL), washed with sodium bicarbonate (1 mL) and brine (1 mL), dried over MgSO$_4$, filtered and concentrated. The resulting residue was purified by reverse phase chromatography (Waters Sunfire Prep C18 OBD, 5-60% acetonitrile in water with 0.1% TFA modifier) to afford the title compound. $^1$H NMR (500 MHz, DMSO): δ 8.30 (s, 1 H), 8.11 (d, J=3.1 Hz, 1 H), 7.29-7.19 (m, 2 H), 4.42 (dd, J=11.4, 6.6 Hz, 1 H), 4.33 (dd, J=11.4, 7.3 Hz, 1 H), 3.77 (s, 3 H), 3.56 (s, 2 H), 2.85 (t, J=13.2 Hz, 2 H), 2.67 (t, J=7.2 Hz, 2 H), 2.49 (s, 3H), 2.21-2.12 (m, 3 H), 1.72 (s, 1 H), 1.12 (dt, J=8.7, 4.5 Hz, 1 H), 1.02 (dt, J=8.8, 4.6 Hz, 1 H); HRMS m/z (M+H) 391.1929 found, 391.1940 required.

EXAMPLE 1-9

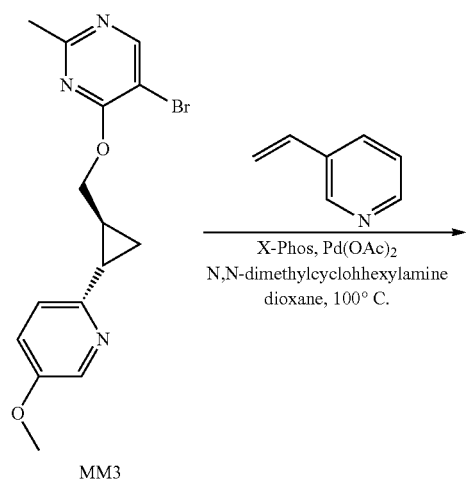

MM3

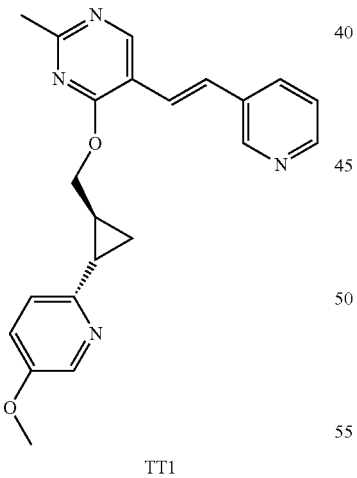

TT1

4-{[(1S,2S)-2-(5-methoxypyridin-2-yl)cyclopropyl]methoxy}-2-methyl-5-[(E)-2-(pyridin-3-yl)ethenyl]pyrimidine (TT1)

A solution of MM3 (200 mg, 0.57 mmol), 3-vinylpyridine (90 mg, 0.86 mmol), X-Phos (27.2 mg, 0.057 mmol), and Pd(OAc)$_2$ (6.41 mg, 0.028 mmol) in 1,4-dioxane (2.8 mL) was treated with N,N-dicyclohexylmethyl amine (223 mg, 1.14 mmol). The reaction vessel was sealed and heated to 100° C. overnight. The reaction mixture was cooled to room temperature, diluted with EtOAc (30 mL), and washed with saturated aqueous NaHCO$_3$ (35 mL) and brine (35 mL). The organic layer was dried over Na$_2$SO$_4$, filtered, and concentrated in vacuo. The resulting residue was purified by gradient elution on silica gel (0% to 100% EtOAc in Hexanes over 15 minutes). The solvent gradient was then ramped to 100% (25% MeOH in EtOAc for 5 minutes). This yielded the title compound as a white solid. $^1$H NMR (500 MHz, CDCl$_3$): δ 8.64 (s, 1 H); 8.52-8.48 (m, 2 H); 8.19 (s, 1 H); 7.75 (d, J=8.0 Hz, 1 H); 7.33 (d, J=16.6 Hz, 1 H); 7.27 (t, J=6.7 Hz, 1 H); 7.12-7.08 (m, 2 H); 7.10 (d, J=15.5 Hz, 1 H); 4.56 (dd, J=11.3, 6.9 Hz, 1 H); 4.46 (dd, J=11.3, 7.4 Hz, 1 H); 3.85 (s, 3 H); 2.63 (s, 3 H); 2.14 (dt, J=8.6, 4.6 Hz, 1 H); 1.98-1.92 (m, 1 H); 1.36 (dt, J=8.6, 4.9 Hz, 1 H); 1.11 (dt, J=8.6, 5.1 Hz, 1 H); HRMS m/z (M+H) 375.1815 found, 375.1816 required

EXAMPLE 1-10

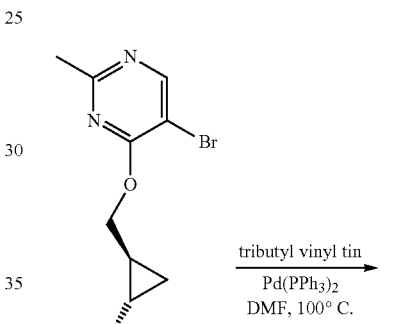

MM3

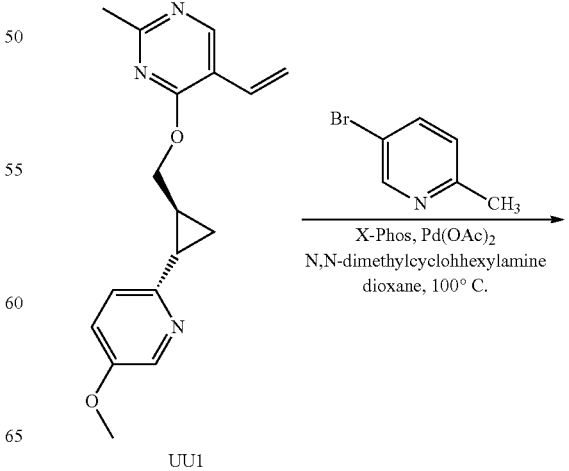

UU1

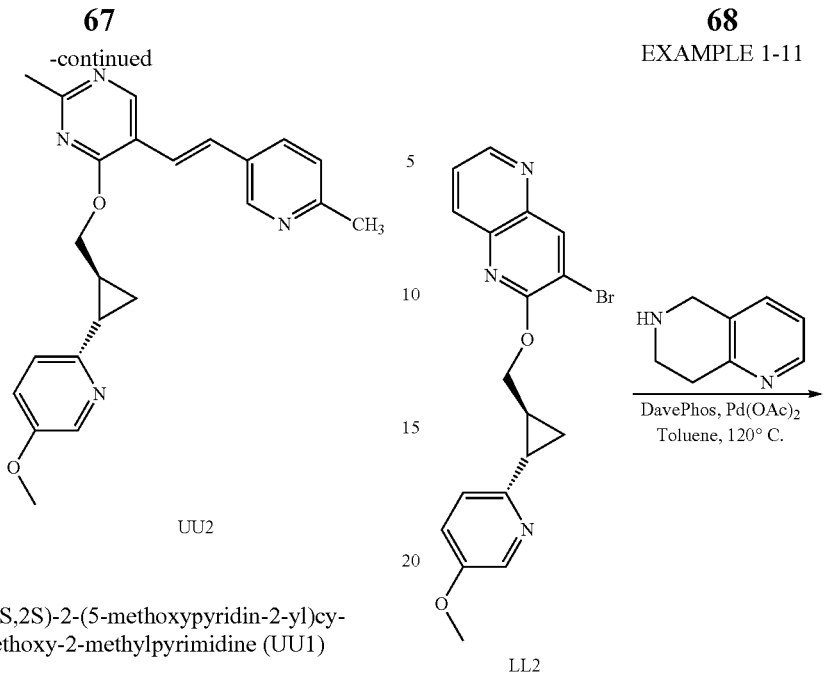

UU2

5-ethenyl-4-[(1S,2S)-2-(5-methoxypyridin-2-yl)cyclopropyl]methoxy-2-methylpyrimidine (UU1)

A solution of vinyl tributyl tin (294 mg; 0.93 mmol), MM3 (250 mg, 0.71 mmol), and Pd(PPh$_3$)$_4$ (41.2 mg, 0.036 mmol) in DMF (2.4 mL) was heated at 100° C. for one hour. The reaction mixture was cooled, diluted with EtOAc (25 mL) and washed with saturated aqueous NaHCO$_3$ (30 mL) and brine (30 mL). The organic layer was dried over Na$_2$SO$_4$, filtered, and concentrated in vacuo. The resulting residue was purified by gradient elution on silica gel (0% to 100% EtOAc in Hexanes over 15 minutes) to afford the title compound as a brown oil. $^1$H NMR (500 MHz, CDCl$_3$): δ 8.37 (s, 1 H); 8.16 (d, J=2.7 Hz, 1 H); 7.10-7.05 (m, 2 H); 6.67 (dd, J=17.8, 11.4 Hz, 1 H); 5.91 (dd, J=17.8, 1.3 Hz, 1 H); 5.35 (dd, J=11.4, 1.3 Hz, 1 H); 4.44 (d, J=7.0 Hz, 2 H); 3.83 (s, 3 H); 2.58 (s, 3 H); 2.08 (dt, J=8.7, 4.6 Hz, 1 H); 1.90-1.84 (m, 1 H); 1.30 (dt, J=8.6, 4.8 Hz, 1 H); 1.05 (dt, J=8.7, 5.1 Hz, 1 H); HRMS m/z (M+H) 298.1547 found, 298.1550 required

4-{[(1S,2S)-2-(5-methoxypyridin-2-yl)cyclopropyl]methoxy}-2-methyl-5-[(E)-2-(6-methylpyridin-3-yl)ethenyl]pyrimidine (UU2)

A solution of (UU1) (50 mg; 0.17 mmol), 5-bromo-2-methyl-pyridine (43.4 mg, 0.25 mmol), X-Phos (8.02 mg, 0.017 mmol), Pd(OAc)$_2$ (1.89 mg, 8.41 µmol) in 1,4-dioxane (840 µL) was treated with N,N-dicyclohexylmethyl amine (65.7 mg, 0.34 mmol). The reaction vessel was sealed and heated to 100° C. overnight. The reaction mixture was cooled, diluted with EtOAc (10 mL) and washed with saturated aqueous NaHCO$_3$ (15 mL) and brine (15 mL). The organic layer was dried over Na$_2$SO$_4$, filtered, and concentrated in vacuo. The resulting residue was purified by gradient elution on silica gel (0% to 100% EtOAc in hexanes); the solvent gradient was then ramped to 100% (25% MeOH in EtOAc). This yielded the title compound as a white solid. $^1$H NMR (500 MHz, CDCl$_3$): δ 8.51 (d, J=2.3 Hz, 1 H); 8.47 (s, 1 H); 8.18 (d, J=2.3 Hz, 1 H); 7.65 (dd, J=8.1, 2.4 Hz, 1 H); 7.28 (d, J=17.1 Hz, 1 H); 7.13 (d, J=8.2 Hz, 1 H); 7.09 (m, Hz, 2 H); 7.04 (d, J=16.5 Hz, 1H); 4.53 (dd, J=11.3, 6.8 Hz, 1 H); 4.48-4.42 (m, 1 H); 3.84 (s, 3 H); 2.61 (s, 3 H); 2.56 (s, 3H); 2.12 (dt, J=8.6, 4.6 Hz, 1 H); 1.96-1.89 (m, 1 H); 1.34 (dt, J=8.6, 4.9 Hz, 1 H); 1.09 (dt, J=8.7, 5.1 Hz, 1 H); HRMS m/z (M+H) 389.1962 found, 389.1972 required.

EXAMPLE 1-11

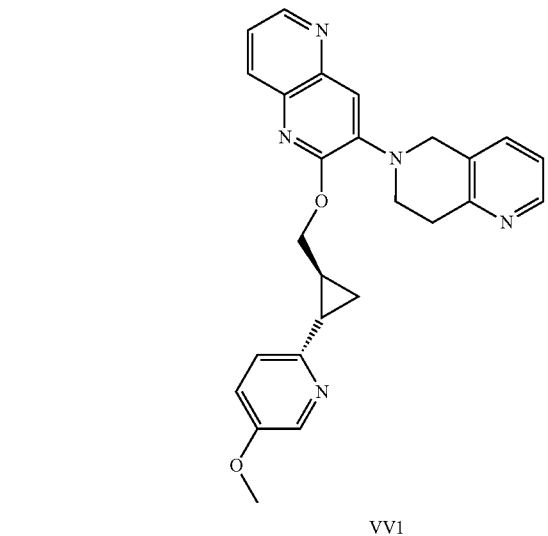

3-(7,8-dihydro-1,6-naphthyridin-6(5H)-yl)-2-{[(1S,2S)-2-(5-methoxypyridin-2-yl)cyclopropyl]methoxy}-1,5-naphthyridine (VV1)

A mixture of 3-bromo-2-{[(1S,2S)-2-(5-methoxypyridin-2-yl)cyclopropyl]methoxy}-1,5-naphthyridine (LL1) (25 mg, 0.07 mmol), 5,6,7,8-tetrahydro-1,6-naphthyridine (16.1 mg, 0.08 mmol), sodium t-butoxide (21.8 mg, 0.23 mmol), DavePhos (3.8 mg, 0.009 mmol) and tris(dibenzylideneacetone)dipalladium(0) (4.5 mg, 0.005 mol) in toluene (0.3 mL) was heated at 100° C. for 14 hours. The reaction mixture was allowed to cool to room temperature. The mixture was then diluted with EtOAc (5 mL), washed with sodium bicarbonate (1 mL) and brine (1 mL), dried over MgSO$_4$, filtered and concentrated. The crude residue was purified by reverse phase chromatography (Waters Sunfire Prep C18 OBD, 5-60% acetonitrile in water with 0.1% TFA modifier) to afford the title compound. ¹H NMR (500 MHz, DMSO): δ 8.69 (d, J=4.3 Hz, 1 H), 8.38 (d, J=4.8 Hz, 1 H), 8.14 (s, 1 H), 8.06 (d, J=8.3 Hz, 1 H), 7.61-7.53 (m, 2 H), 7.49 (dd, J=8.4, 4.4 Hz, 1 H), 7.27 (s, 2 H), 7.20 (dd, J=7.9, 4.9 Hz, 1 H), 4.63 (dd, J=11.2, 6.4 Hz, 1 H), 4.47-4.36 (m, 3 H), 3.79 (s, 3 H), 3.70-3.59 (m, 2 H), 2.93 (s, 2 H), 2.27-2.23 (m, 1 H), 1.85 (s, 1 H), 1.24 (m, 1 H), 1.12 (dd, J=8.7, 5.4 Hz, 1 H); LRMS m/z (M+H) 440.3 found, 440.2 required.

EXAMPLE 1-12

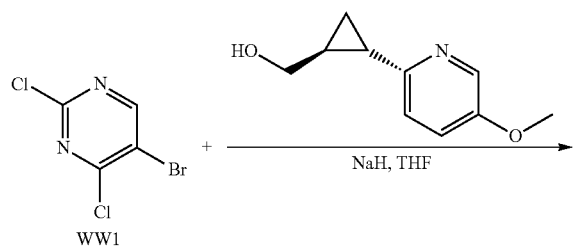

WW1

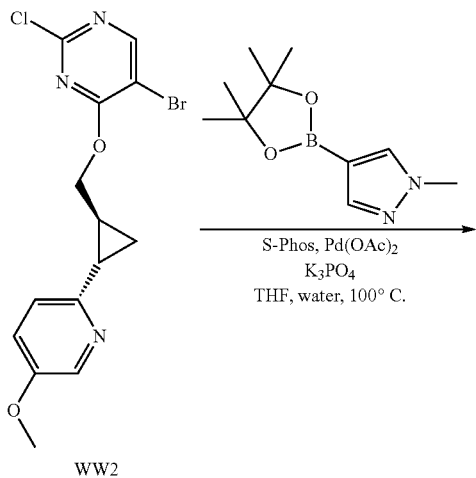

WW2

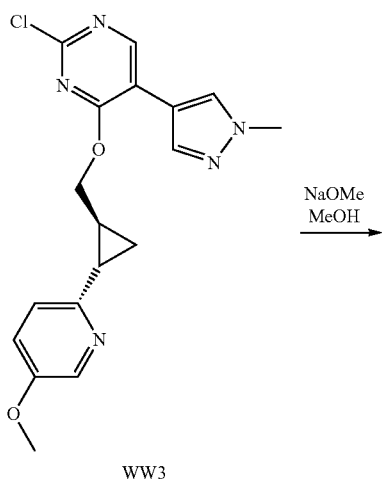

WW3

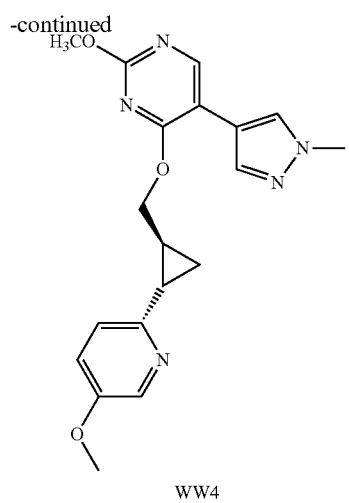

WW4

5-bromo-4-{[(1S,2S)-2-(5-methoxypyridin-2-yl) cyclopropyl]methoxy}-2-methylpyrimidine (WW2)

NaH (78 mg, 1.95 mmol, 60% disp.) was added to a stirring solution of [(1S,2S)-2-(5-methoxypyridin-2-yl)cyclopropyl]methanol (S,S-DD3, ent₂) (350 mg, 1.953 mmol) and 5-bromo-2,4-dichloropyrimidine (445 mg, 1.953 mmol) in THF (9.77 mL). The reaction mixture was stirred at room temperature for 1 hour, and then quenched by dropwise addition of saturated aqueous NaHCO₃. The reaction mixture was diluted with EtOAc (50 mL), and washed with saturated aqueous NaHCO₃ (50 mL) and brine (50 mL). The organics were dried over MgSO₄, filtered, and concentrated in vacuo to afford the title compound as an orange gum. The unpurified product was sufficiently pure to use in the subsequent step without further purification. LRMS m/z (M+H) 372.2 found, 372.0 required.

4-{[(1S,2S)-2-(5-methoxypyridin-2-yl)cyclopropyl] methoxy}-2-methyl-5-(1-methyl-1H-pyrazol-4-yl) pyrimidine (WW3)

The title compound was prepared according to the protocol outlined in Example 13 for the synthesis of MM4. WW3 was isolated as a white solid. ¹H NMR (500 MHz, DMSO): δ 8.520 (s, 1 H), 8.14 (t, J=1.8 Hz, 1 H), 7.88 (s, 1 H), 7.86 (s, 1 H), 7.10-7.17 (m, 2H), 4.55 (dd, J=11.2, 7.3 Hz, 1 H), 4.45 (dd, J=11.2, 7.6 Hz, 1 H), 3.89 (s, 3 H), 3.83 (s, 3 H), 2.12 (dt, J=8.1, 5.1 Hz, 1 H), 1.90-2.01 (m, 1 H), 1.38 (dt, J=8.5, 4.9 Hz, 1 H), 1.09 (dt, J=8.5, 5.4, 1 H); HRMS m/z (M+H) 372.1230 found, 372.1222 required.

2-methoxy-4-{[(1,2S)-2-(5-methoxypyridin-2-yl) cyclopropyl]methoxy}-5-(1-methyl-1H-pyrazol-4-yl) pyrimidine (WW4)

Sodium methoxide (13 mg, 0.242 mmol, 30% solution in MeOH) was added to a stirring solution of 4-{[(1S,2S)-2-(5-methoxypyridin-2-yl)cyclopropyl]methoxy}-2-methyl-5-(1-methyl-1H-pyrazol-4-yl)pyrimidine in MeOH (0.1 mL). The reaction mixture was stirred at room temperature for 8 hours, and then purified directly by reverse phase chromatography (Waters Sunfire Prep C18 OBD, 5-95% acetonitrile in water with 0.1% TFA modifier) to afford the title compound. ¹H NMR (500 MHz, CDCl₃): δ 8.44 (s, 1 H), 8.19 (d, J=2.0 Hz, 1 H), 7.82 (s, 1 H), 7.77 (s, 1 H), 7.09-7.15 (m, 2 H), 4.52 (dd, J=11.2, 7.1 Hz, 1 H), 4.25 (dd, J=11.2, 7.3 Hz, 1 H), 4.00 (s, 3 H), 3.88 (s, 3 H), 3.84 (s, 3 H), 2.10 (dt, J=8.1, 5.1 Hz, 1 H), 1.94 (m, 1 H), 1.37 (dt, J=8.3, 4.8 Hz, 1 H), 1.05-1.10 (m, 1 H); LRMS m/z (M+H) 368.4 found, 368.2 required.

EXAMPLE 1-13

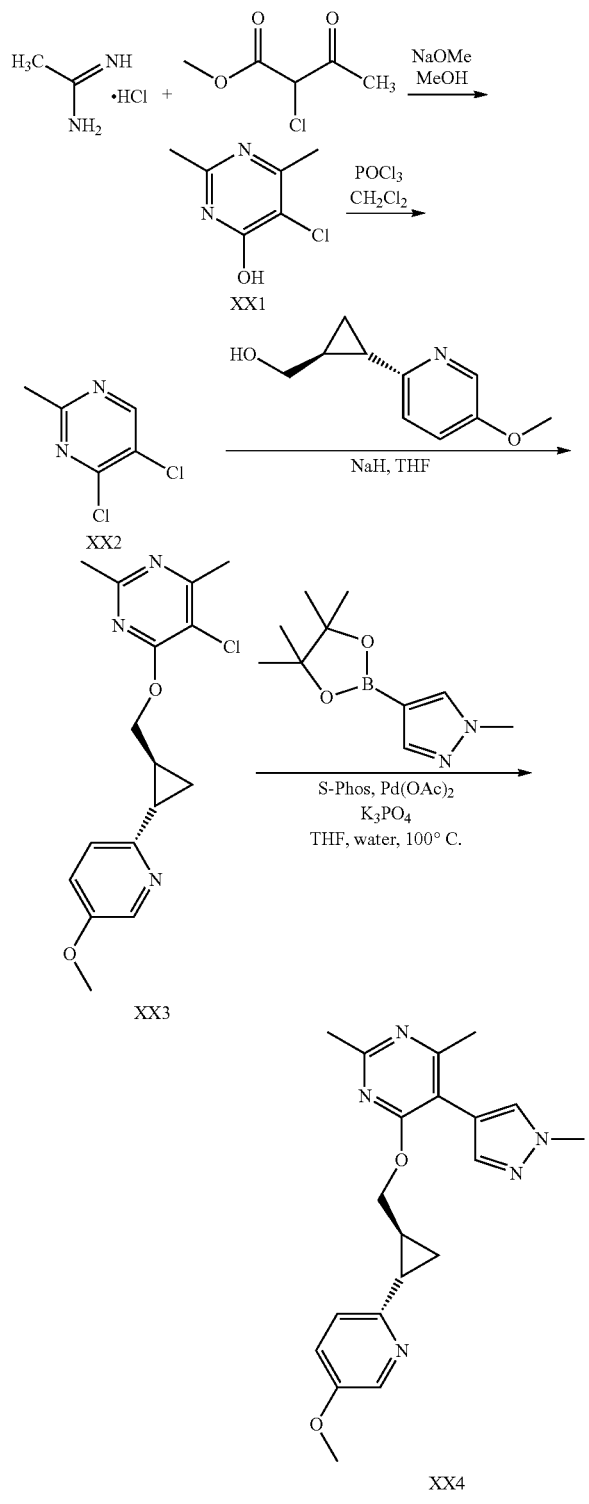

5-chloro-2,6-dimethylpyrimidin-4-ol (XX1)

Sodium methoxide (328 mg, 6.08 mmol, 30% solution in MeOH) was added to a stirring suspension of acetamidine hydrochloride (191 mg, 2.03 mmol) and methyl 2-chloro-3-oxobutanoate (500 mg, 3.04 mmol) in MeOH (10.1 mL). The reaction mixture was heated to 80° C. for 3 hours and then cooled to room temperature. With stirring, the reaction was treated with 2N HCl in Et₂O (50 mL), and then concentrated in vacuo. The resulting solid was suspended in 1:1 acetone/CH₂Cl₂, stirred vigorously for 10 mins, and the solids collected by filtration to afford the title compound as a light yellow solid. The isolated product was sufficiently pure to use in the subsequent step without further purification. LRMS m/z (M+H) 159.2 found, 159.0 required.

4,5-dichloro-2,6-dimethylpyrimidine (XX2)

The title compound was prepared according to the protocol outlined in Example 13 for the synthesis of MM2. XX2 was isolated as a yellow gum, and was sufficiently pure to use in the subsequent step without further purification. LRMS m/z (M+H) 177.1 found, 177.0 required.

5-chloro-4-{[(1S,2S)-2-(5-methoxypyridin-2-yl)cyclopropyl]methoxy}-2,6-dimethylpyrimidine (XX3)

The title compound was prepared according to the protocol outlined in Example 13 for the synthesis of MM3. XX3 was purified by reverse phase chromatography (Waters Sunfire Prep C18 OBD, 5-95% acetonitrile in water with 0.1% TFA modifier) to afford the title compound as a colorless gum. HRMS m/z (M+H) 320.1165 found, 320.1160 required.

4-{[(1S,2S)-2-(5-methoxypyridin-2-yl)cyclopropyl]methoxy}-2,6-dimethyl-5-(1-methyl-1H-pyrazol-4-yl)pyrimidine (XX4)

The title compound was prepared according to the protocol outlined in Example 13 for the synthesis of MM4. XX4 was purified by reverse phase chromatography (Waters Sunfire Prep C18 OBD, 5-95% acetonitrile in water with 0.1% TFA modifier) to afford the title compound as a white solid. ¹H NMR (500 MHz, DMSO): δ 8.16 (d, J=2.9 Hz, 1 H), 7.63 (s, 1 H), 7.56 (s, 1 H), 7.10 (dd, J=8.5, 2.9 Hz, 1 H), 7.05 (d J=8.5 Hz, 1 H), 4.44 (dd, J=11.5, 7.1 Hz, 1 H), 4.34 (dd, J=11.5, 7.3 Hz, 1 H), 3.89 (s, 3 H), 3.82 (s, 3 H), 2.57 (s, 3 H), 2.49 (s, 3 H), 2.04 (dt, J=8.3, 4.9 Hz, 1 H), 1.83 (m, 1 H), 1.28 (dt, J=8.6, 4.9 Hz, 1 H), 1.02 (dt, J=8.7, 5.0 Hz, 1 H); HRMS m/z (M+H) 366.1940 found, 366.1925 required.

EXAMPLE 1-14

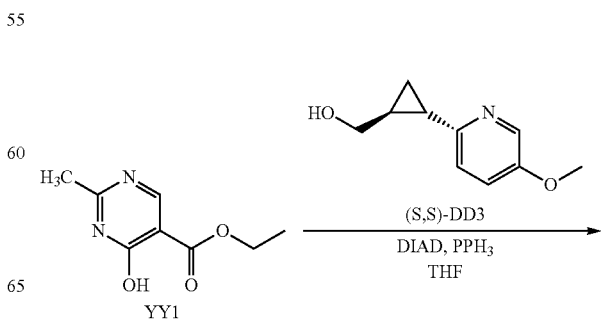

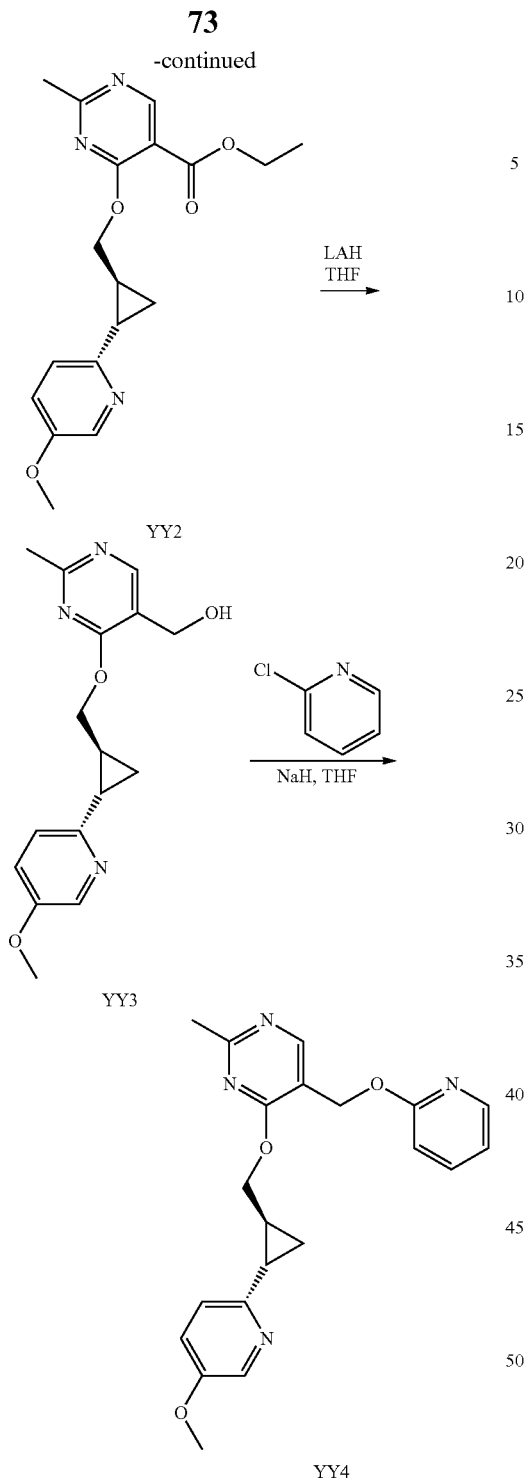

ethyl-4-{[(1S,2S)-2-(5-methoxypyridin-2-yl)cyclopropyl]methoxy}-2-methylpyrimidine-5-carboxylate (YY2)

The title compound was prepared according to the protocol outlined in Example 12 for the synthesis of LL2. YY2 was purified by reverse phase chromatography (Waters Sunfire Prep C18 OBD, 5-95% acetonitrile in water with 0.1% TFA modifier) to afford the title compound as a white solid. $^1$H NMR (500 MHz, DMSO): δ 8.51 (s, 1 H), 8.10 (d, J=2.4 Hz, 1H), 7.05-7.15 (m, 2 H), 4.37 (q, J=7.1 Hz, 2 H), 4.33 (d, J=7.1 Hz, 2 H), 3.81 (s, 3 H), 2.70 (s, 3 H), 2.25 (dt, J=8.6, 5.1 Hz, 1 H), 1.65-1.73 (m, 1 H), 1.37 (t, J=7.1 Hz, 3 H), 1.20-1.25 (m, 1 H), 1.13-1.17 (m, 1 H); LRMS m/z (M+H) 344.4 found, 344.2 required.

(4-{[(1S,2S)-2-(5-methoxypyridin-2-yl)cyclopropyl]methoxy}-2-methylpyrimidin-5-yl)methanol (YY3)

A 1N THF solution of LAH (0.175 mL, 0.175 mmol) was added dropwise to a 0° C. solution of ethyl-4-{[(1S,2S)-2-(5-methoxypyridin-2-yl)cyclopropyl]methoxy}-2-methylpyrimidine-5-carboxylate (30 mg, 0.087 mmol) in THF (0.58 mL). The reaction mixture was slowly warmed to room temperature, and then stirred for 30 mins. The reaction mixture was re-cooled to 0° C. and the carefully quenched by dropwise addition of water (10 μL), 15% NaOH in water (20 μL), and then water (20 μL). The slurry was treated with excess Na$_2$SO$_4$, stirred vigorously at room temperature for 10 mins, and then filtered through a pad of Celite eluting exhaustively with 1:1 CH$_2$Cl$_2$/MeOH. The filtrated was concentrated in vacuo. The resulting product was sufficiently pure to use in the subsequent step without further purification. LRMS m/z (M+H) 302.4 found, 302.1 required.

4-{[(1S,2S)-2-(5-methoxypyridin-2-yl)cyclopropyl]methoxy}-2-methyl-5-[(pyridin-2-yloxy)methyl]pyrimidine (YY4)

NaH (4 mg, 0.10 mmol, 60% disp.) was added in one portion to a stirring solution of (4-{[(1S,2S)-2-(5-methoxypyridin-2-yl)cyclopropyl]methoxy}-2-methylpyrimidin-5-yl)methanol (15 mg, 0.05 mmol) and 2-chloropyridine (11.3 mg, 0.1 mmol) in THF (0.33 mL) in a small pressure vessel. The vessel was sealed and then heated to 100° C. for 2 h. The reaction mixture was cooled to room temperature and then quenched by addition of 2 drops of saturated aqueous NaHCO$_3$. The reaction mixture was diluted with EtOAc (5 mL) and washed sequentially with saturated aqueous NaHCO$_3$ (5 mL) and brine (5 mL). The organics were dried over MgSO$_4$, filtered, and concentrated in vacuo. The resulting residue was purified by reverse phase chromatography (Waters Sunfire Prep C18 OBD, 5-95% acetonitrile in water with 0.1% TFA modifier) to afford the title compound as a white solid. $^1$H NMR (500 MHz, DMSO): δ 8.44 (s, 1 H), 8.13-8.16 (m, 2H), 7.57 (td, J=7.2, 2.0 Hz, 1 H), 7.07 (dd, J=8.5, 2.9 Hz, 1 H), 7.02 (d, J=8.6 Hz, 1 H), 6.88 (dd, J=6.4, 5.4 Hz, 1 H), 6.77 (d, J=8.3 Hz, 1 H), 5.34 (s, 2H), 4.10-4.49 (m, 2 H), 3.82 (s, 3 H), 2.52 (s, 3 H), 2.06 (dt, J=8.3, 4.9 Hz, 1 H), 1.80-1.85 (m, 1 H), 1.26 (dt, J=8.6, 5.1 Hz, 1 H), 1.03 (dt, J=8.6, 4.9 Hz, 1 H); LRMS m/z (M+H) 379.4 found, 379.2 required.

TABLE 1

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on $SiO_2$ (EtOAc/hexanes or MeOH/$CH_2Cl_2$), reverse phase chromatography (MeCN/$H_2O$/0.1% TFA), or preparative thin layer chromatography (EtOAc/hexanes or MeOH/$CH_2Cl_2$ MeOH/EtOAc), and were isolated as free-bases.

| Cpd. | Structure | Name | HRMS m/z (M + H) |
|---|---|---|---|
| 1-15 | 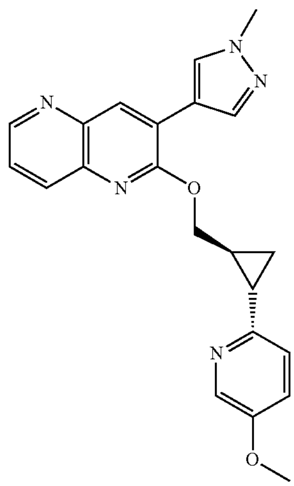 | 2-{[(1S,2S)-2-(5-methoxypyridin-2-yl)cyclopropyl]methoxy}-3-(1-methyl-1H-pyrazol-4-yl)-1,5-naphthyridine | 388.1768 found, 388.1771 required. |
| 1-16 | 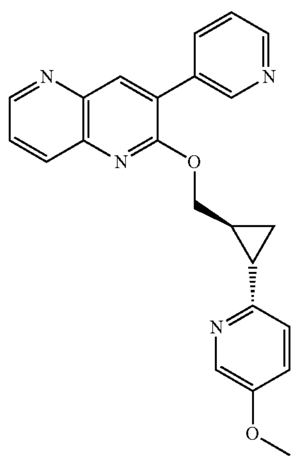 | 2-{[(1S,2S)-2-(5-methoxypyridin-2-yl)cyclopropyl]methoxy}-3-pyridin-3-yl-1,5-naphthyridine | 385.2 found, 385.2 required. |
| 1-17 | 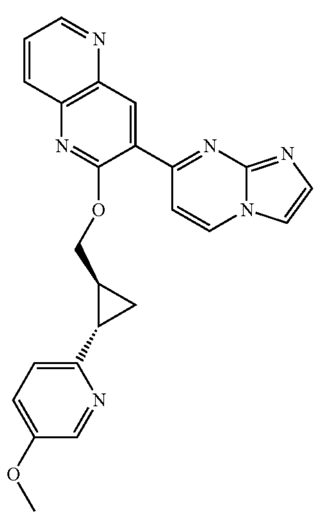 [SMILES: COc1ccc([C@H]2C[C@@H]2COc2nc3cccnc3cc2-c2ccn3ccnc3n2)nc1] | 3-imidazo[1,2-a]pyrimidin-7-yl-2-{[(1S,2S)-2-(5-methoxypyridin-2-yl)cyclopropyl]methoxy}-1,5-naphthyridine | 425.1717 found, 425.1721 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on $SiO_2$ (EtOAc/hexanes or MeOH/$CH_2Cl_2$), reverse phase chromatography (MeCN/$H_2O$/0.1% TFA), or preparative thin layer chromatography (EtOAc/hexanes or MeOH/$CH_2Cl_2$ MeOH/EtOAc), and were isolated as free-bases.

| Cpd. | Structure | Name | HRMS m/z (M + H) |
|---|---|---|---|
| 1-18 | 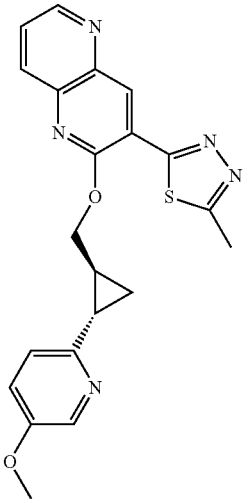 [SMILES: COc1ccc([C@H]2C[C@@H]2COc2nc3cccnc3cc2-c2nnc(C)s2)nc1] | 2-{[(1S,2S)-2-(5-methoxypyridin-2-yl)cyclopropyl]methoxy}-3-(5-methyl-1,3,4-thiadiazol-2-yl)-1,5-naphthyridine | 406.1329 found, 406.1332 required. |
| 1-19 | 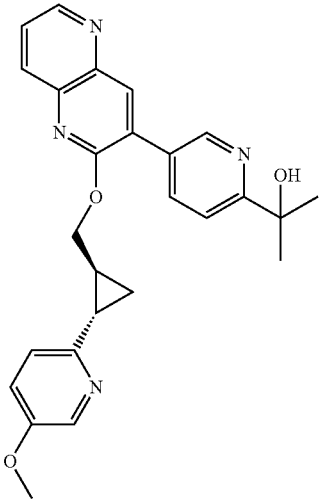 [SMILES: COc1ccc([C@H]2C[C@@H]2COc2nc3cccnc3cc2-c2ccc(C(C)(C)O)nc2)nc1] | 2-[5-(2-{[(1S,2S)-2-(5-methoxypyridin-2-yl)cyclopropyl]methoxy}-1,5-naphthyridin-3-yl)pyridin-2-yl]propan-2-ol | 443.2072 found, 443.2078 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on SiO$_2$ (EtOAc/hexanes or MeOH/CH$_2$Cl$_2$), reverse phase chromatography (MeCN/H$_2$O/0.1% TFA), or preparative thin layer chromatography (EtOAc/hexanes or MeOH/CH$_2$Cl$_2$ MeOH/EtOAc), and were isolated as free-bases.

| Cpd. | Structure | Name | HRMS m/z (M + H) |
|---|---|---|---|
| 1-20 | 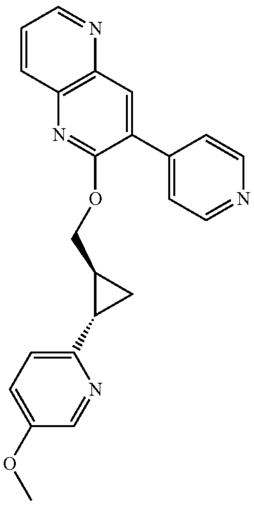 [SMILES: COc1ccc([C@H]2C[C@@H]2COc2nc3cccnc3cc2-c2ccncc2)nc1] | 2-{[(1S,2S)-2-(5-methoxypyridin-2-yl)cyclopropyl]methoxy-3-pyridin-4-yl-1,5-naphthyridine | 385.1655 found, 385.1659 required. |
| 1-21 | 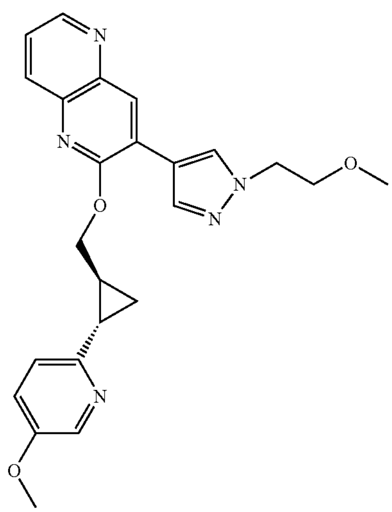 [SMILES: COCCn1cc(-c2cc3ncccc3nc2OC[C@H]2C[C@@H]2c2ccc(OC)cn2)cn1] | 3-[1-(2-methoxyethyl)-1H-pyrazol-4-yl]-2-{[(1S,2S)-2-(5-methoxypyridin-2-yl)cyclopropyl]methoxy}-1,5-naphthyridine | 432.2028 found, 432.2032 required. |
| 1-22 | 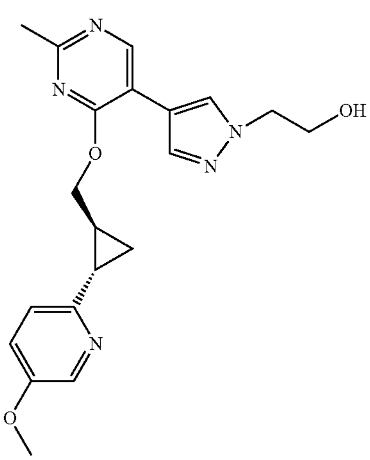 [SMILES: COc1ccc([C@H]2C[C@@H]2COc2nc(C)ncc2-c2cnn(CCO)c2)nc1] | 2-[4-(4-{[(1S,2S)-2-(5-methoxypyridin-2-yl)cyclopropyl]methoxy}-2-methylpyrimidin-5-yl)-1H-pyrazol-1-yl]ethanol | 382.1882 found, 382.1874 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on SiO$_2$ (EtOAc/hexanes or MeOH/CH$_2$Cl$_2$), reverse phase chromatography (MeCN/H$_2$O/0.1% TFA), or preparative thin layer chromatography (EtOAc/hexanes or MeOH/CH$_2$Cl$_2$ MeOH/EtOAc), and were isolated as free-bases.

| Cpd. | Structure | Name | HRMS m/z (M + H) |
|---|---|---|---|
| 1-23 | 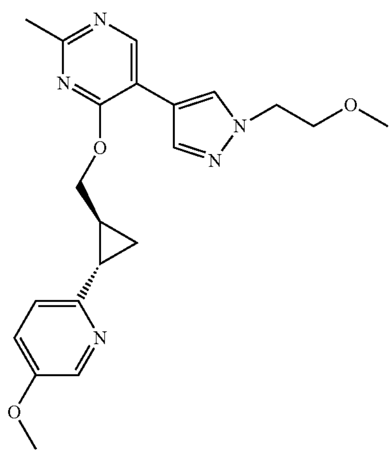 [SMILES: COCCn1cc(-c2cnc(C)nc2OC[C@H]2C[C@@H]2c2ccc(OC)cn2)cn1] | 5-[1-(2-methoxyethyl)-1H-pyrazol-4-yl]-4-{[(1S,2S)-2-(5-methoxypyridin-2-yl)cyclopropyl]methoxy}-2-methylpyrimidine | 396.2019 found, 396.2030 required. |
| 1-24 | 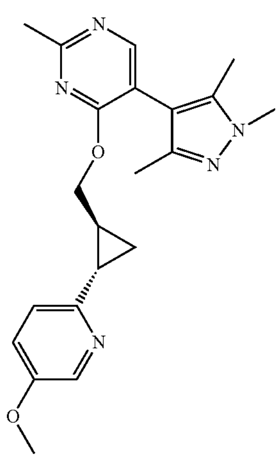 [SMILES: COc1ccc([C@H]2C[C@@H]2COc2nc(C)ncc2-c2c(C)nn(C)c2C)nc1] | 4-{[(1S,2S)-2-(5-methoxypyridin-2-yl)cyclopropyl]methoxy}-2-methyl-5-(1,3,5-trimethyl-1H-pyrazol-4-yl)pyrimidine | 380.2077 found, 380.2081 required. |
| 1-25 | 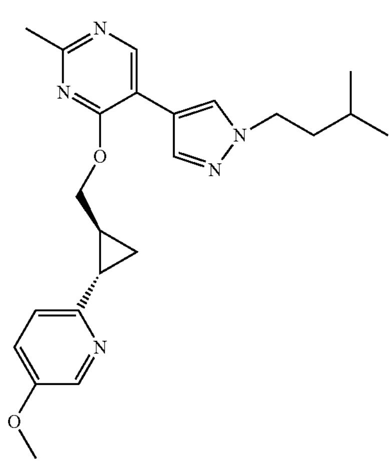 [SMILES: COc1ccc([C@H]2C[C@@H]2COc2nc(C)ncc2-c2cnn(CCC(C)C)c2)nc1] | 4-{[(1S,2S)-2-(5-methoxypyridin-2-yl)cyclopropyl]methoxy}-2-methyl-5-[1-(3-methylbutyl)-1H-pyrazol-4-yl]pyrimidine | 408.2392 found, 408.2394 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on SiO$_2$ (EtOAc/hexanes or MeOH/CH$_2$Cl$_2$), reverse phase chromatography (MeCN/H$_2$O/0.1% TFA), or preparative thin layer chromatography (EtOAc/hexanes or MeOH/CH$_2$Cl$_2$ MeOH/EtOAc), and were isolated as free-bases.

| Cpd. | Structure | Name | HRMS m/z (M + H) |
| --- | --- | --- | --- |
| 1-26 | 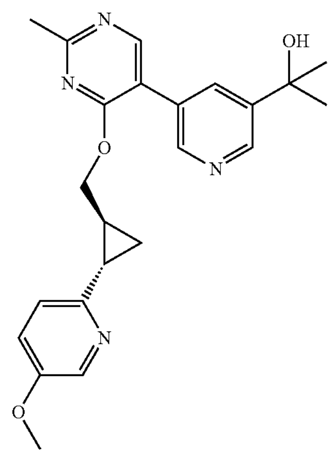 [SMILES: COc1ccc([C@H]2C[C@@H]2COc2nc(C)ncc2-c2cncc(C(C)(C)O)c2)nc1] | 2-[5-(4-{[(1S,2S)-2-(5-methoxypyridin-2-yl)cyclopropyl]methoxy}-2-methylpyrimidin-5-yl)pyridin-3-yl]propan-2-ol | 407.2065 found, 407.2078 required. |
| 1-27 | 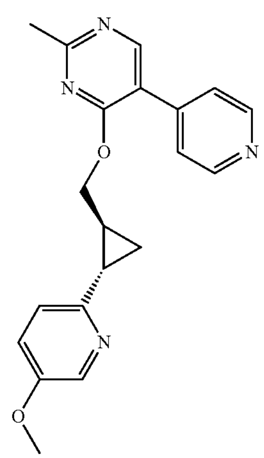 [SMILES: COc1ccc([C@H]2C[C@@H]2COc2nc(C)ncc2-c2ccncc2)nc1] | 4-{[(1S,2S)-2-(5-methoxypyridin-2-yl)cyclopropyl]methoxy}-2-methyl-5-pyridin-4-ylpyrimidine | 349.1655 found, 349.1659 required. |
| 1-28 | 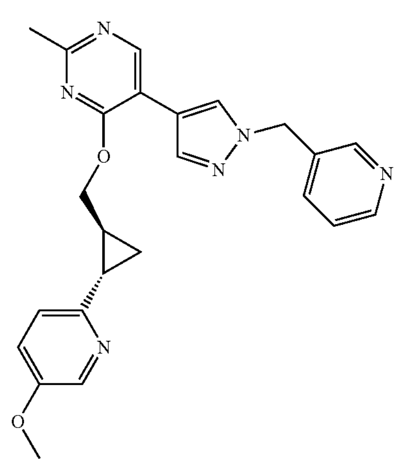 [SMILES: COc1ccc([C@H]2C[C@@H]2COc2nc(C)ncc2-c2cnn(Cc3cccnc3)c2)nc1] | 4-{[(1S,2S)-2-(5-methoxypyridin-2-yl)cyclopropyl]methoxy}-2-methyl-5-[1-(pyridin-3-ylmethyl)-1H-pyrazol-4-yl]pyrimidine | 429.2030 found, 429.2034 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on SiO$_2$ (EtOAc/hexanes or MeOH/CH$_2$Cl$_2$), reverse phase chromatography (MeCN/H$_2$O/0.1% TFA), or preparative thin layer chromatography (EtOAc/hexanes or MeOH/CH$_2$Cl$_2$ MeOH/EtOAc), and were isolated as free-bases.

| Cpd. | Structure | Name | HRMS m/z (M + H) |
|---|---|---|---|
| 1-29 | 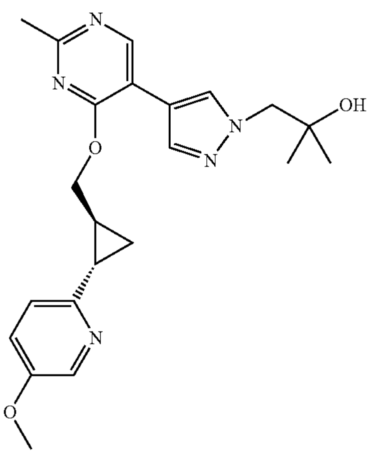 [SMILES: COc1ccc([C@H]2C[C@@H]2COc2nc(C)ncc2-c2cnn(CC(C)(C)O)c2)nc1] | 1-[4-(4-{[(1S,2S)-2-(5-methoxypyridin-2-yl)cyclopropyl]methoxy}-2-methylpyrimidin-5-yl)-1H-pyrazol-1-yl]-2-methylpropan-2-ol | 410.2173 found, 410.2187 required. |
| 1-30 | 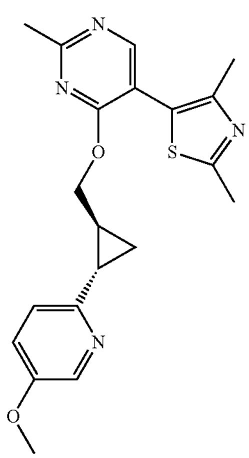 [SMILES: COc1ccc([C@H]2C[C@@H]2COc2nc(C)ncc2-c2sc(C)nc2C)nc1] | 5-(2,4-dimethyl-1,3-thiazol-5-yl)-4-{[(1S,2S)-2-(5-methoxypyridin-2-yl)cyclopropyl]methoxy-2-methylpyrimidine | 383.1530 found, 383.1536 required. |
| 1-31 | 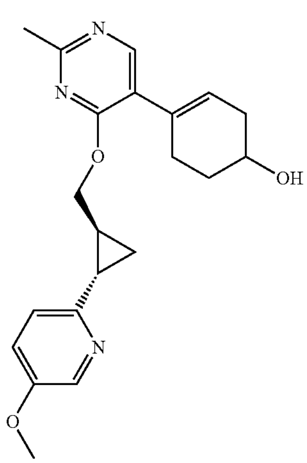 [SMILES: COc1ccc([C@H]2C[C@@H]2COc2nc(C)ncc2C2=CCC(O)CC2)nc1] | 4-(4-{[(1S,2S)-2-(5-methoxypyridin-2-yl)cyclopropyl]methoxy}-2-methylpyrimidin-5-yl)cyclohex-3-en-1-ol | 368.1974 found, 368.1971 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on $SiO_2$ (EtOAc/hexanes or MeOH/$CH_2Cl_2$), reverse phase chromatography (MeCN/$H_2O$/0.1% TFA), or preparative thin layer chromatography (EtOAc/hexanes or MeOH/$CH_2Cl_2$ MeOH/EtOAc), and were isolated as free-bases.

| Cpd. | Structure | Name | HRMS m/z (M + H) |
|---|---|---|---|
| 1-32 | 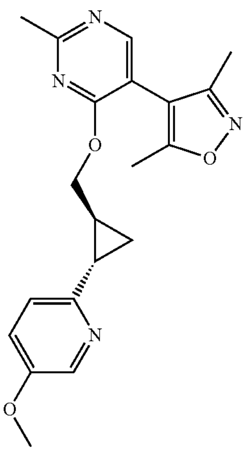 [SMILES: COc1ccc([C@H]2C[C@@H]2COc2nc(C)ncc2-c2c(C)noc2C)nc1] | 5-(3,5-dimethylisoxazol-4-yl)-4-{[(1S,2S)-2-(5-methoxypyridin-2-yl)cyclopropyl]methoxy}-2-methylpyrimidine | 367.1755 found, 367.1765 required. |
| 1-33 | 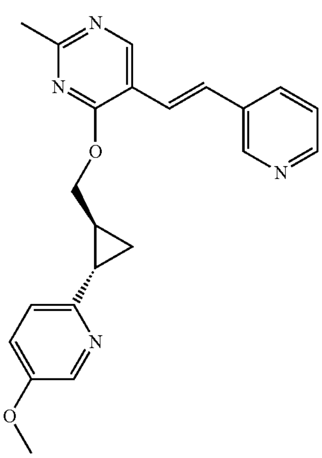 [SMILES: COc1ccc([C@H]2C[C@@H]2COc2nc(C)ncc2/C=C/c2cccnc2)nc1] | 4-{[(1S,2S)-2-(5-methoxypyridin-2-yl)cyclopropyl]methoxy}-2-methyl-5-[(E)-2-pyridin-3-ylethenyl]pyrimidine | 375.1815 found, 375.1816 required. |
| 1-34 | 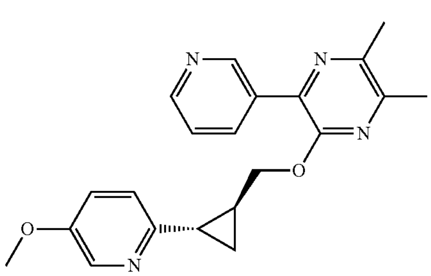 | 2-{[(1S,2S)-2-(5-methoxypyridin-2-yl)cyclopropyl]methoxy}-5,6-dimethyl-3-pyridin-3-ylpyrazine | 363.1808 found, 363.1818 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on SiO$_2$ (EtOAc/hexanes or MeOH/CH$_2$Cl$_2$), reverse phase chromatography (MeCN/H$_2$O/0.1% TFA), or preparative thin layer chromatography (EtOAc/hexanes or MeOH/CH$_2$Cl$_2$ MeOH/EtOAc), and were isolated as free-bases.

| Cpd. | Structure | Name | HRMS m/z (M + H) |
|---|---|---|---|
| 1-35 | 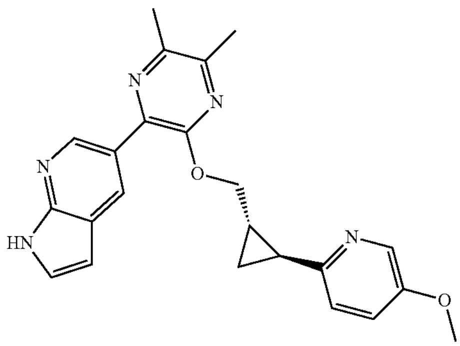 [SMILES: COc1ccc([C@H]2C[C@@H]2COc2nc(C)c(C)nc2-c2cnc3[nH]ccc3c2)nc1] | 5-(3-{[(1S,2S)-2-(5-methoxypyridin-2-yl)cyclopropyl]methoxy}-5,6-dimethylpyrazin-2-yl)-1H-pyrrolo[2,3-b]pyridine | 402.1931 found, 402.1925 required. |
| 1-36 | 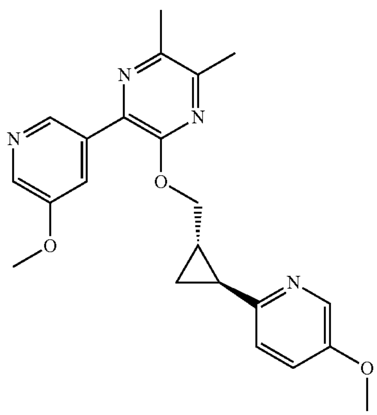 [SMILES: COc1ccc([C@H]2C[C@@H]2COc2nc(C)c(C)nc2-c2cncc(OC)c2)nc1] | 2-(5-methoxypyridin-3-yl)-3-{[(1S,2S)-2-(5-methoxypyridin-2-yl)cyclopropyl]methoxy}-5,6-dimethylpyrazine | 393.1919 found, 393.1921 required. |
| 1-37 | 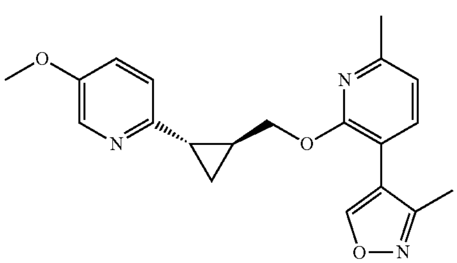 | 2-{[(1S,2S)-2-(5-methoxypyridin-2-yl)cyclopropyl]methoxy}-6-methyl-3-(3-methylisoxazol-4-yl)pyridine | 352.1649 found, 352.1656 required. |
| 1-38 | 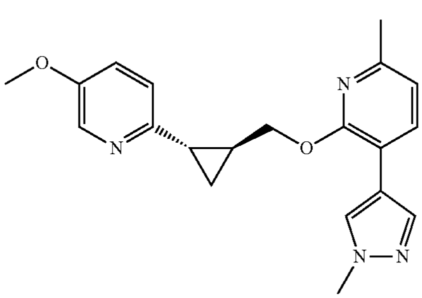 [SMILES: COc1ccc([C@H]2C[C@@H]2COc2nc(C)ccc2-c2cnn(C)c2)nc1] | 2-{[(1S,2S)-2-(5-methoxypyridin-2-yl)cyclopropyl]methoxy}-6-methyl-3-(1-methyl-1H-pyrazol-4-yl)pyridine | 351.1801 found, 351.1816 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on $SiO_2$ (EtOAc/hexanes or MeOH/$CH_2Cl_2$), reverse phase chromatography (MeCN/$H_2O$/0.1% TFA), or preparative thin layer chromatography (EtOAc/hexanes or MeOH/$CH_2Cl_2$ MeOH/EtOAc), and were isolated as free-bases.

| Cpd. | Structure | Name | HRMS m/z (M + H) |
|---|---|---|---|
| 1-39 | 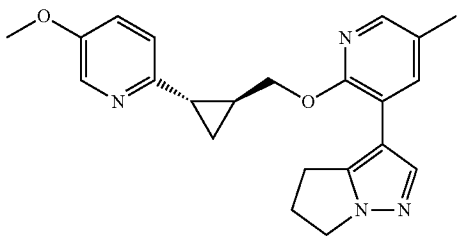 | 3-(2-{[(1S,2S)-2-(5-methoxypyridin-2-yl)cyclopropyl]methoxy}-5-methylpyridin-3-yl)-5,6-dihydro-4H-pyrrolo[1,2-b]pyrazole | 377.1963 found, 377.1972 required. |
| 1-40 | 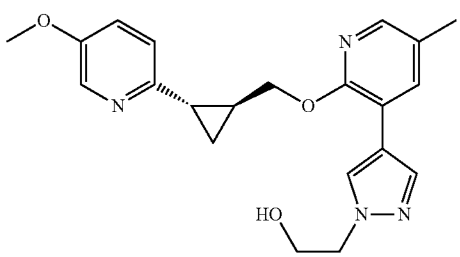 | 2-[4-(2-{[(1S,2S)-2-(5-methoxypyridin-2-yl)cyclopropyl]methoxy}-5-methylpyridin-3-yl)-1H-pyrazol-1-yl]ethanol | 381.1915 found, 381.1921 required. |
| 1-41 | 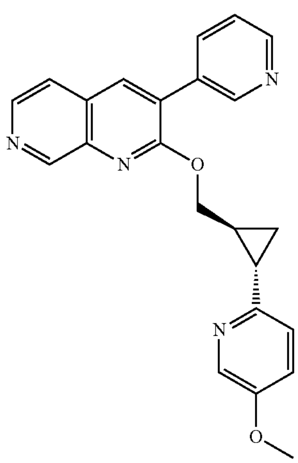 [SMILES: COc1ccc([C@H]2C[C@@H]2COc2nc3cnccc3cc2-c2cccnc2)nc1] | 2-{[(1S,2S)-2-(5-methoxypyridin-2-yl)cyclopropyl]methoxy}-3-pyridin-3-yl-1,7-naphthyridine | 385.1650 found, 385.1659 required. |
| 1-42 | 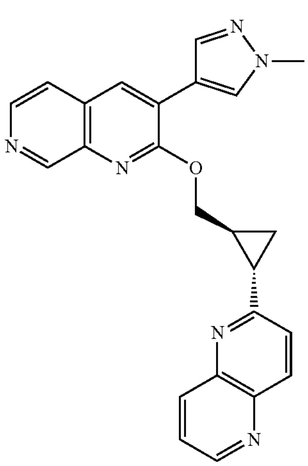 [SMILES: Cn1cc(-c2cc3ccncc3nc2OC[C@H]2C[C@@H]2c2ccc3ncccc3n2)cn1] | 2-[(1S,2S)-2-({[3-(1-methyl-1H-pyrazol-4-yl)-1,7-naphthyridin-2-yl]oxy}methyl)cyclopropyl]-1,5-naphthyridine | 409.2 found, 409.2 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on SiO$_2$ (EtOAc/hexanes or MeOH/CH$_2$Cl$_2$), reverse phase chromatography (MeCN/H$_2$O/0.1% TFA), or preparative thin layer chromatography (EtOAc/hexanes or MeOH/CH$_2$Cl$_2$ MeOH/EtOAc), and were isolated as free-bases.

| Cpd. | Structure | Name | HRMS m/z (M + H) |
|---|---|---|---|
| 1-43 | 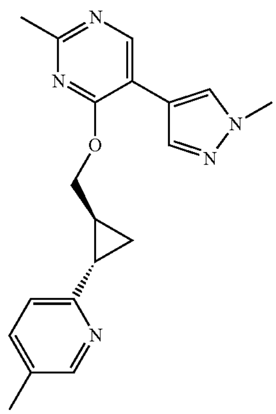 [SMILES: Cc1ccc([C@H]2C[C@@H]2COc2nc(C)ncc2-c2cnn(C)c2)nc1] | 2-methyl-5-(1-methyl-1H-pyrazol-4-yl)-4-{[(1S,2S)-2-(5-methylpyridin-2-yl)cyclopropyl]methoxy}pyrimidine | 336.1822 found, 336.1819 required. |
| 1-44 | 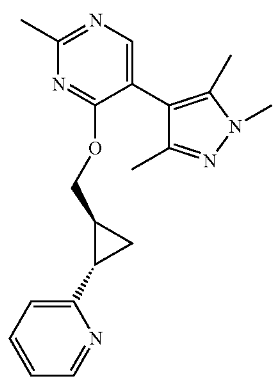 [SMILES: Cc1ncc(-c2c(C)nn(C)c2C)c(OC[C@H]2C[C@@H]2c2ccccn2)n1] | 2-methyl-4-{[(1S,2S)-2-pyridin-2-ylcyclopropyl]methoxy}-5-(1,3,5-trimethyl-1H-pyrazol-4-yl)pyrimidine | 350.1984 found, 350.1975 required. |
| 1-45 | 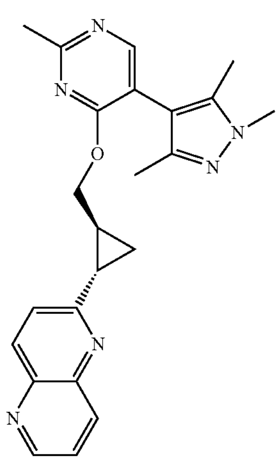 [SMILES: Cc1ncc(-c2c(C)nn(C)c2C)c(OC[C@H]2C[C@@H]2c2ccc3ncccc3n2)n1] | 2-[(1S,2S)-2-({[2-methyl-5-(1,3,5-trimethyl-1H-pyrazol-4-yl)pyrimidin-4-yl]oxy}methyl)cyclopropyl]-1,5-naphthyridine | 401.2096 found, 401.2084 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on $SiO_2$ (EtOAc/hexanes or MeOH/$CH_2Cl_2$), reverse phase chromatography (MeCN/$H_2O$/0.1% TFA), or preparative thin layer chromatography (EtOAc/hexanes or MeOH/$CH_2Cl_2$ MeOH/EtOAc), and were isolated as free-bases.

| Cpd. | Structure | Name | HRMS m/z (M + H) |
| --- | --- | --- | --- |
| 1-46 | 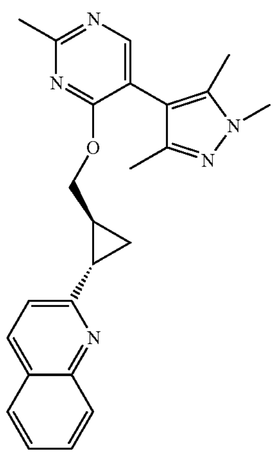 [SMILES: Cc1ncc(-c2c(C)nn(C)c2C)c(OC[C@H]2C[C@@H]2c2ccc3ccccc3n2)n1] | 2-[(1S,2S)-2-({[2-methyl-5-(1,3,5-trimethyl-1H-pyrazol-4-yl)pyrimidin-4-yl]oxy}methyl)cyclopropyl]quinoline | 400.2142 found, 400.2132 required. |
| 1-47 | 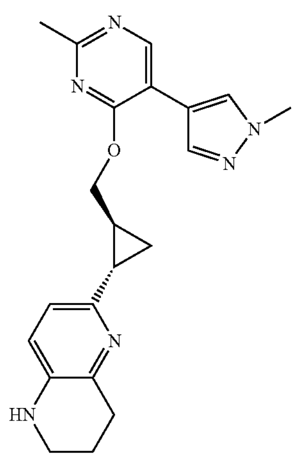 [SMILES: Cc1ncc(-c2cnn(C)c2)c(OC[C@H]2C[C@@H]2c2ccc3c(n2)CCCN3)n1] | 6-[(1S,2S)-2-({[2-methyl-5-(1-methyl-1H-pyrazol-4-yl)pyrimidin-4-yl]oxy}methyl)cyclopropyl]-1,2,3,4-tetrahydro-1,5-naphthyridine | 377.2089 found, 377.2084 required. |
| 1-48 | 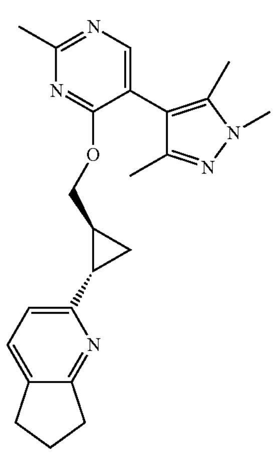 [SMILES: Cc1ncc(-c2c(C)nn(C)c2C)c(OC[C@H]2C[C@@H]2c2ccc3c(n2)CCC3)n1] | 2-[2-({[2-methyl-5-(1,3,5-trimethyl-1H-pyrazol-4-yl)pyrimidin-4-yl]oxy}methyl)-cyclopropyl]-6,7-dihydro-5H-cyclopenta[b]pyridine | 390.2297 found, 390.2288 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on SiO$_2$ (EtOAc/hexanes or MeOH/CH$_2$Cl$_2$), reverse phase chromatography (MeCN/H$_2$O/0.1% TFA), or preparative thin layer chromatography (EtOAc/hexanes or MeOH/CH$_2$Cl$_2$ MeOH/EtOAc), and were isolated as free-bases.

| Cpd. | Structure | Name | HRMS m/z (M + H) |
|---|---|---|---|
| 1-49 | 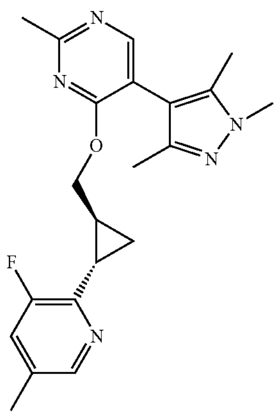 [SMILES: Cc1cnc([C@H]2C[C@@H]2COc2nc(C)ncc2-c2c(C)nn(C)c2C)c(F)c1] | 4-{[2-(3-fluoro-5-methylpyridin-2-yl)cyclopropyl]methoxy}-2-methyl-5-(1,3,5-trimethyl-1H-pyrazol-4-yl)pyrimidine | 382.2045 found, 382.2038 required. |
| 1-50 | 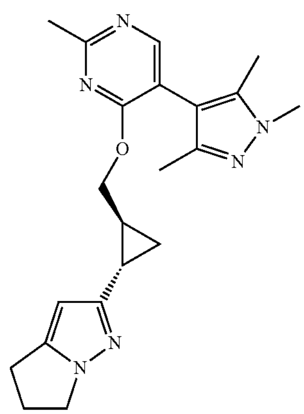 [SMILES: Cc1ncc(-c2c(C)nn(C)c2C)c(OC[C@H]2C[C@@H]2c2cc3n(n2)CCC3)n1] | 2-[2-({[2-methyl-5-(1,3,5-trimethyl-1H-pyrazol-4-yl)pyrimidin-4-yl]oxy}methyl)-cyclopropyl]-5,6-dihydro-4H-pyrrolo[1,2-b]pyrazole | 379.2247 found, 379.2241 required. |
| 1-51 | 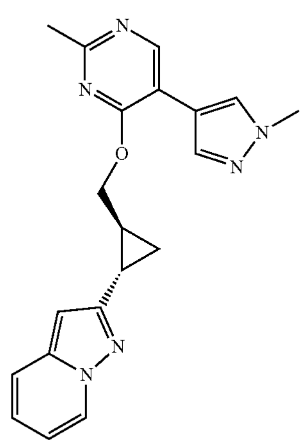 [SMILES: Cc1ncc(-c2cnn(C)c2)c(OC[C@H]2C[C@@H]2c2cc3ccccn3n2)n1] | 2-[2-({[2-methyl-5-(1-methyl-1H-pyrazol-4-yl)pyrimidin-4-yl]oxy}methyl)cyclopropyl]pyrazolo[1,5-a]pyridine | 361.1778 found, 361.1771 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on SiO$_2$ (EtOAc/hexanes or MeOH/CH$_2$Cl$_2$), reverse phase chromatography (MeCN/H$_2$O/0.1% TFA), or preparative thin layer chromatography (EtOAc/hexanes or MeOH/CH$_2$Cl$_2$ MeOH/EtOAc), and were isolated as free-bases.

| Cpd. | Structure | Name | HRMS m/z (M + H) |
|---|---|---|---|
| 1-52 | 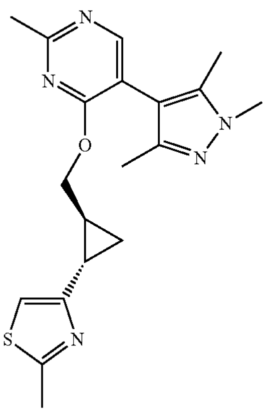 [SMILES: Cc1ncc(-c2c(C)nn(C)c2C)c(OC[C@H]2C[C@@H]2c2csc(C)n2)n1] | 2-methyl-4-{[2-(2-methyl-1,3-thiazol-4-yl)cyclopropyl]methoxy}-5-(1,3,5-trimethyl-1H-pyrazol-4-yl)pyrimidine | 370.1701 found 370.1696 required. |
| 1-53 | 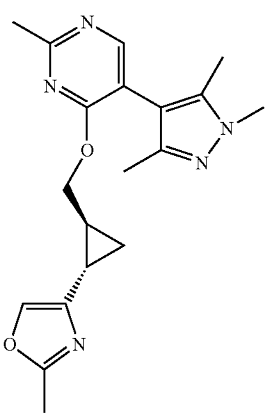 [SMILES: Cc1ncc(-c2c(C)nn(C)c2C)c(OC[C@H]2C[C@@H]2c2coc(C)n2)n1] | 2-methyl-4-{[2-(2-methyl-1,3-oxazol-4-yl)cyclopropyl]methoxy}-5-(1,3,5-trimethyl-1H-pyrazol-4-yl)pyrimidine | 354.1931 found, 354.1925 required. |
| 1-54 | 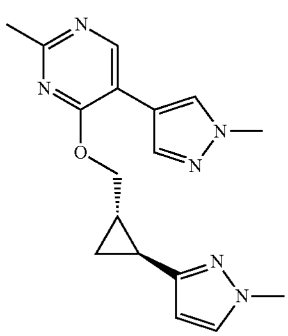 | 2-methyl-5-(1-methyl-1H-pyrazol-4-yl)-4-{[(1S,2S)-2-(1-methyl-1H-pyrazol-3-yl)cyclopropyl]methoxy}-pyrimidine | 325.1781 found, 325.1771 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on SiO$_2$ (EtOAc/hexanes or MeOH/CH$_2$Cl$_2$), reverse phase chromatography (MeCN/H$_2$O/0.1% TFA), or preparative thin layer chromatography (EtOAc/hexanes or MeOH/CH$_2$Cl$_2$ MeOH/EtOAc), and were isolated as free-bases.

| Cpd. | Structure | Name | HRMS m/z (M + H) |
| --- | --- | --- | --- |
| 1-55 | 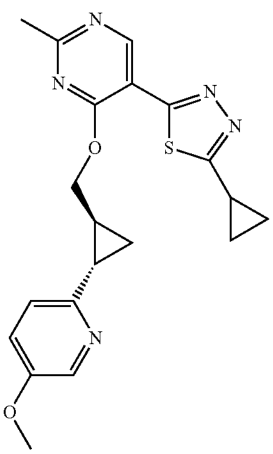 [SMILES: COc1ccc([C@H]2C[C@@H]2COc2nc(C)ncc2-c2nnc(C3CC3)s2)nc1] | 5-(5-cyclopropyl-1,3,4-thiadiazol-2-yl)-4-{[(1S,2S)-2-(5-methoxypyridin-2-yl)cyclopropyl]methoxy}-2-methylpyrimidine | 396.1500 found, 496.1489 required. |
| 1-56 | 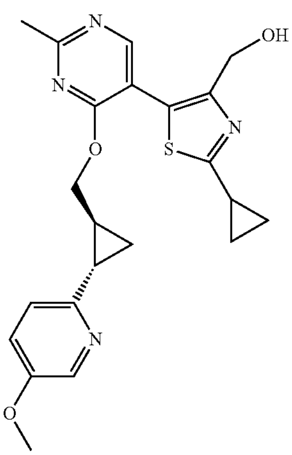 [SMILES: COc1ccc([C@H]2C[C@@H]2COc2nc(C)ncc2-c2sc(C3CC3)nc2CO)nc1] | [2-cyclopropyl-5-(4-{[(1S,2S)-2-(5-methoxypyridin-2-yl)cyclopropyl]methoxy}-2-methylpyrimidin-5-yl)-1,3-thiazol-4-yl]methanol | 447.1448 found, 447.1461 required. |
| 1-57 | 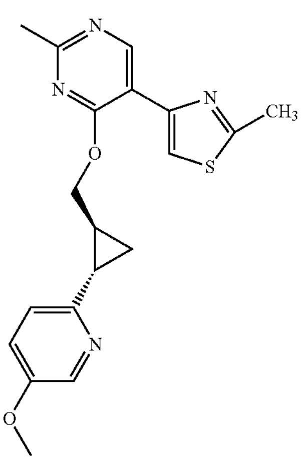 [SMILES: COc1ccc([C@H]2C[C@@H]2COc2nc(C)ncc2-c2csc(C)n2)nc1] | 4-{[(1S,2S)-2-(5-methoxypyridin-2-yl)cyclopropyl]methoxy}-2-methyl-5-(2-methyl-1,3-thiazol-4-yl)pyrimidine | 369.1386 found, 369.1380 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on SiO$_2$ (EtOAc/hexanes or MeOH/CH$_2$Cl$_2$), reverse phase chromatography (MeCN/H$_2$O/0.1% TFA), or preparative thin layer chromatography (EtOAc/hexanes or MeOH/CH$_2$Cl$_2$ MeOH/EtOAc), and were isolated as free-bases.

| Cpd. | Structure | Name | HRMS m/z (M + H) |
|---|---|---|---|
| 1-58 | 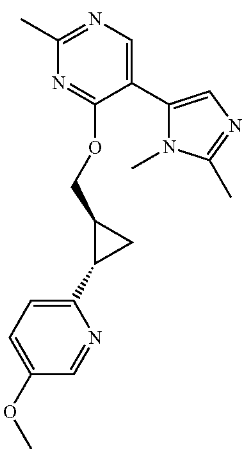 [SMILES: COc1ccc([C@H]2C[C@@H]2COc2nc(C)ncc2-c2cnc(C)n2C)nc1] | 5-(1,2-dimethyl-1H-imidazol-5-yl)-4-{[(1S,2S)-2-(5-methoxypyridin-2-yl)cyclopropyl]methoxy}-2-methylpyrimidine | 366.1932 found, 366.1925 required. |
| 1-59 | 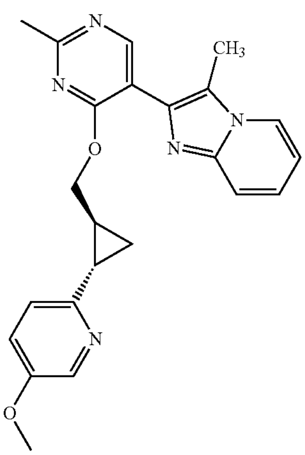 [SMILES: COc1ccc([C@H]2C[C@@H]2COc2nc(C)ncc2-c2nc3ccccn3c2C)nc1] | 2-(4-{[(1S,2S)-2-(5-methoxypyridin-2-yl)cyclopropyl]methoxy}-2-methylpyrimidin-5-yl)-3-methylimidazol[1,2-a]pyridine | 402.1936 found, 402.1925 required. |
| 1-60 | 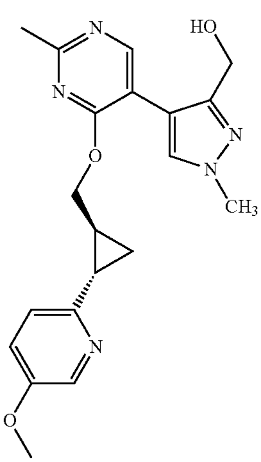 [SMILES: COc1ccc([C@H]2C[C@@H]2COc2nc(C)ncc2-c2cn(C)nc2CO)nc1] | [4-(4-{[(1S,2S)-2-(5-methoxypyridin-2-yl)cyclopropyl]methoxy}-2-methylpyrimidin-5-yl)-1-methyl-1H-pyrazol-3-yl]methanol | 382.1880 found, 382.1874 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on $SiO_2$ (EtOAc/hexanes or MeOH/$CH_2Cl_2$), reverse phase chromatography (MeCN/$H_2O$/0.1% TFA), or preparative thin layer chromatography (EtOAc/hexanes or MeOH/$CH_2Cl_2$ MeOH/EtOAc), and were isolated as free-bases.

| Cpd. | Structure | Name | HRMS m/z (M + H) |
|---|---|---|---|
| 1-61 | 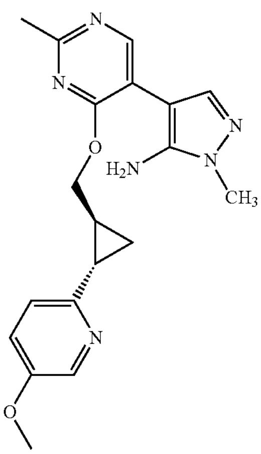 [SMILES: COc1ccc([C@H]2C[C@@H]2COc2nc(C)ncc2-c2cnn(C)c2N)nc1] | 4-(4-{[(1S,2S)-2-(5-methoxypyridin-2-yl)cyclopropyl]methoxy}-2-methylpyrimidin-5-yl)-1-methyl-1H-pyrazol-5-amine | 367.1884 found, 367.1877 required. |
| 1-62 | 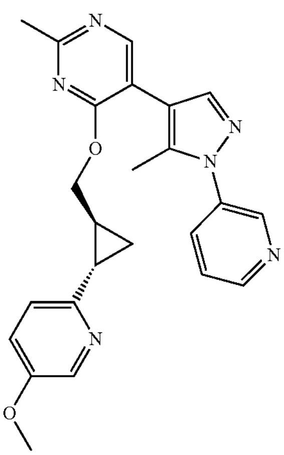 [SMILES: COc1ccc([C@H]2C[C@@H]2COc2nc(C)ncc2-c2cnn(-c3cccnc3)c2C)nc1] | 4-{[(1S,2S)-2-(5-methoxypyridin-2-yl)cyclopropyl]methoxy}-2-methyl-5-(5-methyl-1-pyridin-3-yl-1H-pyrazol-4-yl)pyrimidine | 429.2046 found, 429.2034 required. |
| 1-63 | 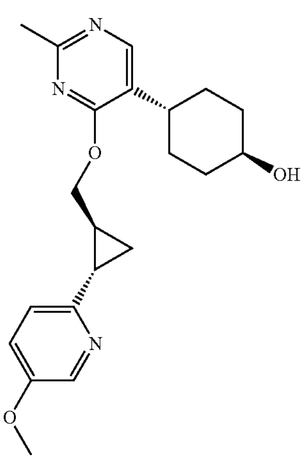 [SMILES: COc1ccc([C@H]2C[C@@H]2COc2nc(C)ncc2[C@H]2CC[C@H](O)CC2)nc1] | trans-4-(4-{[(1S,2S)-2-(5-methoxypyridin-2-yl)cyclopropyl]methoxy}-2-methylpyrimidin-5-yl)cyclohexanol | 370.2131 found, 370.2125 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on $SiO_2$ (EtOAc/hexanes or MeOH/$CH_2Cl_2$), reverse phase chromatography (MeCN/$H_2O$/0.1% TFA), or preparative thin layer chromatography (EtOAc/hexanes or MeOH/$CH_2Cl_2$ MeOH/EtOAc), and were isolated as free-bases.

| Cpd. | Structure | Name | HRMS m/z (M + H) |
|---|---|---|---|
| 1-64 | 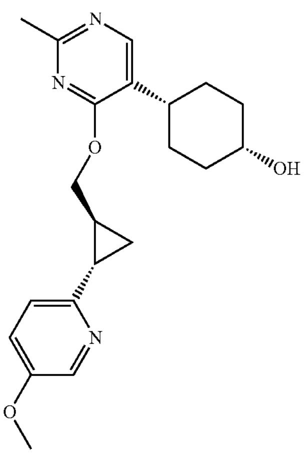 [SMILES: COc1ccc([C@H]2C[C@@H]2COc2nc(C)ncc2[C@H]2CC[C@@H](O)CC2)nc1] | cis-4-(4-{[(1S,2S)-2-(5-methoxypyridin-2-yl)cyclopropyl]methoxy}-2-methylpyrimidin-5-yl)cyclohexanol | 370.2129 found, 370.2125 required. |
| 1-65 | 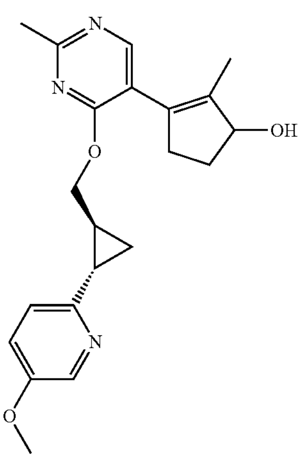 [SMILES: COc1ccc([C@H]2C[C@@H]2COc2nc(C)ncc2C2=C(C)C(O)CC2)nc1] | 3-(4-{[(1S,2S)-2-(5-methoxypyridin-2-yl)cyclopropyl]methoxy}-2-methylpyrimidin-5-yl)-2-methylcyclopent-2-en-1-ol | 368.1977 found, 368.1969 required. |
| 1-66 | 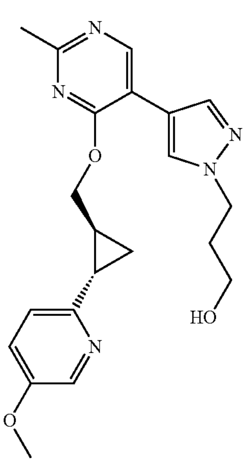 [SMILES: COc1ccc([C@H]2C[C@@H]2COc2nc(C)ncc2-c2cnn(CCCO)c2)nc1] | 3-[4-(4-{[(1S,2S)-2-(5-methoxypyridin-2-yl)cyclopropyl]methoxy}-2-methylpyrimidin-5-yl)-1H-pyrazol-1-yl]propan-1-ol | 396.2037 found, 396.2030 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on SiO$_2$ (EtOAc/hexanes or MeOH/CH$_2$Cl$_2$), reverse phase chromatography (MeCN/H$_2$O/0.1% TFA), or preparative thin layer chromatography (EtOAc/hexanes or MeOH/CH$_2$Cl$_2$ MeOH/EtOAc), and were isolated as free-bases.

| Cpd. | Structure | Name | HRMS m/z (M + H) |
| --- | --- | --- | --- |
| 1-67 | 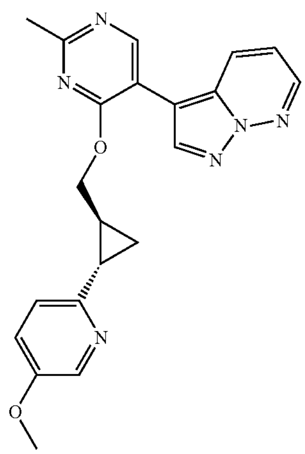 [SMILES: COc1ccc([C@H]2C[C@@H]2COc2nc(C)ncc2-c2cnn3ncccc23)nc1] | 3-(4-{[(1S,2S)-2-(5-methoxypyridin-2-yl)cyclopropyl]methoxy}-2-methylpyrimidin-5-yl)pyrazolo[1,5-b]pyridazine | 389.1727 found, 389.1721 required. |
| 1-68 | 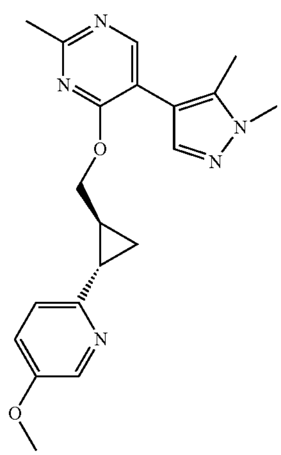 [SMILES: COc1ccc([C@H]2C[C@@H]2COc2nc(C)ncc2-c2cnn(C)c2C)nc1] | 5-(1,5-dimethyl-1H-pyrazol-4-yl)-4-{[(1S,2S)-2-(5-methoxypyridin-2-yl)cyclopropyl]methoxy}-2-methylpyrimidine | 366.1931 found, 366.1925 required. |
| 1-69 | 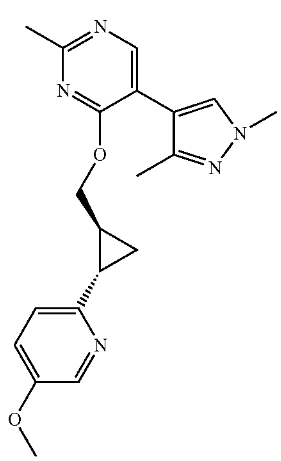 [SMILES: COc1ccc([C@H]2C[C@@H]2COc2nc(C)ncc2-c2cn(C)nc2C)nc1] | 5-(1,3-dimethyl-1H-pyrazol-4-yl)-4-{[(1S,2S)-2-(5-methoxpyridin-2-yl)cyclopropyl]methoxy}-2-methylpyrimidine | 366.1930 found, 366.1925 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on SiO$_2$ (EtOAc/hexanes or MeOH/CH$_2$Cl$_2$), reverse phase chromatography (MeCN/H$_2$O/0.1% TFA), or preparative thin layer chromatography (EtOAc/hexanes or MeOH/CH$_2$Cl$_2$ MeOH/EtOAc), and were isolated as free-bases.

| Cpd. | Structure | Name | HRMS m/z (M + H) |
|---|---|---|---|
| 1-70 | 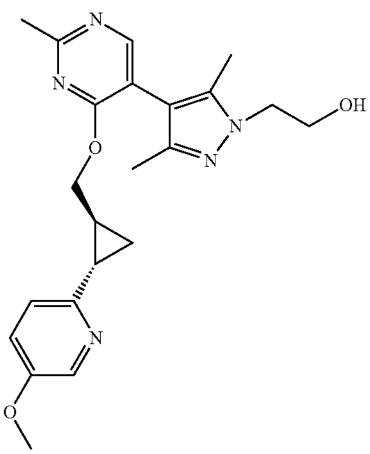 [SMILES: COc1ccc([C@H]2C[C@@H]2COc2nc(C)ncc2-c2c(C)nn(CCO)c2C)nc1] | 2-[4-(4-{[(1S,2S)-2-(5-methoxypyridin-2-yl)cyclopropyl]methoxy}-2-methylpyrimidin-5-yl)-3,5-dimethyl-1H-pyrazol-1-yl]ethanol | 410.2199 found, 410.2187 required. |
| 1-71 | 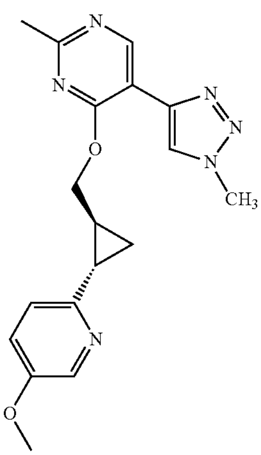 [SMILES: COc1ccc([C@H]2C[C@@H]2COc2nc(C)ncc2-c2cn(C)nn2)nc1] | 4-{[(1S,2S)-2-(5-methoxypyridin-2-yl)cyclopropyl]methoxy}-2-methyl-5-(1-methyl-1H-1,2,3-triazol-4-yl)pyrimidine | 363.1726 found, 353.1721 required. |
| 1-72 | 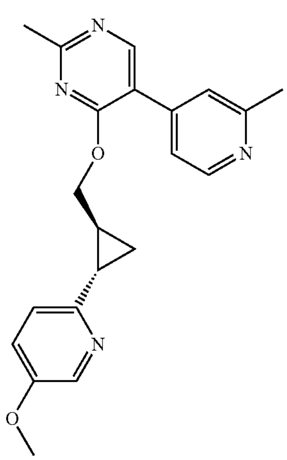 [SMILES: COc1ccc([C@H]2C[C@@H]2COc2nc(C)ncc2-c2ccnc(C)c2)nc1] | 4-{[(1S,2S)-2-(5-methoxypyridin-2-yl)cyclopropyl]methoxy}-2-methyl-5-(2-methylpyridin-4-yl)pyrimidine | 363.1807 found, 363.1816 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on SiO$_2$ (EtOAc/hexanes or MeOH/CH$_2$Cl$_2$), reverse phase chromatography (MeCN/H$_2$O/0.1% TFA), or preparative thin layer chromatography (EtOAc/hexanes or MeOH/CH$_2$Cl$_2$ MeOH/EtOAc), and were isolated as free-bases.

| Cpd. | Structure | Name | HRMS m/z (M + H) |
|---|---|---|---|
| 1-73 | 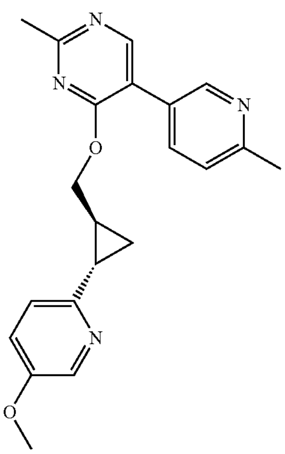 [SMILES: COc1ccc([C@H]2C[C@@H]2COc2nc(C)ncc2-c2ccc(C)nc2)nc1] | 4-{[(1S,2S)-2-(5-methoxypyridin-2-yl)cyclopropyl]methoxy}-2-methyl-5-(6-methylpyridin-3-yl)pyrimidine | 363.1810 found, 363.1816 required. |
| 1-74 | 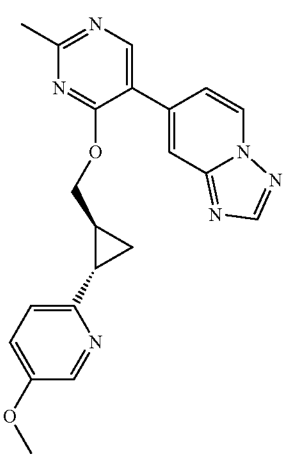 [SMILES: COc1ccc([C@H]2C[C@@H]2COc2nc(C)ncc2-c2ccn3ncnc3c2)nc1] | 7-(4-{[(1S,2S)-2-(5-methoxypyridin-2-yl)cyclopropyl]methoxy}-2-methylpyrimidin-5-yl)[1,2,4]triazolo[1,5-a]pyridine | 389.1708 found, 389.1721 required. |
| 1-75 | 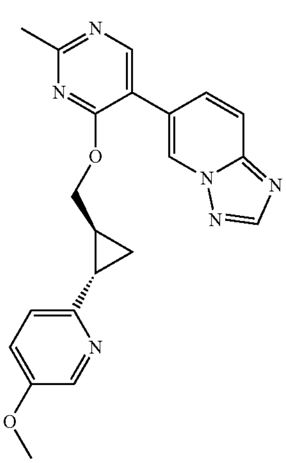 [SMILES: COc1ccc([C@H]2C[C@@H]2COc2nc(C)ncc2-c2ccc3ncnn3c2)nc1] | 6-(4-{[(1S,2S)-2-(5-methoxypyridin-2-yl)cyclopropyl]methoxy}-2-methylpyrimidin-5-yl)[1,2,4]triazolo[1,5-a]pyridine | 389.1706 found, 389.1721 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one in the art of organic synthesis without undue experimentation. Final products were purified by either elution on $SiO_2$ (EtOAc/hexanes or MeOH/$CH_2Cl_2$), reverse phase chromatography (MeCN/$H_2O$/0.1% TFA), or preparative thin layer chromatography (EtOAc/hexanes or MeOH/$CH_2Cl_2$ MeOH/EtOAc), and were isolated as free-bases.

| Cpd. | Structure | Name | HRMS m/z (M + H) |
|---|---|---|---|
| 1-76 | 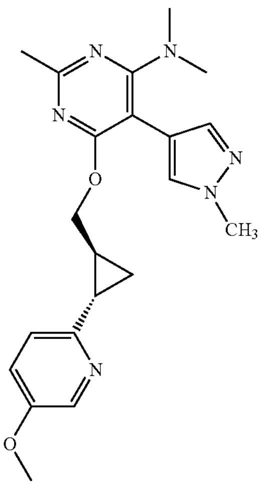 [SMILES: COc1ccc([C@H]2C[C@@H]2COc2nc(C)nc(N(C)C)c2-c2cnn(C)c2)nc1] | 6-{[(1S,2S)-2-(5-methoxypyridin-2-yl)cyclopropyl]methoxy}-N,N,2-trimethyl-5-(1-methyl-1H-pyrazol-4-yl)pyrimidin-4-amine | 395.2199 found, 395.2190 required. |
| 1-77 | 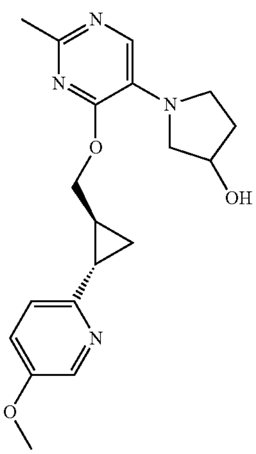 [SMILES: COc1ccc([C@H]2C[C@@H]2COc2nc(C)ncc2N2CCC(O)C2)nc1] | 1-(4-{[(1S,2S)-2-(5-methoxypyridin-2-yl)cyclopropyl]methoxy}-2-methylpyrimidin-5-yl)pyrrolidin-3-ol | 357.1927 found, 357.1921 required. |
| 1-78 | 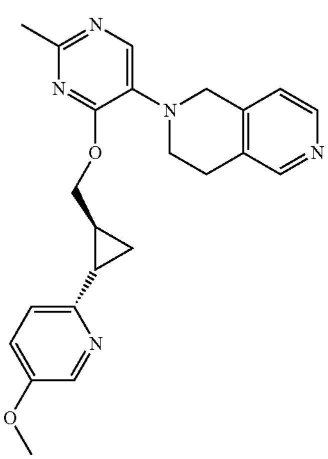 | 2-(4-{[(1S,2S)-2-(5-methoxypyridin-2-yl)cyclopropyl]methoxy}-2-methylpyrimidin-5-yl)-1,2,3,4-tetrahydro-2,6-naphthyridine | 404.2090 found, 404.2081 required. |

TABLE 2

The following tale shows representative data for the compounds of the Examples as PDE10 inhibitors as determined by the foregoing assays. In this table, the PDE10 Ki is a measure of the ability of the test compound to inhibit the action of the PDE10 enzyme.

| Cpd. | Structure | PDE10A Ki (nM) |
|---|---|---|
| LL3 | 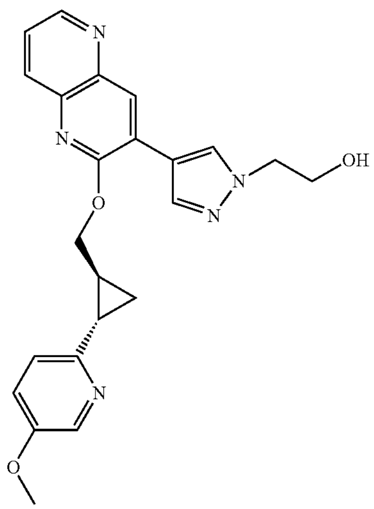 [SMILES: COc1ccc([C@H]2C[C@@H]2COc2nc3cccnc3cc2-c2cnn(CCO)c2)nc1] | 0.23 |
| MM4 | 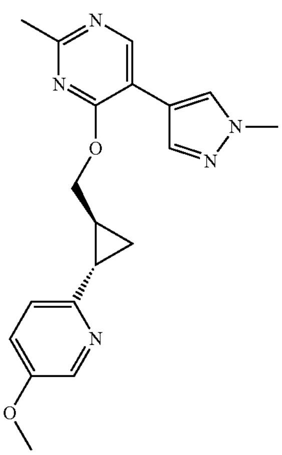 [SMILES: COc1ccc([C@H]2C[C@@H]2COc2nc(C)ncc2-c2cnn(C)c2)nc1] | 0.25 |
| 1-42 | 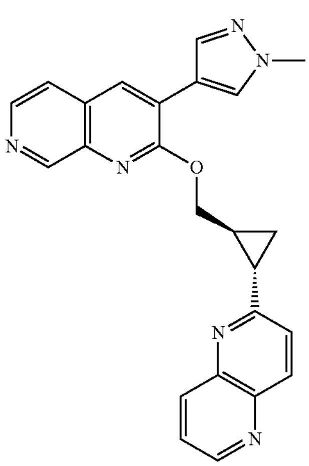 [SMILES: Cn1cc(-c2cc3ccncc3nc2OC[C@H]2C[C@@H]2c2ccc3ncccc3n2)cn1] | 0.04 |
| 1-46 | | 0.002 |
| TT1 | | 0.60 |
| RR4 | | 2.5 |

TABLE 2-continued

The following tale shows representative data for the compounds of the Examples as PDE10 inhibitors as determined by the foregoing assays. In this table, the PDE10 Ki is a measure of the ability of the test compound to inhibit the action of the PDE10 enzyme.

| Cpd. | Structure | PDE10A Ki (nM) |
|---|---|---|
| SS1 | 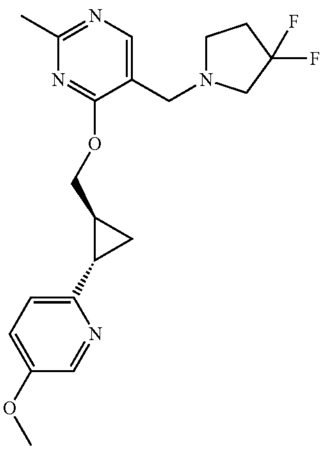 [SMILES: COc1ccc([C@H]2C[C@@H]2COc2nc(C)ncc2CN2CCC(F)(F)C2)nc1] | 60.8 |
| 1-54 | 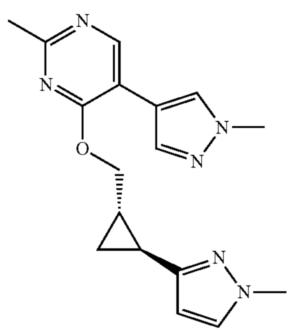 | 3.2 |
| 1-73 | 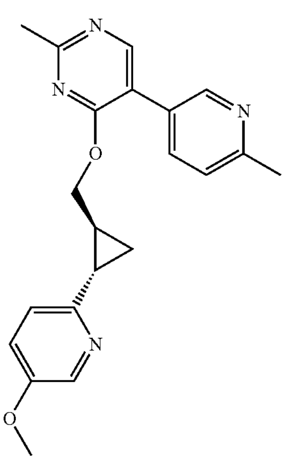 [SMILES: COc1ccc([C@H]2C[C@@H]2COc2nc(C)ncc2-c2ccc(C)nc2)nc1] | 0.80 |
| 1-55 | | 4.2 |
| 1-36 | | 0.22 |
| 1-39 | | 0.34 |

TABLE 2-continued

The following tale shows representative data for the compounds of the Examples as PDE10 inhibitors as determined by the foregoing assays. In this table, the PDE10 Ki is a measure of the ability of the test compound to inhibit the action of the PDE10 enzyme.

| Cpd. | Structure | PDE10A Ki (nM) |
|---|---|---|
| 1-31 | 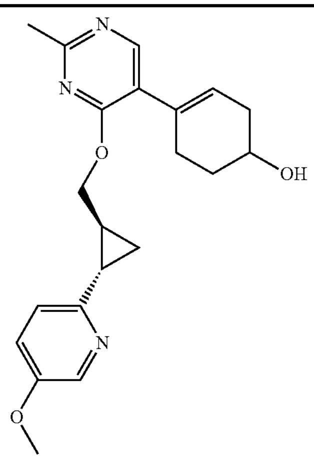 | 0.15 |
| 1-57 | 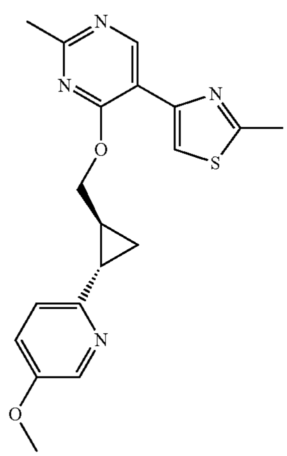 [SMILES: COc1ccc([C@H]2C[C@@H]2COc2nc(C)ncc2-c2csc(C)n2)nc1] | 0.78 |

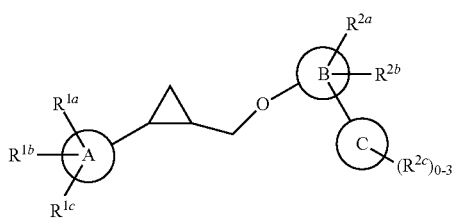

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

I wherein:

A is $C_{5-10}$heterocyclyl;

B is a $C_{5-10}$heterocyclyl selected from the group consisting of pyrimidinyl, naphthridinyl, pyrazinyl and pyridyl, wherein when B is pyrimidinyl it is presented by structural formula Ic:

Ic

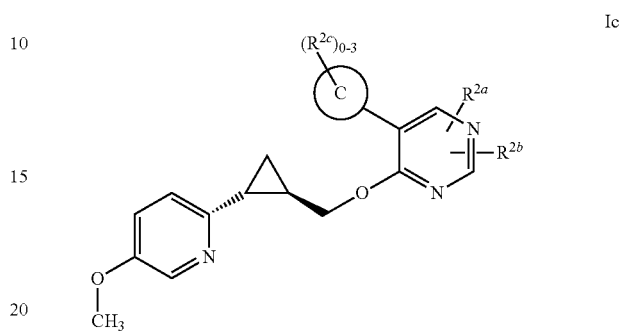

wherein $R^{2a}$ and $R^{2b}$ in Ic are selected from the group consisting of hydrogen, halogen, and $C_{1-6}$ alkyl;

C is selected from the group consisting of $(CH_2)_nC_{5-10}$heterocyclyl, $(CH_2)_nO—C_{5-10}$heterocyclyi, $C_{2-6}$alkenyl$C_{5-10}$heterocyclyl, $C_{3-10}$cycloalkyl, and $C_{3-10}$cycloalkenyl;

$R^{1a}$, $R^{1b}$ and $R^{1c}$ may be absent if the valency of A does not permit such substitution and are independently selected from the group consisting of:
(1) hydrogen,
(2) halogen,
(3) hydroxyl,
(4) $C_{1-6}$alkyl, which alkyl is unsubstituted or substituted with halogen, hydroxyl, phenyl or napthyl,
(5) —O—$C_{1-6}$alkyl, which alkyl is unsubstituted or substituted with halogen, hydroxyl or phenyl,
(6) phenyl, which is unsubstituted or substituted with 1 to 3 groups of $R^a$,
(7) $C_{5-10}$ heterocyclyl, which is unsubstituted or substituted with 1 to 3 groups of $R^a$,
(8) $C_{2-6}$alkenyl$C_{5-10}$ heterocyclyl, which heterocycle is unsubstituted or substituted with 1 to 3 groups of $R^a$,
(8) —O—phenyl, which is unsubstituted or substituted with 1 to 3 groups of $R^a$,
(9) $C_{3-10}$ocycloalkyl which is unsubstituted or substituted with 1 to 3 groups of $R^a$,
(10) —NH—$C_{1-6}$alkyl, or —N($C_{1-6}$alkyl)($C_{1-6}$alkyl), which alkyl is unsubstituted or substituted with 1 to 3 groups of $R^a$,
(11) —$CO_2H$,
(12) —CN, and
(13) —$NO_2$;

$R^{2a}$, and $R^{2b}$ may be absent if the valency of B does not permit such substitution, and $R^{2a}$, and $R^{2b}$ and $R^{2c}$ are independently selected from the group consisting of:
(1) hydrogen,
(2) halogen,
(3) hydroxyl,
(4) $C_{1-6}$alkyl, which alkyl is unsubstituted or substituted with halogen, OR, phenyl or napthyl,
(5) —O—$C_{1-6}$alkyl, which alkyl is unsubstituted or substituted with halogen, hydroxyl or phenyl,
(6) phenyl, which is unsubstituted or substituted with 1 to 3 groups of $R^a$, (7) (CH$_2$)$_n$heterocyclyl, which is unsubstituted or substituted with 1 to 3 groups of R$^a$,
(8) C$_{2-6}$alkenylC$_{5-10}$heterocyclyl, which is unsubstituted or substituted with 1 to 3 groups of R$^a$,
(9) (CH$_2$)$_n$O—C$_{5-10}$heterocyclyl, which is unsubstituted or substituted with 1 to 3 groups of R$^a$,
(10) C$_{3-10}$ocycloalkyl which is unsubstituted or substituted with 1 to 3 groups of R$^a$,
(11) —O-phenyl, which is unsubstituted or substituted with halogen, hydroxyl, —O—C$_{1-6}$alkyl or C$_{1-6}$alkyl, which is unsubstituted or substituted with fluoro,
(12) —N(R)$_2$, wherein when R is alkyl it is unsubstituted or substituted 1 to 3 groups of R$^a$,
(13) —CO$_2$R,
(14) B(OH)$_2$;
(15) —CN,
(16) —NO$_2$,
(17) C(O)R, and
(18) C$_{2-6}$alkenyl;
R is C$_{1-6}$alkyl or hydrogen;
R$^a$ is selected from the group consisting of:
(1) hydroxyl,
(2) halogen,
(3) C$_{1-6}$alkyl,
(4) —C$_{3-6}$cycloalkyl,
(5) —O—C$_{1-6}$alkyl,
(6) —O(C=O)—C$_{1-6}$alkyl,
(7) C$_{1-6}$alkylOH,
(8) (CH$_2$)$_n$O C$_{1-6}$alkyl
(8) —CO$_2$H,
(9) —CO$_2$-C$_{1-6}$alkyl,
(10) —C(O)—C$_{1-6}$alkyl,
(12) phenyl, which is unsubstituted or substituted with halogen, hydroxyl, —O—C$_{1-6}$alkyl or C$_{1-6}$alkyl, which is unsubstituted or substituted with fluoro,
(14) (CH$_2$)$_n$heterocyclyl, which is unsubstituted or substituted with halogen, hydroxyl, —O—C$_{1-6}$alkyl or C$_{1-6}$alkyl, which is unsubstituted or substituted with fluoro,
(15) —CN, and
(16) N(R)$_2$
n is 0-4;
or a pharmaceutically acceptable salt thereof.

2. The compound of claim 1 wherein A is selected from the group consisting of an optionally substituted pyridyl, cyclopentapyridinyl, dihydropyrrolopyrazolyl, pyrazolopyridinyl, thiazolyl, oxazolyl, pyrazolyl, quinolinyl, tetrahydronaphthyridinyl, and naphthyridine.

3. The compound of claim 1 wherein B is pyrimidinyl.

4. The compound according to claim 1 wherein R$^{1a}$, R$^{1b}$ and R$^{1c}$ are independently selected from hydrogen, hydrogen, C$_{1-6}$ alkyl, and —O—C$_{1-6}$alkyl.

5. The compound according to claim 1 of formula I wherein R$^{2a}$, R$^{2b}$ and R$^{2c}$ are independently selected from the group consisting of hydrogen, halogen, hydroxyl, C(O)R, CN, N(R)$_2$, pyrazolyl, C$_{1-6}$ alkyl, OC$_{1-6}$ alkyl, C$_{2-6}$ alkenyl, dimethylamino, dihydropyrrolopyrazolyl, thiazolyl, piperidinyl, pyrrolidinyl, ethenylpyridinyl, naphthyridinyl, C$_{1-6}$ alkylOH, (CH$_2$)$_n$pyridyl, imidazopyrimidinyl, methoxypyridinyl, thiadiazolyl, cyclohexenyl, cyclopropyl, cyclohexyl, isoxaolyl, pyridinylethenyl, cyclopentenyl, pyrrolopyridinyl, imidazolyl, pyrazolopyridazine, triazolyl, triazolopyridinyl, and of formula Ic wherein R$^{2a}$ and R$^{2b}$ are selected from hydrogen and C$_{1-6}$ alkyl, all of which, where appropriate, may be optionally substituted with 1 to 3 groups of R$^a$.

6. The compound according to claim 1 represented by structural formula Ia:

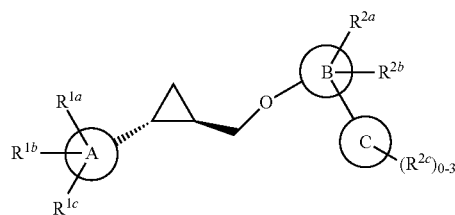

or a pharmaceutically acceptable salt thereof.

7. The compound according to claim 1 represented by structural formula Ib:

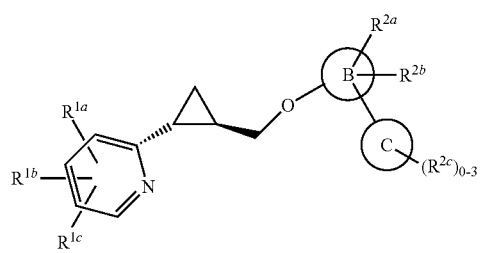

or a pharmaceutically acceptable salt thereof.

8. The compound according to claim 1 represented by structural formula Id:

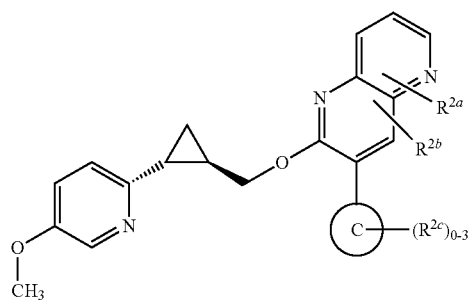

or a pharmaceutically acceptable salt thereof.

9. The compound according to claim 1 represented by structural formula Ie:

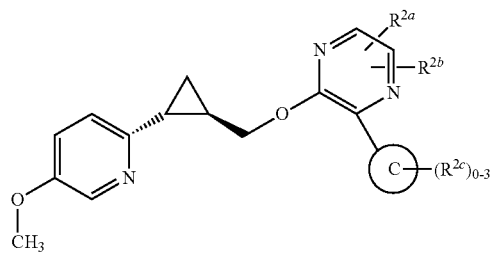

or a pharmaceutically acceptable salt thereof.

10. The compound according to claim 1 represented by structural formula If:

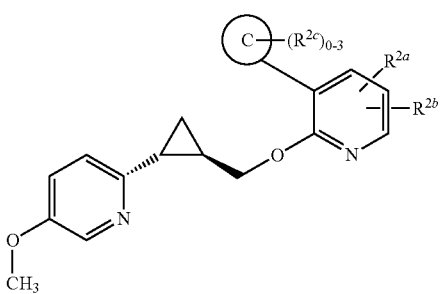

or a pharmaceutically acceptable salt thereof.

11. A compound which is selected from the group consisting of:

2-[4-(2-{[(1S,2S)-2-(5-methoxypyridin-2-yl)cyclopropyl]methoxy}-1,5-naphthyridin-3-yl)-1H-pyrazol-1-yl]ethanol,
4-{[(1S,2S)-2-(5-methoxypyridin-2-yl)cyclopropyl]methoxy}-2-methyl-5-(1-methyl-1H-pyrazol-4-yl)pyrimidine,
4-{[(1S,2S)-2-(5-methoxypyridin-2-yl)cyclopropyl]methoxy}-2-methyl-5-(1H-pyrazol-4-yl)pyrimidine, (2S)-2-[4-(4-{[(1S,2S)-2-(5-methoxypyridin-2-yl)cyclopropyl]methoxy}-2-methylpyrimidin-5-yl)-1H-pyrazol-1-yl]propan-1-ol,
3-(4-{[(1S,2S)-2-(5-methoxypyridin-2-yl)cyclopropyl]methoxy}-2-methylpyrimidin-5-yl)-5,6-dihydro-4H-pyrrolo[1,2-b]pyrazole,
3-(2,4-dimethyl-1,3-thiazol-5-yl)-2-{[(1S,2S)-2-(5-methoxypyridin-2-yl)cyclopropyl]-methoxy}-1,5-naphthyridine,
4-{[(1S,2S)-2-(5-methoxypyridin-2-yl)cyclopropyl]methoxy}-2-methyl-5-(2-methyl-1,3-thiazol-5-yl)pyrimidine,
2-{[(1S,2S)-2-(5-methoxypyridin-2-yl)cyclopropyl]methoxy}-3-(piperidin-3-yl)-1,5-naphthyridine, 1-[3-(2-{[(1S,2S)-2-(5-methoxypyridin-2-yl)cyclopropyl]methoxy}-1,5-naphthyridin-3-yl)piperidin-1-yl]ethanone,
5-[(3,3-difluoropyrrolidin-1-yl)methyl]-4-{[(1S,2 S)-2-(5-methoxypyridin-2-yl)cyclopropyl]methoxy}-2-methylpyrimidine,
4-{[(1S,2S)-2-(5-methoxypyridin-2-yl)cyclopropyl]methoxy}-2-methyl-5-[(E)-2-(pyridin-3-yl)ethenyl]pyrimidine,
4-{[(1S,2S)-2-(5-methoxypyridin-2-yl)cyclopropyl]methoxy}-2-methyl-5-[(E)-2-(6-methylpyridin-3-yl)ethenyl]pyrimidine,
3-(7,8-dihydro-1,6-naphthyridin-6(5H)-yl)-2-{[(1S,2S)-2-(5-methoxypyridin-2-yl)cyclopropyl]methoxy}-1,5-naphthyridine,
4-{[(1S,2S)-2-(5-methoxypyridin-2-yl)cyclopropyl]methoxy}-2-methyl-5-(1-methyl-1H-pyrazol-4-yl)pyrimidine,
2-methoxy-4-{[(1,2S)-2-(5-methoxypyridin-2-yl)cyclopropyl]methoxy}-5-(1-methyl-1H-pyrazol-4-yl)pyrimidine,
4-{[(1S,2S)-2-(5-methoxypyridin-2-yl)cyclopropyl]methoxy}-2,6-dimethyl-5-(1-methyl-1H-pyrazol-4-yl)pyrimidine,
4-{[(1S,2S)-2-(5-methoxypyridin-2-yl)cyclopropyl]methoxy}-2-methyl-5-[(pyridin-2-yloxy)methyl]pyrimidine,
2-{[(1S,2S)-2-(5-methoxypyridin-2-yl)cyclopropyl]methoxy}-3-(1-methyl-1H-pyrazol-4-yl)-1,5-naphthyridine,
2-{[(1S,2S)-2-(5-methoxypyridin-2-yl)cyclopropyl]methoxy}-3-pyridin-3-yl-1,5-naphthyridine, 3-imidazo[1,2-a]pyrimidin-7-yl-2-{[(1S,2S)-2-(5-methoxypyridin-2-yl)cyclopropyl]methoxy}-1,5-naphthyridine,
2-{[(1S,2S)-2-(5-methoxypyridin-2-yl)cyclopropyl]methoxy}-3-(5-methyl-1,3,4-thiadiazol-2-yl)-1,5-naphthyridine,
2-[5-(2-{[(1S,2S)-2-(5-methoxypyridin-2-yl)cyclopropyl]methoxy}-1,5-naphthyridin-3-yl)pyridin-2-yl]propan-2-ol,
2-{[(1S,2S)-2-(5-methoxypyridin-2-yl)cyclopropyl]methoxy}-3-pyridin-4-yl-1,5-naphthyridine, 3-[1-(2-methoxyethyl)-1H-pyrazol-4-yl]-2-{[(1S,2S)-2-(5-methoxypyridin-2-yl)cyclopropyl]methoxy}-1,5-naphthyridine,
2-[4-(4-{[(1S,2S)-2-(5-methoxypyridin-2-yl)cyclopropyl]methoxy}-2-methylpyrimidin-5-yl)-1H-pyrazol-1-yl]ethanol,
5-[1-(2-methoxyethyl)-1H-pyrazol-4-yl]-4-{[(1 S,2S)-2-(5-methoxypyridin-2-yl)cyclopropyl]methoxy}-2-methylpyrimidine,
4-{[(1S,2S)-2-(5-methoxypyridin-2-yl)cyclopropyl]methoxy}-2-methyl-5-(1,3,5-trimethyl-1H-pyrazol-4-yl)pyrimidine,
4-{[(1S,2S)-2-(5-methoxypyridin-2-yl)cyclopropyl]methoxy}-2-methyl-5-[1-(3-methylbutyl)-1H-pyrazol-4-yl]pyrimidine,
2-[5-(4-{[(1S,2S)-2-(5-methoxypyridin-2-yl)cyclopropyl]methoxy}-2-methylpyrimidin-5-yl)pyridin-3-yl]propan-2-ol,
4-{[(1S,2S)-2-(5-methoxypyridin-2-yl)cyclopropyl]methoxy}-2-methyl-5-pyridin-4-ylpyrimidine,
4-{[(1S,2S)-2-(5-methoxypyridin-2-yl)cyclopropyl]methoxy}-2-methyl-5-[1-(pyridin-3-ylmethyl)-1H-pyrazol-4-yl]pyrimidine,
1-[4-(4-{[(1S,2S)-2-(5-methoxypyridin-2-yl)cyclopropyl]methoxy}-2-methylpyrimidin-5-yl)-1H-pyrazol-1-yl]-2-methylpropan-2-ol,
5-(2,4-dimethyl-1,3-thiazol-5-yl)-4-{[(1S,2S)-2-(5-methoxypyridin-2-yl)cyclopropyl]methoxy}-2-methylpyrimidine,
4-(4-{[(1S,2S)-2-(5-methoxypyridin-2-yl)cyclopropyl]methoxy}-2-methylpyrimidin-5-yl)cyclohex-3-en-1-ol,
5-(3,5-dimethylisoxazol-4-yl)-4-{[(1S,2S)-2-(5-methoxypyridin-2-yl)cyclopropyl]methoxy}-2-methylpyrimidine,
4-{[(1S,2S)-2-(5-methoxypyridin-2-yl)cyclopropyl]methoxy}-2-methyl-5-[(E)-2-pyridin-3-ylethenyl]pyrimidine,
2-{[(1S,2S)-2-(5-methoxypyridin-2-yl)cyclopropyl]methoxy}-5,6-dimethyl-3-pyridin-3-ylpyrazine,
5-(3-{[(1S,2S)-2-(5-methoxypyridin-2-yl)cyclopropyl]methoxy}-5,6-dimethylpyrazin-2-yl)-1H-pyrrolo[2,3-b]pyridine,
2-(5-methoxypyridin-3-yl)-3-{[(1S,2S)-2-(5-methoxypyridin-2-yl)cyclopropyl]methoxy}-5,6-dimethylpyrazine,
2-{[(1S,2S)-2-(5-methoxypyridin-2-yl)cyclopropyl]methoxy}-6-methyl-3-(3-methylisoxazol-4-yl)pyridine,
2-{[(1S,2S)-2-(5-methoxypyridin-2-yl)cyclopropyl]methoxy}-6-methyl-3-(1-methyl-1H-pyrazol-4-yl)pyridine, 3-(2-{[(1S,2S)-2-(5-methoxypyridin-2-yl)cyclopropyl]methoxy}-5-methylpyridin-3-yl)-5,6-dihydro-4H-pyrrolo[1,2-b]pyrazole,
2-[4-(2-{[(1S,2S)-2-(5-methoxypyridin-2-yl)cyclopropyl]methoxy}-5-methylpyridin-3-yl)-1H-pyrazol-1-yl]ethanol,
2-{[(1S,2S)-2-(5-methoxypyridin-2-yl)cyclopropyl]methoxy}-3-pyridin-3-yl-1,7-naphthyridine,
2-[(1S,2S)-2-({[3-(1-methyl-1H-pyrazol-4-yl)-1,7-naphthyridin-2-yl]oxy}methyl)cyclopropyl]-1,5-naphthyridine,
2-methyl-5-(1-methyl-1H-pyrazol-4-yl)-4-{[(1S,2S)-2-(5-methylpyridin-2-yl)cyclopropyl]methoxy}pyrimidine,
2-methyl-4-{[(1S,2S)-2-pyridin-2-ylcyclopropyl]methoxy}-5-(1,3,5-trimethyl-1H-pyrazol-4-yl)pyrimidine,
2-[(1S,2S)-2-({[2-methyl-5-(1,3,5-trimethyl-1H-pyrazol-4-yl)pyrimidin-4-yl]oxy}methyl)cyclopropyl]-1,5-naphthyridine,
2-[(1S,2S)-2-({[2-methyl-5-(1,3,5-trimethyl-1H-pyrazol-4-yl)pyrimidin-4-yl]oxy}methyl)cyclopropyl]quinoline,
6-[(1S,2S)-2-({[2-methyl-5-(1-methyl-1H-pyrazol-4-ly)pyrimidin-4-yl]oxy}methyl)cyclopropyl]-1,2,3,4-tetrahydro-1,5-naphthyridine,
2-[2-({[2-methyl-5-(1,3,5-trimethyl-1H-pyrazol-4-yl)pyrimidin-4-yl]oxy}methyl)-cyclopropyl]-6,7-dihydro-5H-cyclopenta[b]pyridine,
4-{[2-(3-fluoro-5-methylpyridin-2-yl)cyclopropyl]methoxy}-2-methyl-5-(1,3,5-trimethyl-1H-pyrazol-4-yl)pyrimidine,
2-[2-({[2-methyl-5-(1,3,5-trimethyl-1H-pyrazol-4-yl)pyrimidin-4-yl]oxy}methyl)-cyclopropyl]-5,6-dihydro-4H-pyrrolo[1,2-b]pyrazole,
2-[2-({[2-methyl-5-(1-methyl-1-pyrazol-4-yl)pyrimidin-4-yl]oxy}methyl)cyclopropyl]-pyrazolo[1,5-a]pyridine,
2-methyl-4-{[2-(2-methyl-1,3-thiazol-4-yl)cyclopropyl]methoxy}-5-(1,3,5-trimethyl-1H-pyrazol-4-yl)pyrimidine,
2-methyl-4-{[2-(2-methyl-1,3-oxazol-4-yl)cyclopropyl]methoxy}-5-(1,3,5-trimethyl-1H-pyrazol-4-yl)pyrimidine,
2-methyl-5-(1-methyl-1H-pyrazol-4-yl)-4-{[(1S,2S)-2-(1-methyl-1H-pyrazol-3-yl)cyclopropyl]methoxy}pyrimidine,
5-(5-cyclopropyl-1,3,4-thiadiazol-2-yl)-4-{[(1S,2S)-2-(5-methoxypyridin-2-yl)cyclopropyl]methoxy}-2-methylpyrimidine,
[2-cyclopropyl-5-(4-{[(1S,2S)-2-(5-methoxypyridin-2-yl)cyclopropyl]methoxy}-2-methylpyrimidin-5-yl)-1,3-thiazol-4-yl]methanol,
4-{[(1S,2S)-2-(5-methoxypyridin-2-yl)cyclopropyl]methoxy}-2-methyl-5-(2-methyl-1,3-thiazol-4-yl)pyrimidine,
5-(1,2-dimethyl-1H-imidazol-5-yl)-4-{[(1S,2S)-2-(5-methoxypyridin-2-yl)cyclopropyl]-methoxy}-2-methylpyrimidine,
2-(4-{[(1S,2S)-2-(5-methoxypyridin-2-yl)cyclopropyl]methoxy}-2-methylpyrimidin-5-yl)-3-methylimidazo[1,2-a]pyridine,
[4-(4-{[(1S,2S)-2-(5-methoxypyridin-2-yl)cyclopropyl]methoxy}-2-methylpyrimidin-5-yl)-1-methyl-1H-pyrazol-3-yl]methanol,
4-(4-{[(1S,2S)-2-(5-methoxypyridin-2-yl)cyclopropyl]methoxy}-2-methylpyrimidin-5-yl)-1-methyl-1H-pyrazol-5-amine,
4-{[(1S,2S)-2-(5-methoxypyridin-2-yl)cyclopropyl]methoxy}-2-methyl-5-(5-methyl-1-pyridin-3-yl-1H-pyrazol-4-yl)pyrimidine,
trans-4-(4-{[(1S,2S)-2-(5-methoxypyridin-2-yl)cyclopropyl]methoxy}-2-methylpyrimidin-5-yl)cyclohexanol,
cis-4-(4-{[(1S,2S)-2-(5-methoxypyridin-2-yl)cyclopropyl]methoxy}-2-methylpyrimidin-5-yl)cyclohexanol,
3-(4-{[(1S,2S)-2-(5-methoxypyridin-2-yl)cyclopropyl]methoxy}-2-methylpyrimidin-5-yl)-2-methylcyclopent-2-en-1-ol,
3-[4-(4-{[(1S,2S)-2-(5-methoxypyridin-2-yl)cyclopropyl]methoxy}-2-methylpyrimidin-5-yl)-1H-pyrazol-1-yl]propan-1-ol,
3-(4-{[(1S,2S)-2-(5-methoxypyridin-2-yl)cyclopropyl]methoxy}-2-methylpyrimidin-5-yl)pyrazolo[1,5-b]pyridazine,
5-(1,5-dimethyl-1H-pyrazol-4-yl)-4-{[(1S,2S)-2-(5-methoxypyridin-2-yl)cyclopropyl]methoxy}-2-methylpyrimidine,
5-(1,3-dimethyl-1H-pyrazol-4-yl)-4-{[(1S,2S)-2-(5-methoxypyridin-2-yl)cyclopropyl]methoxy}-2-methylpyrimidine,
2-[4-(4-{[(1S,2S)-2-(5-methoxypyridin-2-yl)cyclopropyl]methoxy}-2-methylpyrimidin-5-yl)-3,5-dimethyl-1H-pyrazol-1-yl]ethanol,
4-{[(1S,2S)-2-(5-methoxypyridin-2-yl)cyclopropyl]methoxy}-2-methyl-5-(1-methyl-1H-1,2,3-triazol-4-yl)pyrimidine,
4-{[(1S,2S)-2-(5-methoxypyridin-2-yl)cyclopropyl]methoxy}-2-methyl-5-(2-methylpyridin-4-yl)pyrimidine,
4-{[(1S,2S)-2-(5-methoxypyridin-2-yl)cyclopropyl]methoxy}-2-methyl-5-(6-methylpyridin-3-yl)pyrimidine,
7-(4-{[(1S,2S)-2-(5-methoxypyridin-2-yl)cyclopropyl]methoxy}-2-methylpyrimidin-5-yl)[1,2,4]triazolo[1,5-a]pyridine,
6-(4-{[(1S,2S)-2-(5-methoxypyridin-2-yl)cyclopropyl]methoxy}-2-methylpyrimidin-5-yl)[1,2,4]triazolo[1,5-a]pyridine,
6-{[(1S,2S)-2-(5-methoxypyridin-2-yl)cyclopropyl]methoxy}-N,N,2-trimethyl-5-(1-methyl-1H-pyrazol-4-yl)pyrimidin-4-amine,
1-(4-{[(1S,2S)-2-(5-methoxypyridin-2-yl)cyclopropyl]methoxy}-2-methylpyrimidin-5-yl)pyrrolidin-3-ol,
2-(4-{[(1S,2S)-2-(5-methoxypyridin-2-yl)cyclopropyl]methoxy}-2-methylpyrimidin-5-yl)-1,2,3,4-tetrahydro-2,6-naphthyridine, or a pharmaceutically acceptable salt thereof.

12. The compound according to claim 11 which is:
2-[4-(4-{[(1S,2S)-2-(5-methoxypyridin-2-yl)cyclopropyl]methoxy}-2-methylpyrimidin-5-yl)-1H-pyrazol-1-yl]ethanol
4-(4-{[(1S,2S)-2-(5-methoxypyridin-2-yl)cyclopropyl]methoxy}-2-methylpyrimidin-5-yl)cyclohex-3-en-1-ol
[4-(4-{[(1S,2S)-2-(5-methoxypyridin-2-yl)cyclopropyl]methoxy}-2-methylpyrimidin-5-yl)-1-methyl-1H-pyrazol-3-yl]methanol
trans-4-(4-{[(1S,2S)-2-(5-methoxypyridin-2-yl)cyclopropyl]methoxy}-2-methylpyrimidin-5-yl)cyclohexanol
5-(1,3-dimethyl-1H-pyrazol-4-yl)-4-{[(1S,2S)-2-(5-methoxypyridin-2-yl)cyclopropyl]methoxy}-2-methylpyrimidine
4-{[(1S,2S)-2-(5-methoxypyridin-2-yl)cyclopropyl]methoxy}-2-methyl-5-(6-methylpyridin-3-yl)pyrimidine 2-[4-(2-{[(1S,2S)-2-(5-methoxypyridin-2-yl)cyclopropyl]methoxy}-1,5-naphthyridin-3-yl)-1H-pyrazol-1-yl]ethanol 4-{[(1S,2S)-2-(5-methoxypyridin-2-yl)cyclopropyl]methoxy}-2-methyl-5-(1-methyl-1H-pyrazol-4-yl)pyrimidine (2S)-2-[4-(4-{[(1S,2S)-2-(5-methoxypyridin-2-yl)cyclopropyl]methoxy}-2-methylpyrimidin-5-yl)-1H-pyrazol-1-yl]propan-1-ol or a pharmaceutically acceptable salt thereof.

13. A pharmaceutical composition which comprises a pharmaceutically acceptable carrier and a compound of claim 1 or a pharmaceutically acceptable salt thereof.

* * * * *